US012351807B2

(12) United States Patent
Kuhn et al.

(10) Patent No.: US 12,351,807 B2
(45) Date of Patent: Jul. 8, 2025

(54) REGULATORY NUCLEIC ACID MOLECULES FOR ENHANCING CONSTITUTIVE GENE EXPRESSION IN PLANTS

(71) Applicant: BASF PLANT SCIENCE COMPANY GMBH, Ludwigshafen (DE)

(72) Inventors: Josef Martin Kuhn, Ludwigshafen (DE); Linda Patricia Loyall, Limburgerhof (DE); Malte Siebert, Heidelberg (DE); Elke Duwenig, Limburgerhof (DE)

(73) Assignee: BASF Plant Science Company GmbH, Ludwigshafen am Rhein (DE)

( * ) Notice: Subject to any disclaimer, the term of this patent is extended or adjusted under 35 U.S.C. 154(b) by 22 days.

(21) Appl. No.: 18/357,691

(22) Filed: Jul. 24, 2023

(65) Prior Publication Data
US 2024/0035040 A1 Feb. 1, 2024

Related U.S. Application Data

(60) Continuation of application No. 16/907,693, filed on Jun. 22, 2020, now Pat. No. 11,708,578, which is a division of application No. 15/798,492, filed on Oct. 31, 2017, now Pat. No. 10,689,657, which is a division of application No. 13/393,028, filed as application No. PCT/EP2010/061659 on Aug. 11, 2010, now Pat. No. 9,828,607.

(60) Provisional application No. 61/238,230, filed on Aug. 31, 2009.

(30) Foreign Application Priority Data

Aug. 31, 2009 (EP) ..................................... 09169019

(51) Int. Cl.
C12N 15/82 (2006.01)
C12N 15/113 (2010.01)

(52) U.S. Cl.
CPC ........ C12N 15/8216 (2013.01); C12N 15/113 (2013.01); C12N 15/8241 (2013.01)

(58) Field of Classification Search
CPC ................................................. C12N 15/8216
USPC ...................................................... 800/278
See application file for complete search history.

(56) References Cited

U.S. PATENT DOCUMENTS

| | | | |
|---|---|---|---|
| 5,573,932 A | 11/1996 | Ellis et al. | |
| 5,750,866 A | 5/1998 | Dietrich et al. | |
| 8,071,383 B2 | 12/2011 | Arias et al. | |
| 9,828,607 B2 | 11/2017 | Kuhn et al. | |
| 10,689,657 B2 | 6/2020 | Kuhn et al. | |
| 11,708,578 B2 | 7/2023 | Kuhn et al. | |
| 2005/0216967 A1 | 9/2005 | Heim et al. | |
| 2005/0246785 A1 | 11/2005 | Cook et al. | |
| 2005/0262597 A1 | 11/2005 | Broekaert et al. | |
| 2006/0080747 A1 | 4/2006 | Keetman et al. | |
| 2006/0195934 A1 | 8/2006 | Apuya et al. | |
| 2006/0195943 A1 | 8/2006 | Feldmann et al. | |
| 2007/0006335 A1 | 1/2007 | Cook et al. | |
| 2007/0006345 A1 | 1/2007 | Alexandrov et al. | |
| 2007/0006347 A1 | 1/2007 | Plesch et al. | |
| 2009/0172837 A1 | 7/2009 | Geiger et al. | |
| 2010/0107275 A1* | 4/2010 | Tatarinova | C12N 15/8216 536/23.6 |
| 2010/0192237 A1 | 7/2010 | Ren et al. | |
| 2010/0199365 A1 | 8/2010 | Senger et al. | |
| 2011/0014706 A2 | 1/2011 | Cao et al. | |
| 2012/0084885 A1 | 4/2012 | Alexandrov et al. | |
| 2012/0159670 A1 | 6/2012 | Kuhn et al. | |
| 2012/0185965 A1 | 7/2012 | Senger et al. | |
| 2015/0052636 A1 | 2/2015 | Hartig et al. | |

FOREIGN PATENT DOCUMENTS

| | | |
|---|---|---|
| CL | 2007000696 A1 | 6/2008 |
| EP | 1033405 A2 | 9/2000 |
| EP | 1645633 A2 | 4/2006 |
| JP | 2009/529863 A | 8/2009 |
| RU | 2197527 C2 | 1/2003 |
| WO | WO-93/20216 A1 | 10/1993 |
| WO | WO-99/67389 A2 | 12/1999 |
| WO | WO-00/55325 A2 | 9/2000 |
| WO | WO-01/98480 A2 | 12/2001 |
| WO | WO-02/16655 A2 | 2/2002 |
| WO | WO-03/006660 A1 | 1/2003 |
| WO | WO-03/008596 | 9/2003 |
| WO | WO-03/102198 | 12/2003 |
| WO | WO-2006/003186 A1 | 1/2006 |
| WO | WO-2006/032426 A2 | 3/2006 |
| WO | WO-2006/089950 A2 | 8/2006 |
| WO | WO-2007/039454 A1 | 4/2007 |

(Continued)

OTHER PUBLICATIONS

Fourgoux-Nicol et al Plant Molecular Biology 40 :857-872 (Year: 1999).*
"*A. thaliana* At5g17920 gene constitutive promoter pSUH303GB", NCBI database, Accession No. AEH04981, Jun. 15, 2006.
"*Arabidopsis thaliana* cDNA Clone: RAFL22-53-N05, 5' End", EBI Database Accession No. BP820219, Jan. 22, 2005.
"*Arabidopsis thaliana* Chromosome 1 BAC T23K8 Sequence, Complete Sequence", GenBank Database Accession No. AC007230, May 13, 1999.
"*Arabidopsis thaliana* DNA chromosome 6, BAC clone F13G24 (Essa project)", EMBL database, Accession No. AL133421, Dec. 10, 1999.
"*Arabidopsis thaliana* Stress Regulated Gene Seq Id No. 3093", Database GeneSeq, Accession No. ABZ15288, Jan. 21, 2003.

(Continued)

*Primary Examiner* — Li Zheng
(74) *Attorney, Agent, or Firm* — ArentFox Schiff LLP

(57) ABSTRACT

The present invention is in the field of plant molecular biology and provides methods for production of high expressing constitutive promoters and the production of plants with enhanced constitutive expression of nucleic acids wherein nucleic acid expression enhancing nucleic acids (NEENAs) are functionally linked to the promoters and/or introduced into plants.

20 Claims, 5 Drawing Sheets

Specification includes a Sequence Listing.

(56) References Cited

FOREIGN PATENT DOCUMENTS

| WO | WO-2007/098042 A2 | 8/2007 |
|---|---|---|
| WO | WO-2007/107516 A2 | 9/2007 |
| WO | WO-2007/112326 A1 | 10/2007 |
| WO | WO-2008/009600 A1 | 1/2008 |
| WO | WO-2008/064128 A2 | 5/2008 |
| WO | WO-2008/104559 A1 | 9/2008 |
| WO | WO-2009/016202 A2 | 2/2009 |
| WO | WO-2009/037329 A2 | 3/2009 |
| WO | WO-2011/023537 A1 | 3/2011 |
| WO | WO-2011/023539 A1 | 3/2011 |
| WO | WO-2011/023800 A1 | 3/2011 |

OTHER PUBLICATIONS

"Petroselinum crispum UBI4-2 promoter sequence, Seq Id 7", NCBI database, Accession No. AJV61209, Nov. 29, 2007.
"Petroselinum crispum ubiquitin promoter DNA", NCBI database, Accession No. ADH50767, Mar. 25, 2004.
"Sequence 230 from Patent W00198480", EMBL Database, Accession No. AX461301, Jul. 8, 2002.
"Transgenic plant; promoter; ds; gene silencing; RNA interference; gene expression; PT0723", Genbank Database, Accession No. AJV39144, Nov. 29, 2007.
Baeumlein, H., et al., "A Novel Seed Protein Gene from *Vicia faba* is Developmentally Regulated in Transgenic Tobacco and *Arabidopsis* Plants", Mol. Gen. Genet., vol. 225, (1991), pp. 459-467.
Bruce, W. B., et al., "cis-Acting Elements Involved in Photoregulation of an Oat Phytochrome Promoter in Rice", The Plant Cell, vol. 2, (1990), pp. 1081-1089.
Callis, J., et al., "Introns Increase Gene Expression in Cultured Maize Cells", Genes & Development, vol. 1, (1987), pp. 1183-1200.
Chen, Z. L., et al., "A DNA Sequence Element that Confers Seed-Specific Enhancement to a Constitutive Promoter", The Embo J., 1988, vol. 7, No. 2, pp. 297-302.
Chilean Office Action Issued in Chilean Patent Application No. 2012-000550 Dated Feb. 11, 2015.
Chung, B.Y.W., et al., "Effect of 5_UTR Introns on Gene Expression in *Arabidopsis thaliana*", BMC Genomics, vol. 7, No. 120, (2006), pp. 1-13.
Decision of Grant Issued in Russian Patent Application No. 2012 112 346 Dated Apr. 1, 2015.
Decision of Grant Issued in Russian Patent Application No. 2012 112 347 Dated Apr. 1, 2015.
Ellis et al., The ocs element: a 16 base pair palindrome essential for activity of the octopine synthase enhancer, Embo J., 6(11):3203-8 (1987).
Extended European Search Report for European Application No. 16195551.3 Mailed Jun. 1, 2017.
Fu, H., et al., "A Potato Sus3 Sucrose Synthase Gene Contains a Context-Dependent 3' Element and a Leader Intron with Both Positive and Negative Tissue-Specific Effects", The Plant Cell, vol. 7, (1995), pp. 1395-1403.
Fu, H., et al., "High-Level Tuber Expression and Sucrose Inducibility of a Potato Sus4 Sucrose Synthase Gene Require 5' and 3' Flanking Sequences and the Leader Intron", Plant Cell, vol. 7, 1387-1394.
GenBank Accession AB005232. *Arabidopsis thaliana* genomic DNA, chromosome 5, P1 clone:MBG8. Published Feb. 14, 2004. pp. 1-25.
Gidekel, M., et al., "The First Intron of the *Arabidopsis thaliana* Gene Coding for Elongation Factor 113 Contains an Enhancer-Like Element", Gene, 1996, vol. 170, No. 2, pp. 201-206.
Huang, M.T.F., "Intervening Sequences Increase Efficiency of RNA 3' Processing and Accumulation of Cytoplasmic RNA", Nucleic Acid Research, vol. 18, No. 4, ((1989), pp. 937-947.
International Preliminary Report on Patentability for PCT/EP2010/061659, issued Mar. 6, 2012.
Japanese Office Action for Japanese Application No. 2012-525978 Dated Oct. 21, 2014 with English Translation Attached.
Kawalleck et al., Polyubiquitin gene expression and structural properties of the ubi4-2 gene in Petroselinum crispum, Plant Mol. Biol., 21(4):673-84 (1993).
Kim et al., A 20 nucleotide upstream element is essential for the nopaline synthase (nos) promoter activity, Plant Mol. Biol., 24(1):105-17 (1994).
Kim, M. J., et al., "Seed-Specific Expression of Sesame Microsomal Oleic Acid Desaturase is Controlled By Combinatorial Properties Between Negative cis-Regulatory Elements in the SeFAD2 Promoter and Enhancers in the 5'-UTR Intron", Mol. Gen., Genomics, vol. 276, (2006), pp. 351-368.
Last, D. I., et al., "pEmu: An Improved Promoter for Gene Expression in Cereal Cells", Theor. Appl. Genet., 1991, vol. 81, No. 5, pp. 581-588.
Le Hir, H., al., et "How Introns Influence and Enhance Eukaryotic Gene Expression", Trends in; Biochemical Sciences, vol. 28, No. 4, (2003), pp. 215-220.
Lu, J., et al., "Gene Expression Enhancement Mediated by the 5' UTR Intron of the Rice rubi3 Gene Varied Remarkably Among Tissues in Transgenic Rice Plants", Mol. Genet. Genomics, vol. 279, (2008), pp. 563-572.
Nott, A., et al., "Splicing Enhances Translation in Mammalian Cells: an Additional Function of the Exon Junction Complex", Genes & Development, vol. 18, (2004), pp. 210-222.
Rose, A., B., al., et "Promoter-Proximal Introns in *Arabidopsis thatliana* are Enriched in Dispersed Signals that Elevate Gene Expression", The Plant Cell, vol. 20, (2008), pp. 543-551.
Rose,A. B., "The Effect of Intron Location on Intron-Mediated Enhancement of Gene Expression in *Arabidopsis*", The Plant Journal, vol. 40, (2004), pp. 744-751.
Schunmann, P.H.D., et al., Characterization of Promoter Expression Patterns Derived from the Pht1 Phosphate Transporter Genes of Barley (*Hordeum vulgare* L.), Journal of Experimental Botany, vol. 55, No. 398, (2004), pp. 855-865.
Sieburth, L. E., "Molecular Dissection of the AGAMOUS Control Region Shows that cis Elements for Spatial Regulation are Located Intragenically", The Plant Cell, vol. 9, (1997), pp. 355-365.
Thomas, M. S., et al, "Identification of an Enhancer Element for the Endosperm-Specific Expression of High Molecular Weight Glutenin", The Plant Cell, vol. 2, (1990), pp. 1171-1180.
Vasil, V., et al., "Increased Gene Expression by the First Intron of Maize Shrunken-1 Locus in Grass Species", Plant Physiol., vol. 91, (1989), pp. 1575-1579.
Vitale, A., et al., "Multiple Conserved 5' Elements are Required for High-Level Pollen Expression of the *Arabidopsis* Reproductive Actin ACT1", Plant Molecular Biology, vol. 52, (2003), pp. 11351151.
Wang, S., et al., "Control of Plant Trichome Development by a Cotton Fiber MYB Gene", The Plant Cell, vol. 16, (2004), pp. 2323-2334.
Wilmink, A., et al., "Activity of Constitutive Promoters in Various Species from the Liliaceae", Plant Molecular Biology, 1995, vol. 28, pp. 949-955.
Xie M., al., et "Bidirectionalization of Polar Promoters in Plants", Nature Biotechnology, vol. 19,; ; (2001), pp. 677-678.

* cited by examiner

A)

B)

REGULATORY NUCLEIC ACID MOLECULES FOR ENHANCING CONSTITUTIVE GENE EXPRESSION IN PLANTS

RELATED APPLICATIONS

This application is a continuation of application Ser. No. 16/907,693, filed Jun. 22, 2020, now U.S. Pat. No. 11,708,578, which is a divisional of application Ser. No. 15/798,492, filed Oct. 31, 2017, now U.S. Pat. No. 10,689,657, which is a divisional application of U.S. application Ser. No. 13/393,028, now U.S. Pat. No. 9,828,607, which is a national stage application (under 35 U.S.C. § 371) of PCT/EP2010/061659, filed Aug. 11, 2010 which claims benefit of U.S. Provisional Application No. 61/238,230, filed Aug. 31, 2009 and European Application No. 09169019.8, filed Aug. 31, 2009. The entire contents of each of these applications are hereby incorporated by reference herein in their entirety.

SUBMISSION OF SEQUENCE LISTING

The Sequence Listing associated with this application is filed in electronic format via Patent Center and hereby incorporated by reference into the specification in its entirety. The name of the file containing the Sequence Listing is 62515B Seqlisting.XML. The size of the file is 158,798 bytes and the text file was created on Jul. 18, 2023.

BACKGROUND OF THE INVENTION

The present invention is in the field of plant molecular biology and provides methods for production of high expressing constitutive promoters and the production of plants with enhanced constitutive expression of nucleic acids wherein nucleic acid expression enhancing nucleic acids (NEENAs) are functionally linked to said promoters and/or introduced into plants.

Expression of transgenes in plants is strongly affected by various external and internal factors resulting in a variable and unpredictable level of transgene expression. Often a high number of transformants have to be produced and analyzed in order to identify lines with desirable expression strength. As transformation and screening of lines with desirable expression strength is costly and labor intensive there is a need for high expression of one ore more transgenes in a plant. This problem is especially pronounced, when several genes have to be coordinately expressed in a transgenic plant in order to achieve a specific effect as a plant has to be identified in which each and every gene is strongly expressed.

For example, expression of a transgene can vary significantly, depending on construct design and positional effects of the T-DNA insertion locus in individual transformation events.

Strong promoters can partially overcome these challenges. However, availability of suitable promoters showing strong expression with the desired specificity is often limited. In order to ensure availability of sufficient promoters with desired expression specificity, the identification and characterization of additional promoters can help to close this gap. However, natural availability of promoters of the respective specificity and strength and the time consuming characterization of promoter candidates impedes the identification of suitable new promoters.

In order to overcome these challenges, diverse genetic elements and/or motifs have been shown to positively affect gene expression. Among these, some introns have been recognized as genetic elements with a strong potential for improving gene expression. Although the mechanism is largely unknown, it has been shown that some introns positively affect the steady state amount of mature mRNA, possibly by enhanced transcriptional activity, improved mRNA maturation, enhanced nuclear mRNA export and/or improved translation initiation (e.g. Huang and Gorman, 1990; Le Hir et al., 2003; Nott et al., 2004). Since only selected introns were shown to increase expression, splicing as such is likely not accountable for the observed effects.

The increase of gene expression observed upon functionally linking introns to promoters is called intron mediated enhancement (IME) of gene expression and has been shown in various monocotyledonous (e.g. Callis et al., 1987; Vasil et al., 1989; Bruce et al., 1990; Lu et al., 2008) and dicotyledonous plants (e.g. Chung et al., 2006; Kim et al., 2006; Rose et al., 2008). In this respect, the position of intron in relation to the translational start site (ATG) was shown to be crucial for intron mediated enhancement of gene expression (Rose et al., 2004).

Next to their potential for enhancing gene expression, a few introns were shown to also affect the tissue specificity in their native nucleotide environment in plants. Reporter gene expression was found to be dependent on the presence of genomic regions containing up to two introns (Sieburth et al., 1997; Wang et al., 2004). 5' UTR introns have also been reported to be of importance for proper functionality of promoter elements, likely due to tissue specific gene control elements residing in the introns (Fu et al., 1995a; Fu et al., 1995b; Vitale et al., 2003; Kim et al., 2006). However, these studies also show that combination of introns with heterologous promoters can have strong negative impacts on strength and/or specificity of gene expression (Vitale et al., 2003; Kim et al., 2006, WO2006/003186, WO2007/098042). For example the strong constitutive Cauliflower Mosaic Virus CaMV35S promoter is negatively affected through combination with the sesame SeFAD2 5'UTR intron (Kim et al., 2006). In contrast to these observations, some documents show enhanced expression of a nucleic acid by IME without affecting the tissue specificity of the respective promoter (Schünmann et al., 2004).

In the present application further nucleic acid molecules are described that enhance the expression of said promoters without affecting their specificity upon functionally linkage to constitutive promoters. These nucleic acid molecules are in the present application described as "nucleic acid expression enhancing nucleic acids" (NEENA). Introns have the intrinsic feature to be spliced out of the respective pre-mRNA. In contrast to that the nucleic acids presented in the application at hand, do not necessarily have to be included in the mRNA or, if present in the mRNA, have not necessarily to be spliced out of the mRNA in order to enhance the expression derived from the promoter the NEENAs are functionally linked to.

DETAILED DESCRIPTION OF THE INVENTION

Figure 1:
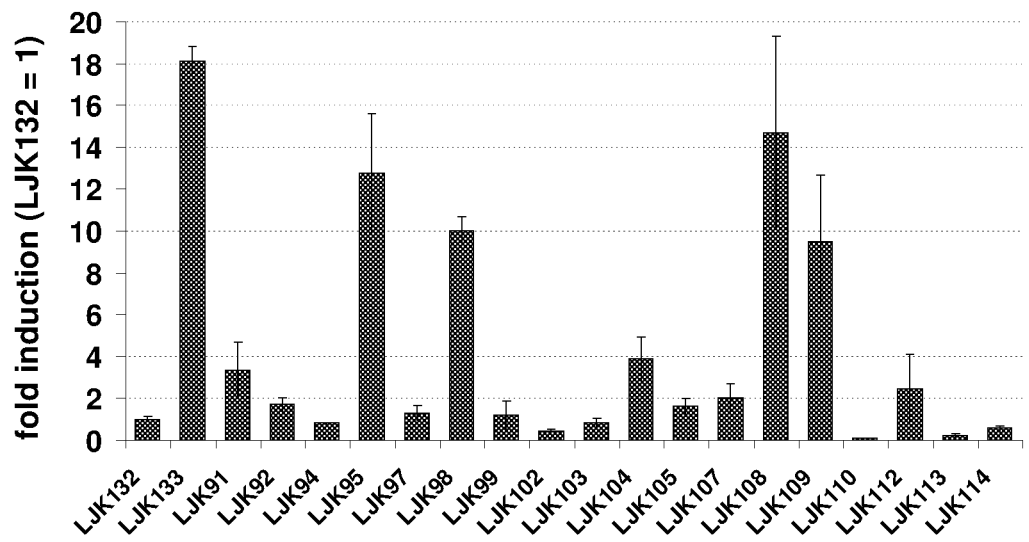
FIG. 1: Luciferase reporter gene expression analysis in transiently transformed *A. thaliana* leaf protoplasts of NEENA-less (LJK132) and NEENA-containing constructs (LJK91-LJK133) representing putative NEENA molecules deriving from constitutively expressed genes under the control of the p-AtNit1 promoter. Normalization was performed by cotransformation and analysis of the *Renilla* luciferase and expression values are shown in relation to the NEENA-less control construct (LJK132=1). Expression values are shown in relation to the NEENA-less control construct (LJK134=1).

A first embodiment of the invention comprises a method for production of a high expression constitutive promoter comprising functionally linking to a promoter one or more nucleic acid expression enhancing nucleic acid (NEENA) molecule comprising
  i) the nucleic acid molecule having a sequence as defined in any of SEQ ID NO: 1 to 19, preferably SEQ ID NO: 1 to 9, or
  ii) a nucleic acid molecule having a sequence with an identity of 80% or more to any of the sequences as defined by SEQ ID NO:1 to 19, preferably SEQ ID NO: 1 to 9, preferably, the identity is 85% or more, more preferably the identity is 90% or more, even more preferably, the identity is 95% or more, 96% or more, 97% or more, 98% or more or 99% or more, in the most preferred embodiment, the identity is 100% to any of the sequences as defined by SEQ ID NO:1 to 19, preferably SEQ ID NO: 1 to 9 or
  iii) a fragment of 100 or more consecutive bases, preferably 150 or more consecutive bases, more preferably 200 consecutive bases or more even more preferably 250 or more consecutive bases of a nucleic acid molecule of i) or ii) which has an expressing enhancing activity, for example 65% or more, preferably 70% or more, more preferably 75% or more, even more preferably 80% or more, 85% or more or 90% or more, in a most preferred embodiment it has 95% or more of the expression enhancing activity as the corresponding nucleic acid molecule having the sequence of any of the sequences as defined by SEQ ID NO:1 to 19, preferably SEQ ID NO: 1 to 9, or
  iv) a nucleic acid molecule which is the complement or reverse complement of any of the previously mentioned nucleic acid molecules under i) to iii), or
  v) a nucleic acid molecule which is obtainable by PCR using oligonucleotide primers described by SEQ ID NO: 20 to 57, preferably SEQ ID NO: 20/21; 26/27; 30/31; 38/39; 42/43; 44/45; 46/47; 50; 51 and 56/57 as shown in Table. 2 or
  vi) a nucleic acid molecule of 100 nucleotides or more, 150 nucleotides or more, 200 nucleotides or more or 250 nucleotides or more, hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by SEQ ID NO:1 to 19, preferably SEQ ID NO: 1 to 9 or the complement thereof. Preferably, said nucleic acid molecule is hybridizing under conditions equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by SEQ ID NO:1 to 19, preferably SEQ ID NO: 1 to 9 or the complement thereof, more preferably, said nucleic acid molecule is hybridizing under conditions equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by any of the sequences as defined by SEQ ID NO:1 to 19, preferably SEQ ID NO: 1 to 9 or the complement thereof.

In one embodiment, the one or more NEENA is heterologous to the promoter to which it is functionally linked.

As described above under v) the nucleic acid molecule obtainable by PCR using oligonucleotides as defined by SEQ IDs 20 to 57, preferably SEQ ID NO: 20/21; 26/27; 30/31; 38/39; 42/43; 44/45; 46/47; 50/51 and 56/57 as shown in Table 2 is obtainable for example from genomic DNA from *Arabidopsis* plants such as *A. thaliana* using the conditions as described in Example 1 below.

The skilled person is aware of variations in the temperature profile, cycle number and/or buffer composition or concentration to obtain the respective NEENA molecule. The specific combination of oligonucleotides to be used in the respective PCR reaction for obtaining a respective NEENA molecule is described in Table 2.

A person skilled in the art is aware of methods for rendering a unidirectional to a bidirectional promoter and of methods to use the complement or reverse complement of a promoter sequence for creating a promoter having the same promoter specificity as the original sequence.

Such methods are for example described for constitutive as well as inducible promoters by Xie et al. (2001) "Bidirectionalization of polar promoters in plants" nature biotechnology 19 pages 677-679. The authors describe that it is sufficient to add a minimal promoter to the 5' prime end of any given promoter to receive a promoter controlling expression in both directions with same promoter specificity. Hence a high expression promoter functionally linked to a NEENA as described above is functional in complement or reverse complement and therefore the NEENA is functional in complement or reverse complement too.

A constitutive promoter as used herein means a promoter expressed in substantially all plant tissues throughout substantially the entire life span of a plant or part thereof. A promoter expressed in substantially all plant tissues may also encompass promoters that are expressed in at least two of the main plant tissues such as leaf, stem and/or root and may or may not be expressed in some or all minor tissues or cells such as epidermis, stomata, trichome, flower, seed or meristematic tissue. In a preferred embodiment a constitutive promoter as meant herein is expressed at least in green tissues such as leaf and stem.

A promoter expressed throughout substantially the entire life span of a plant or part thereof may also encompass promoters that are expressed in young and developed tissue but may lack expression at specific time points in the lifespan of a plant or under specific conditions such as during germination and/or senescence or under biotic and/or abiotic stress conditions such as fungi or bacterial infection, drought, heat or cold. In a preferred embodiment a constitutive promoter expressed in substantially the entire lifespan of a plant is expressed at least in fully expanded tissue until onset of senescence.

In principal the NEENA may be functionally linked to any promoter such as tissue specific, inducible, developmental specific or constitutive promoters. The respective NEENA will lead to an enhanced expression of the heterologous nucleic acid under the control of the respective promoter to which the at least one NEENA is functionally linked to. The enhancement of expression of promoters other than constitutive promoters, for example tissue specific promoters, will render the specificity of these promoters. Expression of the nucleic acid under control of the respective promoter will be detectable in additional tissues or developmental stages the transcript of said nucleic acid had not been detected without the NEENA. Hence, tissue- or developmental specific or any other promoter may be rendered to a constitutive promoter by functionally linking at least one of the NEENA molecules as described above to said promoter. It is therefore another embodiment of the invention to provide a method for rendering the specificity of any given promoter functional in plant to a constitutive promoter by linking the respective promoter to a NEENA molecule comprising a sequence as described above under i) to vi).

Preferably, the one or more NEENA is functionally linked to any constitutive promoter and will enhance expression of the nucleic acid molecule under control of said promoter. Constitutive promoters to be used in any method of the invention may be derived from plants, for example monocotyledonous or dicotyledonous plants, from bacteria and/or viruses or may be synthetic promoters. Constitutive promoters to be used are for example the PcUbi-Promoter from *P. crispum* (WO 2003102198), the ZmUbi-Promoter from *Zea maize*, AtNit-promoter from the *A. thaliana* gene At3g44310 encoding nitrilase 1, the 34S-promoter from figwort mosaiv virus, the 35S-promoter from tobacco mosaic virus, the nos and ocs-promoter derived from Agrobacteria, the ScBV-promoter (U.S. Pat. No. 5,994,123), the SUPER-promoter (Lee et al. 2007, Plant. Phys.), the AtFNR-promoter from the *A. thaliana* gene At5g66190 encoding the ferredoxin NADH reductase, the ptxA promoter from *Pisum sativum* (WO2005085450), the AtTPT-promoter from the *A. thaliana* gene At5g46110 encoding the triose phosphate translocator, the bidirectional AtOASTL-promoter from the *A. thaliana* genes At4g14880 and At4g14890, the PRO0194 promoter from the *A. thaliana* gene At1g13440 encoding the glyceraldehyde-3-phosphate dehydrogenase, the PRO0162 promoter from the *A. thaliana* gene At3g52930 encoding the fructose-bis-phosphate aldolase, the AHAS-promoter (WO2008124495) or the CaffeoylCoA-MT promoter and the OsCP12 from rice (WO2006084868).

The high expression constitutive promoters of the invention functionally linked to a NEENA may be employed in any plant comprising for example moss, fern, gymnosperm or angiosperm, for example monocotyledonous or dicotyledonous plant. In a preferred embodiment said promoter of the invention functionally linked to a NEENA may be employed in monocotyledonous or dicotyledonous plants, preferably crop plant such as corn, soy, canola, cotton, potato, sugar beet, rice, wheat, sorghum, barley, musa, sugarcane, *miscanthus* and the like.

In a preferred embodiment of the invention, said promoter which is functionally linked to a NEENA may be employed in monocotyledonous crop plants such as corn, rice, wheat, sorghum, musa, *miscanthus*, sugarcane or barley. In an especially preferred embodiment the promoter functionally linked to a NEENA may be employed in dicotyledonous crop plants such as soy, canola, cotton, sugar beet or potato.

A high expressing constitutive promoter as used in the application means for example a promoter which is functionally linked to a NEENA causing enhanced constitutive expression of the promoter in a plant or part thereof wherein the accumulation of RNA or rate of synthesis of RNA derived from the nucleic acid molecule under the control of the respective promoter functionally linked to a NEENA is higher, preferably significantly higher than the expression caused by the same promoter lacking a NEENA of the invention. Preferably the amount of RNA of the respective nucleic acid and/or the rate of RNA synthesis and/or the RNA stability in a plant is increased 50% or more, for example 100% or more, preferably 200% or more, more preferably 5 fold or more, even more preferably 10 fold or more, most preferably 20 fold or more for example 50 fold compared to a control plant of same age grown under the same conditions comprising the same constitutive promoter the latter not being functionally linked to a NEENA of the invention.

When used herein, significantly higher refers to statistical significance the skilled person is aware how to determine, for example by applying statistical tests such as the t-test to the respective data sets.

Methods for detecting expression conferred by a promoter are known in the art. For example, the promoter may be functionally linked to a marker gene such as GUS, GFP or luciferase and the activity of the respective protein encoded by the respective marker gene may be determined in the plant or part thereof. As a representative example, the method for detecting luciferase is described in detail below. Other methods are for example measuring the steady state level or synthesis rate of RNA of the nucleic acid molecule controlled by the promoter by methods known in the art, for example Northern blot analysis, qPCR, run-on assays or other methods described in the art.

A skilled person is aware of various methods for functionally linking two or more nucleic acid molecules. Such methods may encompass restriction/ligation, ligase independent cloning, recombineering, recombination or synthesis. Other methods may be employed to functionally link two or more nucleic acid molecules.

A further embodiment of the present invention is a method for producing a plant or part thereof with, compared to a respective control plant or part thereof, enhanced constitutive expression of one or more nucleic acid molecule comprising the steps of introducing into the plant or part thereof one or more NEENA comprising a nucleic acid molecule as defined above under i) to vi) and functionally linking said one or more NEENA to a promoter, preferably a constitutive promoter and to a nucleic acid molecule being under the control of said promoter, preferably constitutive promoter, wherein the NEENA is heterologous to said nucleic acid molecule.

The NEENA may be heterologous to the nucleic acid molecule which is under the control of said promoter to which the NEENA is functionally linked or it may be heterologous to both the promoter and the nucleic acid molecule under the control of said promoter.

The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. For example, a NEENA of the invention is in its natural environment functionally linked to its native promoter, whereas in the present invention it is linked to another promoter which might be derived from the same organism, a different organism or might be a synthetic promoter such as the SUPER-promoter. It may also mean that the NEENA of the present invention is linked to its native promoter but the nucleic acid molecule under control of said promoter is heterologous to the promoter comprising its native NEENA. It is in addition to be understood that the promoter and/or the nucleic acid molecule under the control of said promoter functionally linked to a NEENA of the invention are heterologous to said NEENA as their sequence has been manipulated by for example mutation such as insertions, deletions and the forth so that the natural sequence of the promoter and/or the nucleic acid molecule under control of said promoter is modified and therefore have become heterologous to a NEENA of the invention. It may also be understood that the NEENA is heterologous to the nucleic acid to which it is functionally linked when the NEENA is functionally linked to its native promoter wherein the position of the NEENA in relation to said promoter is changed so that the promoter shows higher expression after such manipulation.

A plant exhibiting enhanced constitutive expression of a nucleic acid molecule as meant herein means a plant having a higher, preferably statistically significant higher constitutive expression of a nucleic acid molecule compared to a control plant grown under the same conditions without the respective NEENA functionally linked to the respective nucleic acid molecule. Such control plant may be a wild-type plant or a transgenic plant comprising the same promoter controlling the same gene as in the plant of the invention wherein the promoter is not linked to a NEENA of the invention.

Producing a plant as used herein comprises methods for stable transformation such as introducing a recombinant DNA construct into a plant or part thereof by means of *Agrobacterium* mediated transformation, protoplast transformation, particle bombardment or the like and optionally subsequent regeneration of a transgenic plant. It also comprises methods for transient transformation of a plant or part thereof such as viral infection or *Agrobacterium* infiltration. A skilled person is aware of further methods for stable and/or transient transformation of a plant or part thereof. Approaches such as breeding methods or protoplast fusion might also be employed for production of a plant of the invention and are covered herewith.

The method of the invention may be applied to any plant, for example gymnosperm or angiosperm, preferably angiosperm, for example dicotyledonous or monocotyledonous plants, preferably dicotyledonous plants. Preferred monocotyledonous plants are for example corn, wheat, rice, barley, sorghum, musa, sugarcane, *miscanthus* and brachypodium, especially preferred monocotyledonous plants are corn, wheat and rice. Preferred dicotyledonous plants are for example soy, rape seed, canola, linseed, cotton, potato, sugar beet, *tagetes* and *Arabidopsis*, especially preferred dicotyledonous plants are soy, rape seed, canola and potato In one embodiment of the invention, the methods as defined above are comprising the steps of
 a) introducing one or more NEENA comprising a nucleic acid molecule as defined above in i) to vi) into a plant or part thereof and
 b) integrating said one or more NEENA into the genome of said plant or part thereof whereby said one or more NEENA is functionally linked to an endogenous preferably constitutively expressed nucleic acid heterologous to said one or more NEENA and optionally
 c) regenerating a plant or part thereof comprising said one or more NEENA from said transformed cell.

The NEENA may be heterologous to the nucleic acid molecule which is under the control of said promoter to which the NEENA is functionally linked or it may be heterologous to both the promoter and the nucleic acid molecule under the control of said promoter.

The one or more NEENA molecule may be introduced into the plant or part thereof by means of particle bombardment, protoplast electroporation, virus infection, *Agrobacterium* mediated transformation or any other approach known in the art. The NEENA molecule may be introduced integrated for example into a plasmid or viral DNA or viral RNA. The NEENA molecule may also be comprised on a BAC, YAC or artificial chromosome prior to introduction into the plant or part of the plant. It may be also introduced as a linear nucleic acid molecule comprising the NEENA sequence wherein additional sequences may be present adjacent to the NEENA sequence on the nucleic acid molecule. These sequences neighboring the NEENA sequence may be from about 20 bp, for example 20 bp to several hundred base pairs, for example 100 bp or more and may facilitate integration into the genome for example by homologous recombination. Any other method for genome integration may be employed, be it targeted integration approaches, such as homologous recombination or random integration approaches, such as illegitimate recombination.

The endogenous preferably constitutively expressed nucleic acid to which the NEENA molecule may be functionally linked may be any nucleic acid, preferably any constitutively expressed nucleic acid molecule. The nucleic acid molecule may be a protein coding nucleic acid molecule or a non coding molecule such as antisense RNA, rRNA, tRNA, miRNA, ta-siRNA, siRNA, dsRNA, snRNA, snoRNA or any other noncoding RNA known in the art. The skilled person is aware of methods for identifying constitutively expressed nucleic acid molecules to which the method of the invention may preferably be applied for example by microarray chip hybridization, qPCR, Northern blot analysis, next generation sequencing etc.

A further way to perform the methods of the invention may be to
 a) provide an expression construct comprising one or more NEENA comprising a nucleic acid molecule as defined above in i) to vi) functionally linked to a promoter, preferably a constitutive promoter as defined above and to one or more nucleic acid molecule the latter being heterologous to said one or more NEENA and which is under the control of said promoter, preferably constitutive promoter and
 b) integrate said expression construct comprising said one or more NEENA into the genome of said plant or part thereof and optionally
 c) regenerate a plant or part thereof comprising said one or more expression construct from said transformed plant or part thereof.

The NEENA may be heterologous to the nucleic acid molecule which is under the control of said promoter to which the NEENA is functionally linked or it may be heterologous to both the promoter and the nucleic acid molecule under the control of said promoter.

The expression construct may be integrated into the genome of the respective plant with any method known in the art. The integration may be random using methods such as particle bombardment or *Agrobacterium* mediated transformation. In a preferred embodiment, the integration is via targeted integration for example by homologous recombination. The latter method would allow integrating the expression construct comprising a high expression promoter functionally linked to a NEENA into a favorable genome region. Favorable genome regions are for example genome regions known to comprise genes that are highly expressed for example in seeds and hence may increase expression derived from said expression construct compared to a genome region which shows no transcriptional activity.

In another preferred embodiment said one or more NEENA is functionally linked to a promoter, preferably constitutive promoter close to the transcription start site of said heterologous nucleic acid molecule.

Close to the transcription start site as meant herein comprises functionally linking one or more NEENA to a promoter, preferably a constitutive promoter 2500 bp or less, preferentially 2000 bp or less, more preferred 1500 bp or less, even more preferred 1000 bp or less and most preferred 500 bp or less away from the transcription start site of said heterologous nucleic acid molecule. It is to be understood that the NEENA may be integrated upstream or downstream in the respective distance from the transcription start site of the respective promoter. Hence, the one or more NEENA must not necessarily be included in the transcript of the respective heterologous nucleic acid under control of the preferably constitutive promoter the one or more NEENA is functionally linked to. Preferentially the one or more NEENA is integrated downstream of the transcription start site of the respective promoter, preferably constitutive promoter. The integration site downstream of the transcription start site may be in the 5' UTR, the 3' UTR, an exon or intron or it may replace an intron or partially or com-pletely the 5' UTR or 3' UTR of the heterologous nucleic acid under the control of the preferably constitutive promoter. Preferentially the one or more NEENA is integrated in the 5' UTR or an intron or the NEENA is replacing an intron or a part or the complete 5'UTR, most preferentially it is integrated in the 5'UTR of the respective heterologous nucleic acid.

A further embodiment of the invention comprises a recombinant expression construct comprising one or more NEENA comprising a nucleic acid molecule as defined above in i) to vi).

The recombinant expression construct may further comprise one or more promoter, preferably constitutive promoter to which the one or more NEENA is functionally linked and optionally one or more expressed nucleic acid molecule the latter being heterologous to said one or more NEENA.

The NEENA may be heterologous to the nucleic acid molecule which is under the control of said promoter to which the NEENA is functionally linked or it may be heterologous to both the promoter and the nucleic acid molecule under the control of said promoter.

The expression construct may comprise one ore more, for example two or more, for example 5 or more, such as 10 or more combinations of promoters, preferably constitutive promoters functionally linked to a NEENA and a nucleic acid molecule to be expressed heterologous to the respective NEENA. The expression construct may also comprise further promoters not comprising a NEENA functionally linked to nucleic acid molecules to be expressed homologous or heterologous to the respective promoter.

A recombinant expression vector comprising one or more recombinant expression construct as defined above is another embodiment of the invention. A multitude of expression vectors that may be used in the present invention are known to a skilled person. Methods for introducing such a vector comprising such an expression construct comprising for example a promoter functionally linked to a NEENA and optionally other elements such as a terminator into the genome of a plant and for recovering transgenic plants from a transformed cell are also well known in the art. Depending on the method used for the transformation of a plant or part thereof the entire vector might be integrated into the genome of said plant or part thereof or certain components of the vector might be integrated into the genome, such as, for example a T-DNA.

A transgenic plant or part thereof comprising one or more heterologous NEENA as defined above in i) to vi) is also enclosed in this invention. A NEENA is to be understood as being heterologous to the plant if it is synthetic, derived from another organism or the same organism but its natural genomic localization is rendered compared to a control plant, for example a wild type plant. It is to be understood, that a rendered genomic localization means the NEENA is located on another chromosome or on the same chromosome but 10 kb or more, for example 10 kb, preferably 5 kb or more, for example 5 kb, more preferably 1000 bp or more, for example 1000 bp, even more preferably 500 bp or more, for example 500 bp, especially preferably 100 bp or more, for example 100 bp, most preferably 10 bp or more, for example 10 bp dislocated from its natural genomic localization, for example in a wild type plant.

A transgenic cell or transgenic plant or part thereof comprising a recombinant expression vector as defined above or a recombinant expression construct as defined above is a further embodiment of the invention. The transgenic cell, transgenic plant or part thereof may be selected from the group consisting of bacteria, fungi, yeasts or plant, insect or mammalian cells or plants. Preferably the transgenic cells are bacteria, fungi, yeasts or plant cells. Preferred bacteria are Enterobacteria such as *E. coli* and bacteria of the genus Agrobacteria, for example *Agrobacterium tumefaciens* and *Agrobacterium rhizogenes*. Preferred plants are monocotyledonous or dicotyledonous plants for example monocotyledonous or dicotyledonous crop plants such as corn, soy, canola, cotton, potato, sugar beet, rice, wheat, sorghum, barley, *miscanthus*, musa, sugarcane and the like. Preferred crop plants are corn, rice, wheat, soy, canola, cotton or potato. Especially preferred dicotyledonous crop plants are soy, canola, cotton or potato.

Especially preferred monocotyledonous crop plants are corn, wheat and rice.

A transgenic cell culture, transgenic seed, parts or propagation material derived from a transgenic cell or plant or part thereof as defined above comprising said heterologous NEENA as defined above in i) to vi) or said recombinant expression construct or said recombinant vector as defined above are other embodiments of the invention.

Transgenic parts or propagation material as meant herein comprise all tissues and organs, for example leaf, stem and fruit as well as material that is useful for propagation and/or regeneration of plants such as cuttings, scions, layers, branches or shoots comprising the respective NEENA, recombinant expression construct or recombinant vector.

A further embodiment of the invention is the use of the NEENA as defined above in i) to vi) or the recombinant construct or recombinant vector as defined above for enhancing expression in plants or parts thereof.

Hence the application at hand provides seed-specific and/or seed-preferential gene expression enhancing nucleic acid molecules comprising one or more promoter, preferably seed-specific and/or seed preferential promoter functionally linked to one ore more NEENA. Additionally use of such gene expression enhancing nucleic acid molecules and expression constructs, expression vectors, transgenic plants or parts thereof and transgenic cells comprising such gene expression enhancing nucleic acid molecules are provided.

A use of a transgenic cell culture, transgenic seed, parts or propagation material derived from a transgenic cell or plant or part thereof as defined above for the production of foodstuffs, animal feeds, seeds, pharmaceuticals or fine chemicals is also enclosed in this invention.

Definitions

Abbreviations: NEENA—nucleic acid expression enhancing nucleic acid, GFP—green fluorescence protein, GUS—beta-Glucuronidase, BAP—6-benzylaminopurine; 2,4-D—2,4-dichlorophenoxyacetic acid; MS—Murashige and Skoog medium; NAA—1-naphtaleneacetic acid; MES, 2-(N-morpholino-ethanesulfonic acid, IAA indole acetic acid; Kan: Kanamycin sulfate; GA3—Gibberellic acid; Timentin™: ticarcillin disodium/clavulanate potassium, microl: Microliter.

It is to be understood that this invention is not limited to the particular methodology or protocols. It is also to be understood that the terminology used herein is for the purpose of de-scribing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows: Antiparallel: "Antiparallel" refers herein to two nucleotide sequences paired through hydrogen bonds between complementary base residues with phosphodiester bonds running in the 5'-3' direction in one nucleotide sequence and in the 3-5' direction in the other nucleotide sequence.

Antisense: The term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene mRNA molecule or single stranded genomic DNA through Wat-son-Crick base pairing) or that is complementary to a target DNA molecule such as, for example genomic DNA present in the host cell.

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Double-stranded RNA: A "double-stranded RNA" molecule or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule.

Endogenous: An "endogenous" nucleotide sequence refers to a nucleotide sequence, which is present in the genome of the untransformed plant cell.

Enhanced expression: "enhance" or "increase" the expression of a nucleic acid molecule in a plant cell are used equivalently herein and mean that the level of expression of the nucleic acid molecule in a plant, part of a plant or plant cell after applying a method of the present invention is higher than its expression in the plant, part of the plant or plant cell before applying the method, or compared to a reference plant lacking a recombinant nucleic acid molecule of the invention. For example, the reference plant is comprising the same construct which is only lacking the respective NEENA. The term "enhanced" or "increased" as used herein are synonymous and means herein higher, preferably significantly higher expression of the nucleic acid molecule to be expressed. As used herein, an "enhancement" or "increase" of the level of an agent such as a protein, mRNA or RNA means that the level is increased relative to a substantially identical plant, part of a plant or plant cell grown under substantially identical conditions, lacking a recombinant nucleic acid molecule of the invention, for example lacking the NEENA molecule, the recombinant construct or recombinant vector of the invetion. As used herein, "enhancement" or "increase" of the level of an agent, such as for example a preRNA, mRNA, rRNA, tRNA, snoRNA, snRNA expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a cell or organism lacking a recombinant nucleic acid molecule of the invention. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a plant or plant cell. Depending on the type of the induced protein product, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254). As one example for quantifying the activity of a protein, the detection of luciferase activity is described in the Examples below.

Expression: "Expression" refers to the biosynthesis of a gene product, preferably to the transcription and/or translation of a nucleotide sequence, for example an endogenous gene or a heterologous gene, in a cell. For example, in the case of a structural gene, expression in-volves transcription of the structural gene into mRNA and—optionally—the subsequent translation of mRNA into one or more polypeptides. In other cases, expression may refer only to the transcription of the DNA harboring an RNA molecule.

Expression construct: "Expression construct" as used herein mean a DNA sequence capable of directing expression of a particular nucleotide sequence in an appropriate part of a plant or plant cell, comprising a promoter functional in said part of a plant or plant cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example RNAa, siRNA, snoRNA, snRNA, microRNA, ta-siRNA or any other noncoding regulatory RNA, in the sense or antisense direction. The expression construct comprising the nucleotide sequence of interest may be chimeric, meaning that one or more of its components is heterologous with respect to one or more of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a constitutive promoter or of an inducible promoter, which initiates transcription only when the host cell is exposed to some particular external stimulus. In the case of a plant, the promoter can also be specific to a particular tissue or organ or stage of development.

Foreign: The term "foreign" refers to any nucleic acid molecule (e.g., gene sequence) which is introduced into the genome of a cell by experimental manipulations and may include sequences found in that cell so long as the introduced sequence contains some modification (e.g., a point mutation, the presence of a selectable marker gene, etc.) and is therefore distinct relative to the naturally-occurring sequence.

Functional linkage: The term "functional linkage" or "functionally linked" is to be understood as meaning, for example, the sequential arrangement of a regulatory element (e.g. a promoter) with a nucleic acid sequence to be expressed and, if appropriate, further regulatory elements (such as e.g., a terminator or a NEENA) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

Gene: The term "gene" refers to a region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating from experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

High expression constitutive promoter: A "high expression constitutive promoter" as used herein means a promoter causing constitutive expression in a plant or part thereof wherein the accumulation or rate of synthesis of RNA or stability of RNA derived from the nucleic acid molecule under the control of the respective promoter is higher, preferably significantly higher than the expression caused by the promoter lacking the NEENA of the invention. Preferably the amount of RNA and/or the rate of RNA synthesis and/or stability of RNA is increased 50% or more, for example 100% or more, preferably 200% or more, more preferably 5 fold or more, even more preferably 10 fold or more, most preferably 20 fold or more for example 50 fold relative to a constitutive promoter lacking a NEENA of the invention.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% \text{ G+C})$, when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage identity between the two sequences is a function of the number of identical positions shared by the sequences (i.e. % homology=number of identical positions/total number of positions×100). The terms "homology" and "identity" are thus to be considered as synonyms.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)).

Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

–p Program Name [String]; –d Database [String]; default=nr; –i Query File [File In]; default=stdin; –e Expectation value (E) [Real]; default=10.0; –m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; –o BLAST report Output File [File Out] Optional; default=stdout; –F Filter query sequence (DUST with blastn, SEG with others) [String]; default=T; –G Cost to open a gap (zero invokes default behavior) [Integer]; default=0; –E Cost to extend a gap (zero invokes default behavior) [Integer]; default=0; –X X dropoff value for gapped alignment (in bits) (zero invokes default behavior); blastn 30, megablast 20, tblastx 0, all others 15 [Integer]; default=0; –I Show GI's in deflines [T/F]; default=F; –q Penalty for a nucleotide mismatch (blastn only) [Integer]; default=–3; –r Reward for a nucleotide match (blastn only) [Integer]; default=1; –v Number of database sequences to show one-line descriptions for (V) [Integer]; default=500; –b Number of database sequence to show alignments for (B) [Integer]; default=250; –f Threshold for extending hits, default if zero; blastp 11, blastn 0, blastx 12, tblastn 13; tblastx 13, megablast 0 [Integer]; default=0; –g Perfom gapped alignment (not available with tblastx) [T/F]; default=T; –Q Query Genetic code to use [Integer]; default=1; –D DB Genetic code (for tblast[nx] only) [Integer]; default=1; –a Number of processors to use [Integer]; default=1; –O SeqAlign file [File Out] Optional; –J Believe the query defline [T/F]; default=F; –M Matrix [String]; default=BLOSUM62; –W Word size, default if zero (blastn 11, megablast 28, all others 3) [Integer]; default=0; –z Effective length of the database (use zero for the real size) [Real]; default=0; –K Number of best hits from a region to keep (off by default, if used a value of 100 is recommended) [Integer]; default=0; –P 0 for multiple hit, 1 for single hit [Integer]; default=0; –Y Effective length of the search space (use zero for the real size) [Real]; default=0; –S Query strands to search against database (for blast[nx], and tblastx); 3 is both, 1 is top, 2 is bottom [Integer]; default=3; –T Produce HTML output [T/F]; default=F; –I Restrict search of database to list of GI's [String] Optional; –U Use lower case filtering of FASTA sequence [T/F] Optional; default=F; –y X dropoff value for un-gapped extensions in bits (0.0 invokes default behavior); blastn 20, megablast 10, all others 7 [Real]; default=0.0; –Z X dropoff value for final gapped alignment in bits (0.0 invokes default behavior); blastn/megablast 50, tblastx 0, all others 25 [Integer]; default=0; –R PSI-TBLASTN checkpoint file [File In] Optional; –n MegaBlast search [T/F]; default=F; –L Location on query sequence [String] Optional; –A Multiple Hits window size, default if zero (blastn/megablast 0, all others 40 [Integer]; default=0; –w Frame shift penalty (OOF algorithm for blastx) [Integer]; default=0; –t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wisconsin, USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the identity is calculated on the complete length of the query sequence, for example SEQ ID NO:1.

Intron: refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5' or 3' untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG. Furthermore, in plants, two examples of AU-AC introns have been described: the fourteenth intron of the RecA-like protein gene and the seventh intron of the G5 gene from *Arabidopsis thaliana* are AT-AC introns. Pre-mRNAs containing introns have three short sequences that are—beside other sequences-essential for the intron to be accurately spliced. These sequences are the 5' splice-site, the 3' splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron is comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branch point. The branchpoint sequence is important in splicing and splice-site selection in plants. The branchpoint sequence is usually located 10-60 nucleotides upstream of the 3' splice site.

Isogenic: organisms (e.g., plants), which are genetically identical, except that they may differ by the presence or absence of a heterologous DNA sequence.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring polynucleotide or polypeptide present in a living plant is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Minimal Promoter: promoter elements, particularly a TATA element, that are inactive or that have greatly reduced promoter activity in the absence of upstream activation. In the presence of a suitable transcription factor, the minimal promoter functions to permit transcription.

NEENA: see "Nucleic acid expression enhancing nucleic acid".

Non-coding: The term "non-coding" refers to sequences of nucleic acid molecules that do not encode part or all of an expressed protein. Non-coding sequences include but are not limited to introns, enhancers, promoter regions, 3' untranslated regions, and 5' untranslated regions.

Nucleic acid expression enhancing nucleic acid (NEENA): The term "nucleic acid expression enhancing nucleic acid" refers to a sequence and/or a nucleic acid molecule of a specific sequence having the intrinsic property to enhance expression of a nucleic acid under the control of a promoter to which the NEENA is functionally linked. Unlike promoter sequences, the NEENA as such is not able to drive expression. In order to fulfill the function of enhancing expression of a nucleic acid molecule functionally linked to the NEENA, the NEENA itself has to be functionally linked to a promoter. In distinction to enhancer sequences known in the art, the NEENA is acting in cis but not in trans and has to be located close to the transcription start site of the nucleic acid to be expressed.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is re-placed by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodi-ester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxy-ribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomono-mers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "ex-tension," "protruding end," or "sticky end").

Plant: is generally understood as meaning any eukaryotic single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteri-dophytes such as ferns, horsetail and club mosses; gymnosperms such as conifers, cycads, ginkgo and Gnetatae; algae such as Chlorophyceae, Phaeophpyceae, Rhodophyceae, Myxophyceae, Xanthophyceae, Bacillarophyceae (diatoms), and Euglenophyceae. Preferred are plants which are used for food or feed purpose such as the families of the Leguminosae such as pea, alfalfa and soya; Gramineae such as rice, maize, wheat, barley, sorghum, millet, rye, triticale, or oats; the family of the Umbelliferae, especially the genus *Daucus*, very especially the species *carota* (carrot) and *Apium*, very especially the species *Graveolens* dulce (celery) and many others; the family of the Solanaceae, especially the genus *Lycopersicon*, very especially the species *esculentum* (tomato) and the genus *Solanum*, very especially the species *tuberosum* (potato) and *melongena* (egg plant), and many others (such as tobacco); and the genus Capsicum, very especially the species *annuum* (peppers) and many others; the family of the Leguminosae, especially the genus Glycine, very especially the species max (soybean), alfalfa, pea, lucerne, beans or peanut and many others; and the family of the Cruciferae (*Brassica*-cae), especially the genus *Brassica*, very especially the species *napus* (oil seed rape), campestris (beet), *oleracea* cv Tastie (cabbage), *oleracea* cv Snowball Y (cauliflower) and *oleracea* cv Emperor (broccoli); and of the genus *Arabidopsis*, very especially the species *thaliana* and many others; the family of the Compositae, especially the genus *Lactuca*, very especially the species *sativa* (lettuce) and many others; the family of the Asteraceae such as sunflower, *Tagetes*, lettuce or Calendula and many other; the family of the Cucurbitaceae such as melon, pumpkin/squash or zucchini, and linseed. Further preferred are cotton, sugar cane, hemp, flax, chillies, and the various tree, nut and wine species.

Polypeptide: The terms "polypeptide", "peptide", "oligo-peptide", "polypeptide", "gene product", "expression product" and "protein" are used interchangeably herein to refer to a polymer or oligomer of consecutive amino acid residues.

Pre-protein: Protein, which is normally targeted to a cellular organelle, such as a chloroplast, and still comprising its transit peptide.

Primary transcript: The term "primary transcript" as used herein refers to a premature RNA transcript of a gene. A "primary transcript" for example still comprises introns and/or is not yet comprising a polyA tail or a cap structure and/or is missing other modifications necessary for its correct function as transcript such as for example trimming or editing.

Promoter: The terms "promoter", or "promoter sequence" are equivalents and as used herein, refer to a DNA sequence which when ligated to a nucleotide sequence of interest is capable of controlling the transcription of the nucleotide sequence of interest into RNA. Such promoters can for example be found in the following public databases gras-sius.org/grasspromdb.html, mendel.cs.rhul.ac.uk/ mendel.php?topic=plantprom, ppdb.gene.nagoya-u.ac.jp/ cgi-bin/index.cgi. Promoters listed there may be addressed with the methods of the invention and are herewith included by reference. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. Said promoter comprises for example the at least 10 kb, for example 5 kb or 2 kb proximal to the transcription start site. It may also comprise the at least 1500 bp proximal to the transcriptional start site, preferably the at least 1000 bp, more preferably the at least 500 bp, even more preferably the at least 400 bp, the at least 300 bp, the at least 200 bp or the at least 100 bp. In a further preferred embodiment, the promoter comprises the at least 50 bp proximal to the transcription start site, for example, at least 25 bp. The promoter does not comprise exon and/or intron regions or 5' untranslated regions. The promoter may for example be heterologous or homologous to the respective plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). A plant specific promoter is a promoter suitable for regulating expression in a plant. It may be derived from a plant but also from plant pathogens or it might be a synthetic promoter designed by man. If a promoter is an inducible promoter, then the rate of transcription increases in response to an inducing agent. Also, the promoter may be regulated in a tissue-specific or tissue preferred manner such that it is only or predominantly active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining, GFP protein or immunohistochemical staining. The term "constitutive" when made in reference to a promoter or the expression derived from a promoter means that the promoter is capable of directing transcription of an operably linked nucleic acid molecule in the absence of a stimulus (e.g., heat shock, chemicals, light, etc.) in the majority of plant tissues and cells throughout substantially the entire lifespan of a plant or part of a plant. Typically, constitutive promoters are capable of directing expression of a transgene in substantially any cell and any tissue.

Promoter specificity: The term "specificity" when referring to a promoter means the pattern of expression conferred by the respective promoter. The specificity describes the tissues and/or developmental status of a plant or part thereof, in which the promoter is conferring expression of the nucleic acid molecule under the control of the respective promoter. Specificity of a promoter may also comprise the environmental conditions, under which the promoter may be activated or down-regulated such as induction or repression by biological or environmental stresses such as cold, drought, wounding or infection.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated.

A purified nucleic acid sequence may be an isolated nucleic acid sequence.

Recombinant: The term "recombinant" with respect to nucleic acid molecules refers to nucleic acid molecules produced by recombinant DNA techniques. Recombinant nucleic acid molecules may also comprise molecules, which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

Sense: The term "sense" is understood to mean a nucleic acid molecule having a sequence which is complementary or identical to a target sequence, for example a sequence which binds to a protein transcription factor and which is involved in the expression of a given gene. According to a preferred embodiment, the nucleic acid molecule comprises a gene of interest and elements allowing the expression of the said gene of interest.

Significant increase or decrease: An increase or decrease, for example in enzymatic activity or in gene expression, that is larger than the margin of error inherent in the measurement technique, preferably an increase or decrease by about 2-fold or greater of the activity of the control enzyme or expression in the control cell, more preferably an increase or decrease by about 5-fold or greater, and most preferably an increase or decrease by about 10-fold or greater.

Small nucleic acid molecules: "small nucleic acid molecules" are understood as molecules consisting of nucleic acids or derivatives thereof such as RNA or DNA. They may be double-stranded or single-stranded and are between about 15 and about 30 bp, for example between 15 and 30 bp, more preferred between about 19 and about 26 bp, for example between 19 and 26 bp, even more preferred between about 20 and about 25 bp for example between 20 and 25 bp. In a especially preferred embodiment the oligonucleotides are between about 21 and about 24 bp, for example between 21 and 24 bp. In a most preferred embodiment, the small nucleic acid molecules are about 21 bp and about 24 bp, for example 21 bp and 24 bp.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the chromosomal DNA of the host cell. Another type of vector is an episomal vector, i.e., a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences recognized by any RNA polymerase, including mitochondrial RNA polymerase, RNA pol I, RNA pol II, and RNA pol Ill. These vectors can be used to transcribe the desired RNA molecule in the cell according to this invention. A plant transformation vector is to be understood as a vector suitable in the process of plant transformation.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

EXAMPLES

Chemicals and Common Methods

Unless indicated otherwise, cloning procedures carried out for the purposes of the present invention including restriction digest, agarose gel electrophoresis, purification of nucleic acids, Ligation of nucleic acids, transformation, selection and cultivation of bacterial cells were performed as described (Sambrook et al., 1989). Sequence analyses of recombinant DNA were performed with a laser fluorescence DNA sequencer (Applied Biosystems, Foster City, CA, USA) using the Sanger technology (Sanger et al., 1977). Unless described otherwise, chemicals and reagents were obtained from Sigma Aldrich (Sigma Aldrich, St. Louis, USA), from Promega (Madison, WI, USA), Duchefa (Haarlem, The Netherlands) or Invitrogen (Carlsbad, CA, USA). Restriction endonucleases were from New England Biolabs (Ipswich, MA, USA) or Roche Diagnostics GmbH (Penzberg, Germany). Oligonucleotides were synthesized by Eurofins MWG Operon (Ebersberg, Germany).

Example 1: Identification of Nucleic Acid Expression Enhancing Nucleic Acids (NEENA) from Genes with Constitutive Expression 1.1 Identification of NEENA Molecules from *A. thaliana* Genes Using publicly available genomic DNA sequences (e.g. ncbi.nlm.nih.gov/genomes/PLANTS/PlantList.html) and transcript expression data (e.g. weigelworld.org/resources/microarray/AtGenExpress/), a set of 18 potential NEENA candidates deriving from *Arabidopsis thaliana* transcripts from highly expressing constitutive genes were selected for detailed analyses. In addition, a putative NEENA molecule deriving from parsley was also included in the analysis. The candidates were named as follows:

TABLE 1 constitutive NEENA candidates (NEENAc).

| NEENA name | Locus | Annotation | SEQ ID NO |
|---|---|---|---|
| NEENAc24 | | *Petroselinum crispum* gene Pcubi4-2 for polyubiquitin | 1 |
| NEENAc17 | At2g47170 | ADP-ribosylation factor 1 (ARF1) | 2 |
| NEENAc5 | At1g56070 | elongation factor 2, putative/EF-2, putative | 3 |
| NEENAc18 | At5g54760 | eukaryotic translation initiation factor SUI1, putative | 4 |
| NEENAc7 | At4g02890 | polyubiquitin (UBQ14) | 5 |
| NEENAc13 | At3g03780 | AtMS2 (*Arabidopsis thaliana* methionine synthase 2) | 6 |

TABLE 1-continued constitutive NEENA candidates (NEENAc).

| NEENA name | Locus | Annotation | SEQ ID NO |
|---|---|---|---|
| NEENAc1 | At5g60390 | elongation factor 1-alpha/EF-1-alpha | 7 |
| NEENAc21 | At1g14400 | ubiquitin-conjugating enzyme 1 (UBC1) | 8 |
| NEENAc16 | At4g14880 | cysteine synthase/O-acetylserine (thiol)-lyase/O-acetylserine sulfhydrylase (OAS1) | 9 |
| NEENAc2 | At4g27960 | ubiquitin-conjugating enzyme E2-17 kDa 9 (UBC9) | 10 |
| NEENAc14 | At1g64230 | ubiquitin-conjugating enzyme, putative | 11 |
| NEENAc4 | At2g37270 | 40S ribosomal protein S5 (RPS5A) | 12 |
| NEENAc6 | At4g05050 | polyubiquitin (UBQ11) | 13 |
| NEENAc8 | At1g43170 | 60S ribosomal protein L3 (RPL3A) | 14 |
| NEENAc11 | At1g01100 | 60S acidic ribosomal protein P1 (RPP1A) | 15 |
| NEENAc12 | At5g04800 | 40S ribosomal protein S17 (RPS17D) | 16 |
| NEENAc19 | At4g34110 | polyadenylate-binding protein 2 (PABP2) | 17 |
| NEENAc22 | At2g34770 | fatty acid hydroxylase (FAH1) (anticipated IME effect) | 18 |
| NEENAc23 | At5g17920 | cobalamin-independent methionine synthase (CIMS) | 19 |

1.2 Isolation of the NEENA Candidates

Genomic DNA was extracted from *A. thaliana* green tissue using the Qiagen DNeasy Plant Mini Kit (Qiagen, Hilden, Germany). For the putative NEENA molecule with the SEQ ID NO1, DNA of the vector construct 1bxPcUbi4-2GUS (WO 2003102198) was used. Genomic DNA fragments containing putative NEENA molecules were isolated by conventional polymerase chain reaction (PCR). The polymerase chain reaction comprised 19 sets of primers (Table 2). Primers were designed on the basis of the *A. thaliana* genome sequence with a multitude of NEENA candidates. The nucleotide sequence of the vector construct bxPcUbi4-2GUS (WO 2003102198) was used for the design of primers (SEQ ID N56 and 57) for amplification of the NEENA candidate with SEQ ID NO1 (Table 2). The polymerase chain reaction followed the protocol outlined by Phusion High Fidelity DNA Polymerase (Cat No F-540L, New England Biolabs, Ipswich, MA, USA). The isolated DNA was used as template DNA in a PCR amplification using the following primers:

TABLE 2

Primer sequences

| Primer name | Sequence | SEQ ID NO | PCR yielding SEQ ID NO |
|---|---|---|---|
| NEENAc1_for | tttatggtaccagccgcaagactcctttcagattct | 20 | 7 |
| NEENAc1_rev | aaattccatggtagctgtcaaaacaaaaacaaaaatcga | 21 | |
| NEENAc2_for | aaaaaggtacctcgaagaaccaaaaccaaaaacgtga | 22 | 10 |
| NEENAc2_rev | tttttccatggttatttatccaaaatcccacgatccaaattcca | 23 | |
| NEENAc4_for | tttttggtaccgatccctacttctctcgacact | 24 | 12 |
| NEENAc4_rev | ttttaccatggtgactggaggatcaatagaagat | 25 | |
| NEENAc5_for | tttttggtacctttctctcgttctcatctttctctct | 26 | 3 |
| NEENAc5_rev | taatagatatctttgtcaaacttttgattgtcacct | 27 | |
| NEENAc6_for | tataaggtaccaaatcaatctctcaaatctctca | 28 | 13 |
| NEENAc6_rev | tttatccatggtctgttaatcagaaaaaccgagat | 29 | |
| NEENAc7_for | tatatggtaccaaatcgttcttctcaaatctctca | 30 | 5 |
| NEENAc7_rev | ttataccatggtctgtaattcacaaaaaactgaga | 31 | |
| NEENAc8_for | tttttggtacctcatcgttggagcttagaagc | 32 | 14 |
| NEENAc8_rev | tttttccatggtcttcttcttcttcttctacatca | 33 | |
| NEENAc11_for | tatatggtaccaaagcattttcgatcttactcttaggt | 34 | 15 |
| NEENAc11_rev | tttttccatggttttttatcctgaaacgattca | 35 | |
| NEENAc12_for | tttttggtaccttttgacgccgccgcttcttcttct | 36 | 16 |
| NEENAc12-rev | tttttccatggtcttcagttacctgtgtgacttacct | 37 | |
| NEENAc13_for | tttaaggtacccatctctcatctccactcttct | 38 | 6 |
| NEENAc13_rev | tttttgatatcttttgtttgttttttgttttttttact | 39 | |
| NEENAc14_for | ttataggtaccaagtgaatcgtcaaaaccgagtt | 40 | 11 |
| NEENAc14_rev | tttttccatggttctcaaccaaaaaaaaactcct | 41 | |
| NEENAc16_for | tttttggtaccacgattcgggtcaaggttattga | 42 | 9 |
| NEENAc16_rev | tttttccatggtgattcaagctcactgcttaaattcaca | 43 | |
| NEENAc17_for | tttttggtaccttagatctcgtgccgtcgtgcga | 44 | 2 |
| NEENAc17_rev | tttttccatggtttgatcaagcctgttcaca | 45 | |
| NEENAc18_for | aaaaaggtacctcatcagatcttcaaaaccccaa | 46 | 4 |
| NEENAc18_rev | aaaaaccatggtgatttgagggtagtactaaccgggaa | 47 | |
| NEENAc19_for | ttttaggtaccatacgttaacttcaccaatcccaa | 48 | 17 |
| NEENAc19_rev | tttttccatggttaattaatgcagtgctttgtggtcgatgga | 49 | |
| NEENAc21_for | tttttcccgggatctttacctcaacaacgagat | 50 | 8 |
| NEENAc21_rev | tttttccatggttatcctccttctttctaataaacaaaaccca | 51 | |
| NEENAc22_for | tttttggtacctctcttccgtctcgagtcgctgaga | 52 | 18 |
| NEENAc22_rev | tttttccatggtttgcagaccttttactgat | 53 | |

TABLE 2-continued

Primer sequences

| Primer name | Sequence | SEQ ID NO | PCR yielding SEQ ID NO |
|---|---|---|---|
| NEENAc23_for | tttttggtaccttccttcctcc tctccgattcttcct | 54 | 19 |
| NEENAc23_rev | tttttccatggttattgatttt cttttactgcat | 55 | |
| NEENAc24_for | tttttggtaccttaagaaatc ctctcttctcct | 56 | 1 |
| NEENAc24_rev | tttttccatggtctgcacata cataacatatca | 57 | |

Amplification during the PCR was carried out with the following composition (50 microl):

3.00 microl A. thaliana genomic DNA (50 ng/microl genomic DNA, 5 ng/microl vector construct)

10.00 microl 5×Phusion HF Buffer 4.00 microl dNTP (2.5 mM)

2.50 microl for Primer (10 microM)

2.50 microl rev Primer (10 microM)

0.50 microl Phusion HF DNA Polymerase (2U/microl)

A touch-down approach was employed for the PCR with the following parameters: 98,000 for 30 sec (1 cycle), 98,000 for 30 sec, 56.0° C. for 30 sec and 72,000 for 60 sec (4 cycles), 4 additional cycles each for 54.0° C., 51,000 and 49,000 annealing temperature, followed by 20 cycles with 98,000 for 30 sec, 46,000 for 30 sec and 72,000 for 60 sec (4 cycles) and 72,000 for 5 min. The amplification products was loaded on a 2% (w/v) agarose gel and separated at 80V. The PCR products were excised from the gel and purified with the Qiagen Gel Extraction Kit (Qiagen, Hilden, Germany). Following a DNA restriction digest with KpnI (10 U/microl) and NcoI (10 U/microl) or EcoRV (10U/microl) restriction endonuclease, the digested products were again purified with the Qiagen Gel Extraction Kit (Qiagen, Hilden, Germany).

1.3 Vector Construction 1.3.1 Generation of Vector Constructs with Potential NEENA Molecules Using the Multisite Gateway System (Invitrogen, Carlsbad, CA, USA), the promoter::NEENA::reporter-gene cassettes were assembled into binary constructs for plant transformation. The A. thaliana p-AtNit1 (At3g44310, GenBank X86454; WO03008596, with the prefix p-denoting promoter) promoter was used in the reporter gene construct, and firefly luciferase (Promega, Madison, WI, USA) was utilized as reporter protein for quantitatively determining the expression enhancing effects of the putative NEENA molecules to be analyzed.

The pENTR/A vector holding the p-AtNit1 promoter was cloned via site specific recombination (BP-reaction) between the pDONR/A vector and p-AtNit1 amplification products with primers p-AtNit1—for and p-AtNit1-rev (Table 3) on genomic DNA (see above) with site specific recombination sites at either end according to the manufacturers manual (Invitrogen, Carlsbad, CA, USA). Positive pENTR/A clones underwent sequence analysis to ensure correctness of the p-AtNit1 promoter.

TABLE 3

Primer sequences (p-AtNit1)

| Primer name | Sequence | SEQ ID NO. |
|---|---|---|
| p-AtNit1-for | ggggacaactttgtatagaaaagttg tcgagaccagatgttttacacttga | 58 |
| p-AtNit1-rev | ggggactgcttttttgtacaaacttg gacactcagagacttgagagaagca | 59 |

An ENTR/B vector containing the firefly luciferase coding sequence (Promega, Madison, WI, USA) followed by the t-nos nopalin synthase transcriptional terminator (Genbank V00087) was generated. NEENA candidate PCR fragments (see above) were cloned separately up-stream of the firefly luciferase coding sequence using KpnI and NcoI or EcoRV restriction enzymes. The resulting pENTR/B vectors are summarized in table 4, with promoter molecules having the prefix p-, coding sequences having the prefix c-, and terminator molecules having the prefix t-.

TABLE 4 all pENTR/B vectors plus and minus NEENA candidates

| pENTR/B vector | Composition of the partial expression cassette SEQ ID NO::reporter gene::terminator |
|---|---|
| LJK1 | MCS::c-LUC::t-nos |
| LJK4 | SEQ ID NO1::c-LUC::t-nos |
| LJK40 | SEQ ID NO7::c-LUC::t-nos |
| LJK41 | SEQ ID NO10::c-LUC::t-nos |
| LJK43 | SEQ ID NO12::c-LUC::t-nos |
| LJK44 | SEQ ID NO3::c-LUC::t-nos |
| LJK46 | SEQ ID NO13::c-LUC::t-nos |
| LJK47 | SEQ ID NO5::c-LUC::t-nos |
| LJK48 | SEQ ID NO14::c-LUC::t-nos |
| LJK51 | SEQ ID NO15::c-LUC::t-nos |
| LJK52 | SEQ ID NO16::c-LUC::t-nos |
| LJK53 | SEQ ID NO6::c-LUC::t-nos |
| LJK54 | SEQ ID NO11::c-LUC::t-nos |
| LJK56 | SEQ ID NO9::c-LUC::t-nos |
| LJK57 | SEQ ID NO2::c-LUC::t-nos |
| LJK58 | SEQ ID NO4::c-LUC::t-nos |
| LJK59 | SEQ ID NO17::c-LUC::t-nos |
| LJK61 | SEQ ID NO8::c-LUC::t-nos |
| LJK62 | SEQ ID NO18::c-LUC::t-nos |
| LJK63 | SEQ ID NO19::c-LUC::t-nos |

The pENTR/C vector was constructed by introduction of a multiple cloning site (SEQ ID NO60) via KpnI and Hind/II restriction sites. By performing a site specific recombination (LR-reaction), the created pENTR/A, pENTR/B and pENTR/C were combined with the pSUN destination vector (pSUN derivative) according to the manufacturers (Invitrogen, Carlsbad, CA, USA) Multisite Gateway manual. The reactions yielded 1 binary vector with p-AtNit1 promoter, the firefly luciferase coding sequence c-LUC and the t-nos terminator and 19 vectors harboring SEQ ID NO1, NO2, NO3, NO4, NO5, NO6, NO7, NO8, NO9, NO1b, NO11, NO12, NO13, NO14, NO15, NO16, NO17, NO18 and NO19 immediately upstream of the firefly luciferase coding sequence (Table 5), for which the combination with SEQ ID NO1 is given exemplary (SEQ ID NO61). Except for varying SEQ ID NO2 to NO19, the nucleotide sequence is identical in all vectors (Table 5). The resulting plant transformation vectors are summarized in table 5:

TABLE 5

Plant expression vectors for *A. thaliana* transformation

| plant expression vector | Composition of the expression cassette Promoter::SEQ ID NO::reporter gene::terminator | SEQ ID NO |
|---|---|---|
| LJK132 | p-AtNit1::-::c-LUC::t-nos | |
| LJK133 | p-AtNit1::SEQ ID NO1:c-LUC::t-nos | 61 |
| LJK91 | p-AtNit1::SEQ ID NO7::c-LUC::t-nos | |
| LJK92 | p-AtNit1::SEQ ID NO10::c-LUC::t-nos | |
| LJK94 | p-AtNit1::SEQ ID NO12::c-LUC::t-nos | |
| LJK95 | p-AtNit1::SEQ ID NO3::c-LUC::t-nos | |
| LJK97 | p-AtNit1::SEQ ID NO13::c-LUC::t-nos | |
| LJK98 | p-AtNit1::SEQ ID NO5::c-LUC::t-nos | |
| LJK99 | p-AtNit1::SEQ ID NO14::c-LUC::t-nos | |
| LJK102 | p-AtNit1::SEQ ID NO15::c-LUC::t-nos | |
| LJK103 | p-AtNit1::SEQ ID NO16::c-LUC::t-nos | |
| LJK104 | p-AtNit1::SEQ ID NO6::c-LUC::t-nos | |
| LJK105 | p-AtNit1::SEQ ID NO11::c-LUC::t-nos | |
| LJK107 | p-AtNit1::SEQ ID NO9::c-LUC::t-nos | |
| LJK108 | p-AtNit1::SEQ ID NO2::c-LUC::t-nos | |
| LJK109 | p-AtNit1::SEQ ID NO4::c-LUC::t-nos | |
| LJK110 | p-AtNit1::SEQ ID NO17::c-LUC::t-nos | |
| LJK112 | p-AtNit1::SEQ ID NO8::c-LUC::t-nos | |
| LJK113 | p-AtNit1::SEQ ID NO18::c-LUC::t-nos | |
| LJK114 | p-AtNit1::SEQ ID NO19::c-LUC::t-nos | |

The resulting vectors were subsequently used to transform *A. thaliana* leaf protoplasts transiently.

1.3.2 *Renilla* Luciferase Control Construct

*Renilla* luciferase cDNA was amplified using 10 ng of the plasmid pRL-null from Promega (Madison, WI, USA) as DNA template and primers R-LUC_for and R-LUC_rev (Table 6) with PCR parameters as described above.

TABLE 6

Primer sequences (c-RLUC)

| Primer name | Sequence | SEQ ID NO |
|---|---|---|
| RLUC_for | aaaaaggtaccatgacttcgaaagttt atgatc | 62 |
| RLUC_rev | aaattgagctcttattgttcatttttg agaactc | 63 |

Following a DNA restriction digest with Kpn/(10 U/microl) and Sac/(10 U/microl) restriction endonuclease, the digested products were again purified with the Qiagen Gel Extraction Kit (Qiagen, Hilden, Germany).

The fragment was cloned into a ENTR/B vector containing the nopaline synthase constitutive promoter p-nos (Genbank V00087) followed by the t-nos nopalin synthase transcriptional terminator (Genbank V00087) via Kpn/and Sac/ restriction sites, yielding a pENTR/B clone, which underwent sequence analysis to ensure correctness of the *Renilla* luciferase containing expression cassette.

Example 2: Screening for NEENA Candidate Molecules Enhancing Gene Expression in *A. thaliana* Transiently Transformed Leaf Protoplasts This example illustrates that only selected NEENA molecules are capable of enhancing gene expression. 2.1 Isolation and transient transformation of *A. thaliana* leaf protoplasts Isolation and transient transformation of *A. thaliana* leaf protoplasts was amended according to established protocols (Damm and Willmitzer, 1988; Damm et al., 1989) Leaves of 4 week old *A. thaliana* plants were cut in small pieces using a razor blade and transferred to a solution with 1.5% Cellulase R10 (Duchefa, Haarlem, The Netherlands), 0.3% Mazerozyme R10 (Duchefa, Haarlem, The Netherlands), 400 mM Mannitol, 20 mM KCl, 20 mM MES, 10 mM $CaCl_2$, pH5.7 and incubated over night at room temperature. Due to a variability of transient *A. thaliana* leaf protoplast transformation, *Renilla* luciferase (Dual-Luciferase© Reporter Assay System, Promega, Madison, WI, USA) was used to normalize the firefly luciferase expression capabilities of the constructs above. The transient transformation of the NEENA-less (LJK132) and each NEENA-containing vector construct (LJK66-LJK114) was performed in triplicate with 6 microg plasmid DNA, which was mixed with 25 microg of *Renilla* luciferase containing construct prior to transformation, using PEG (poly ethylene glycol) and $1 \times 10^4$ protoplasts.

2.2 Dual Luciferase Reporter Gene Assay

Transfected *A. thaliana* protoplasts were collected by centrifugation at 100 g and frozen in liquid nitrogen after removal of supernatant. The assay for detection of firefly and *Renilla* luciferase activity in the transfected cells was performed according to the manufacturers (Promega, Madison, WI, USA) Dual-Luciferase Reporter Assay System manual. Luminescence measurements were conducted in a MicroLumat Plus LB96V (Berthold Technologies, Bad Wildbad, Germany) recorded after addition of the luciferase substrates. Instrument readings of both luciferase recordings were normalized by generating a ratio between firefly luciferase and *Renilla* luciferase. The data from three experiments were averaged for each construct and based on these average expression values, fold change values were calculated to assess the impact of presence of a putative NEENA over reporter gene constructs lacking the respective putative NEENA. In comparison to p-AtNit1 promoter-only NEENA-less reporter gene constructs, the 19 tested NEENA candidates containing constructs showed negative as well as positive effects, ranging from 0.1-fold to 18.1-fold induction in firefly Luciferase activity (FIG. 1). In total, 9 putative NEENA molecules comprising sequences with SEQ ID NO1, NO2, NO3, NO4, NO5, NO6, NO7, NO8 and NO9 conferred a greater than 2-fold increase in gene expression based on luciferase reporter gene activity compared to the NEENA-less promoter-only reporter gene construct (FIG. 1) and hence are functional NEENA molecules. Since a number of the tested NEENA candidate molecules have marginal or even negative effects on the enhancement of gene expression, not all putative NEENA molecules are mediating a common stimulatory effect, but rather that the selected NEENA sequences convey significant enhancement of gene expression (SEQ ID NO. 1 to 9).

Example 3: Test of NEENA Molecules for Enhancement of Gene Expression in Oilseed Rape Plants This example illustrates that NEENA molecules can be used across species to enhance gene expression in all tissues tested compared to a NEENA-less promoter-only approach.

NEENA molecules mediating the strongest enhancement in gene expression in the pre-screening (cp. Example 2, SEQ ID NO1, NO2, NO3, NO4 and NO5) were selected for determining the enhancement on gene expression levels in transgenic oilseed rape plants.

3.1 Vector Construction for *B. napus* Plant Transformation

For transformation of oilseed rape plants, reporter gene expression cassettes without and with gene expression control molecules (SEQ IDs NO1-NO5) were combined with a gene expression cassette carrying a selectable marker gene for detecting transgenic plant lines within a pENTR/C vector. By performing a site specific recombination (LR-reaction), as previously described (see above, 1.4), the pENTR/A, pENTR/B and the pENTR/C carrying the selectable marker cassette were combined with the pSUN destination vector according to the manufacturers (Invitrogen, Carlsbad, CA, USA) Multisite Gateway manual. The reactions yielded one binary vector with p-AtNit1 promoter, the firefly luciferase coding sequence c-LUC, the t-nos terminator and the selectable marker cassette as well as 5 vectors harboring SEQ ID NO1, NO2, NO3, NO4, and NO5 immediately upstream of the firefly luciferase coding sequence (Table 7), for which the combination with SEQ ID NO1 is given exemplary (SEQ ID NO64). Except for varying SEQ ID NO2 to NO5, the nucleotide sequence is identical in all vectors (Table 7). The resulting plant transformation vectors are summarized in table 7:

TABLE 7

Plant expression vectors for B. napus transformation

| plant expression vector | Composition of the expression cassette Promoter::SEQ ID NO::reporter gene::terminator | SEQ ID NO |
| --- | --- | --- |
| LJK138 | p-AtNit1::-::c-LUC::t-nos | |
| LJK139 | p-AtNit1::SEQ ID NO1::c-LUC::t-nos | 64 |
| LJK141 | p-AtNit1::SEQ ID NO3::c-LUC::t-nos | |
| LJK142 | p-AtNit1::SEQ ID NO5::c-LUC::t-nos | |
| LJK143 | p-AtNit1::SEQ ID NO2::c-LUC::t-nos | |
| LJK144 | p-AtNit1::SEQ ID NO4::c-LUC::t-nos | |

3.2 Generation of transgenic rapeseed plants (amended protocol according to Moloney et al., 1992, Plant Cell Reports, 8: 238-242).

In preparation for the generation of transgenic rapeseed plants, the binary vectors were transformed into *Agrobacterium tumefaciens* C58C1:pGV2260 (Deblaere et al., 1985, Nucl. Acids. Res. 13: 4777-4788). A 1:50 dilution of an overnight culture of Agrobacteria harboring the respective binary construct was grown in Murashige-Skoog Medium (Murashige and Skoog, 1962, Physiol. Plant 15, 473) supplemented with 3% saccharose (3MS-Medium). For the transformation of rapeseed plants, petioles or hypocotyledons of sterile plants were incubated with a 1:50 *Agrobacterium* solution for 5-10 minutes followed by a three-day co-incubation in darkness at 25° C. on 3 MS. Medium supplemented with 0.8% bactoagar. After three days, the explants were transferred to MS-medium containing 500 mg/l Claforan (Cefotaxime-Sodium), 100 nM Imazetapyr, 20 microM Benzylaminopurin (BAP) and 1.6 g/l Glucose in a 16 h light/8 h darkness light regime, which was repeated in weekly periods. Growing shoots were transferred to MS-Medium containing 2% saccharose, 250 mg/l Claforan and 0.8% Bacto-agar. After 3 weeks, the growth hormone 2-Indolbutyl acid was added to the medium to promote root formation. Shoots were transferred to soil following root development, grown for two weeks in a growth chamber and grown to maturity in greenhouse conditions.

3.3 Plant Analysis

Tissue samples were collected from the generated transgenic plants from leaves, flowers and siliques, stored in a freezer at −80° C. subjected to a Luciferase reporter gene assay (amended protocol after Ow et al., 1986). After grinding the frozen tissue samples were resuspended in 800 microl of buffer I (0.1 M Phosphate buffer pH7.8, 1 mM DTT (Sigma Aldrich, St. Louis, MO, USA), 0.05% Tween 20 (Sigma Aldrich, St. Louis, MO, USA)) followed by centrifugation at 10 000 g for 10 min. 75 microl of the aqueous supernatant were transferred to 96-well plates. After addition of 25 microl of buffer II (80 mM gycine-glycyl (Carl Roth, Karlsruhe, Germany), 40 mM MgSO4 (Duchefa, Haarlem, The Netherlands), 60 mM ATP (Sigma Aldrich, St. Louis, MO, USA), pH 7.8) and D-Luciferin to a final concentration of 0.5 mM (Cat No: L-8220, BioSynth, Staad, Switzerland), luminescence was recorded in a MicroLumat Plus LB96V (Berthold Technologies, Bad Wildbad, Germany) yielding the unit relative light unit RLU per minute (RLU/min).

In order to normalize the luciferase activity between samples, the protein concentration was determined in the aqueous supernatant in parallel to the luciferase activity (adapted from Bradford, 1976, Anal. Biochem. 72, 248). 5 microl of the aqueous cell extract in buffer I were mixed with 250 microl of Bradford reagent (Sigma Aldrich, St. Louis, MO, USA), incubated for 10 min at room temperature. Absorption was determined at 595 nm in a plate reader (Thermo Electron Corporation, Multiskan Ascent 354). The total protein amounts in the samples were calculated with a previously generated standard concentration curve. Values resulting from a ratio of RLU/min and mg protein/ml sample were averaged for transgenic plants harboring identical constructs and fold change values were calculated to assess the impact of NEENA molecule presence over NEENA-less reporter gene constructs.

3.4 NEENA Sequences Mediate Strong Enhancement of Gene Expression in Oilseed Rape Plants For assessing the potential of enhancing gene expression of selected NEENA molecules (SEQ ID NO:1, 2, 3, 4 and 5) in oilseed rape plants, leafs, flowers and siliques harboring seeds of plants having identical developmental stages and which were grown under equal growth conditions were collected. The samples were taken from individual transgenic oilseed rape plant lines harboring either a promoter-only reporter gene construct or Luciferase reporter gene constructs containing a NEENA (SEQ ID NO1, 2, 3, 4 and 5). 10 seeds were collected from each transgenic event, processed and analyzed for Luciferase activity as described above (Example 3.3).

Figure 2:
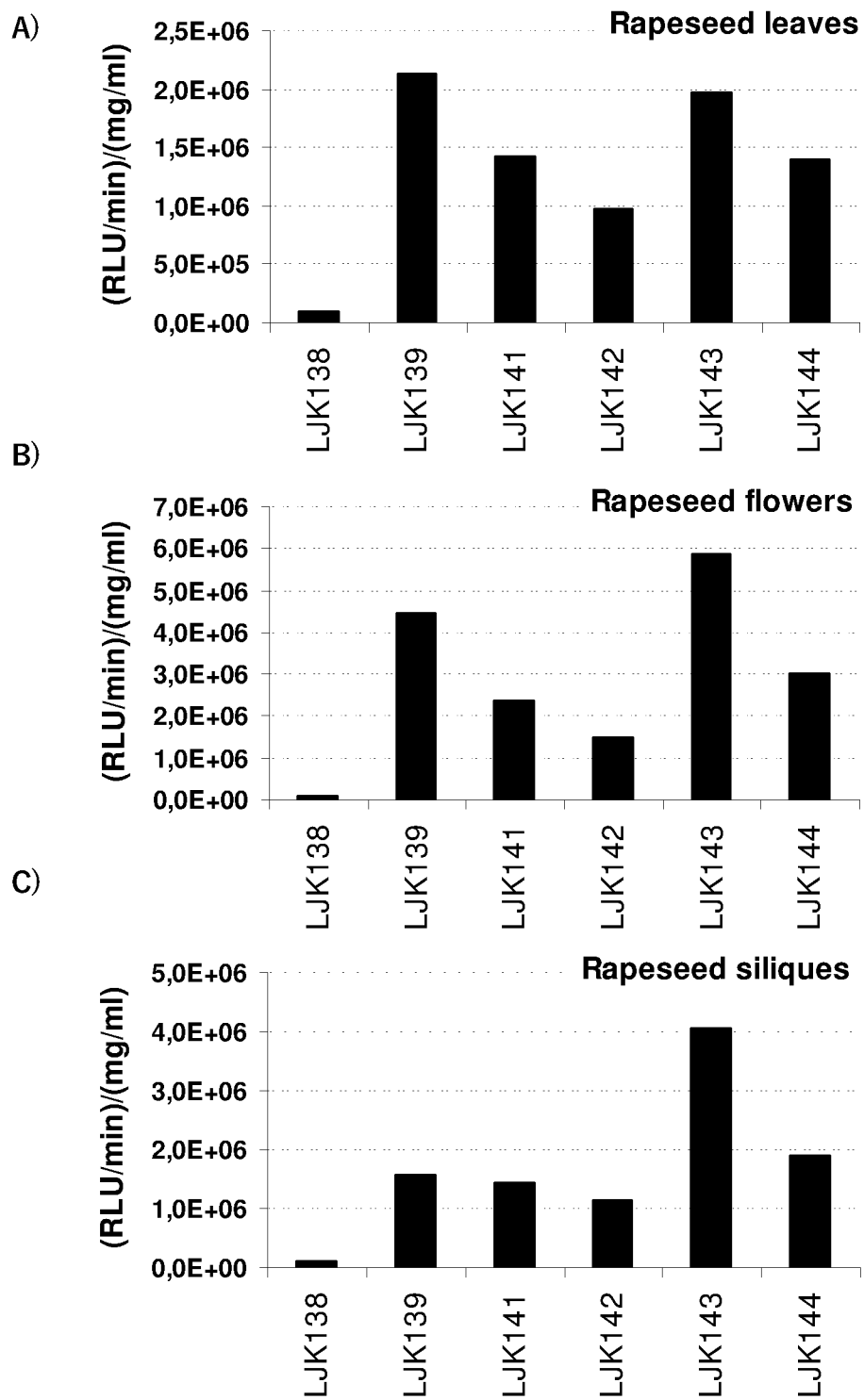
FIG. 2: Bar graph of the luciferase reporter gene activity shown as relative light units (RLU) of independent transgenic oilseed rape plant lines harboring NEENA-less (LJK138) or NEENA-containing reporter gene constructs representing NEENA molecules from constitutively expressed genes (LJK139-LJK144) under the control of the p-AtNit1 promoter and after normalization against the protein content of each sample (averaged values, tissues of 20 independent transgenic plants analyzed). A) leaf tissue, B) flowers, C) siliques

In comparison to the constitutive p-AtNit1 promoter-only NEENA-less reporter gene construct, the five tested NEENA molecules all mediated strong enhancements in gene expression in leaf tissues (FIG. 2, a). Comparable enhancement of gene expression mediated by NEENAs (SEQ ID NO1, 2, 3, 4 and 5) was detected in oilseed rape flowers and siliques including seeds (FIG. 2, b and c).

Example 4: Analysis of Constitutive Enhancement of Gene Expression in Soybean Plants This example illustrates that NEENA molecules can be used in a wide array of plant species and across species borders from different plant families to enhance gene expression in all tissues compared to a NEENA-less promoter-only approach.

NEENA sequence molecules mediating the strongest enhancement in gene expression in the pre-screening (cp. Example 2, SEQ ID NO1, 2, 3, 4 and 5) were selected for determining the enhancement on gene expression levels in transgenic soybean plants. Plant expression vectors LJK138, LJK139, LJK141, LJK142, LJK143 and LJK144 (cp. example 3.1) were used for stable soybean transformation.

4.1 Generation of transgenic soybean plants (amended protocol according to WO2005/121345; Olhoft et al., 2007).

Soybean seed germination, propagation, *A. rhizogenes* and axillary meristem explant preparation, and inoculations were done as previously described (WO2005/121345; Olhoft et al., 2007) with the exception that the constructs LJK138, LJK139, LJK141, LJK142, LJK143 and LJK144 (cp. example 3.1) each contained a mutated AHAS gene driven by the parsley ubiquitin promoter PcUbi4-2, mediating tolerance to imidazolinone herbicides for selection.

4.2 NEENA Sequences Mediate Strong Enhancement of Gene Expression in Soybean Plants Tissue samples were collected from the generated transgenic plants from leaves, flowers and seeds. The tissue samples were processed and analyzed as described above (cp. example 3.3)

Figure 3:
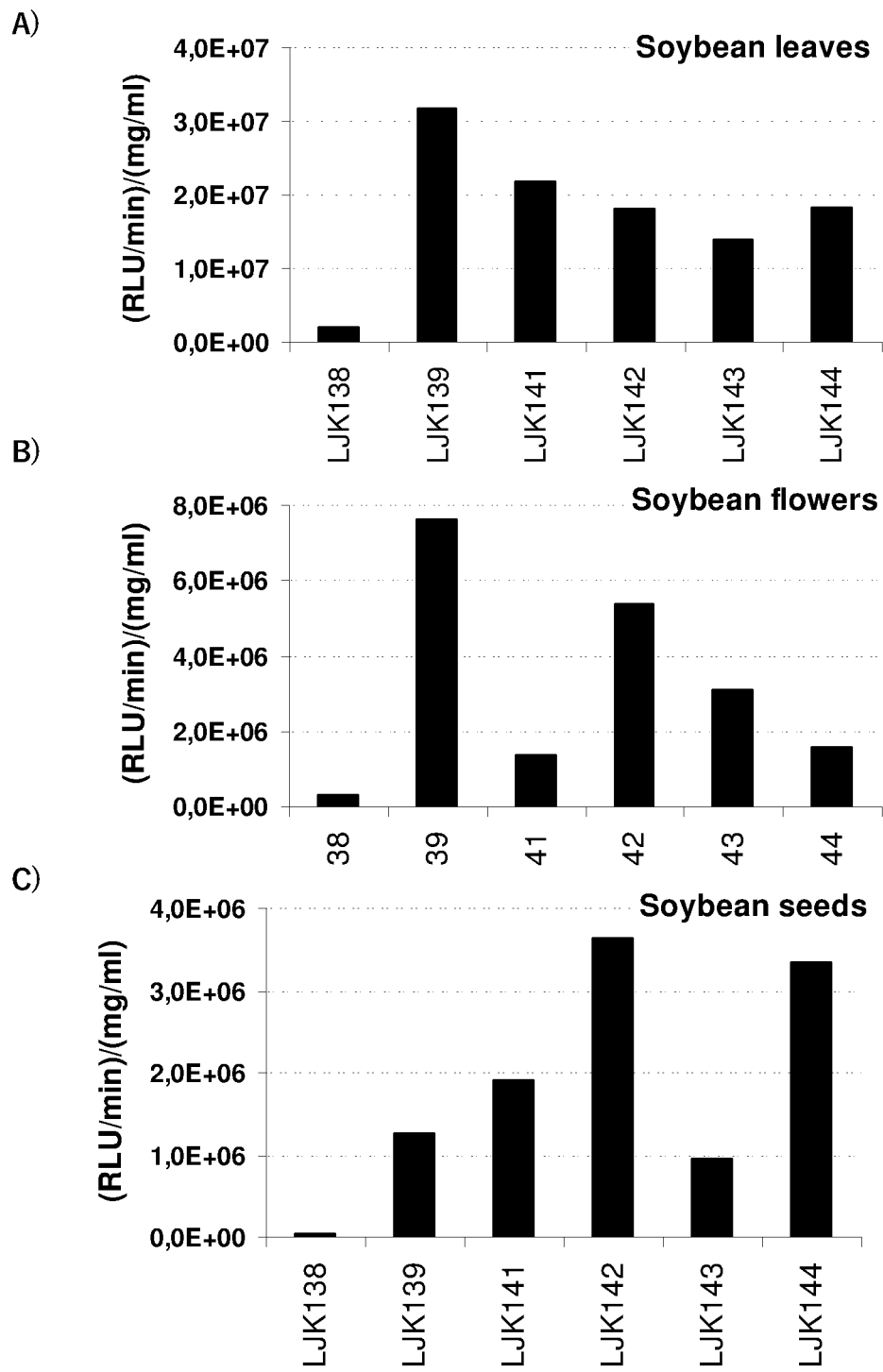
FIG. 3: Bar graph of the luciferase reporter gene activity shown as relative light units (RLU) of independent transgenic soybean plant lines harboring NEENA-less (LJK138) or NEENA-containing reporter gene constructs representing NEENA molecules from constitutively expressed genes (LJK139-LJK144) under the control of the p-AtNit1 promoter and after normalization against the protein content of each sample (averaged values, tissues of 10 independent transgenic plants analyzed). A) leaf tissue, B) flowers, C) seeds

In comparison to the constitutive p-AtNit1 promoter-only NEENA-less reporter gene construct, the five tested NEENA molecules all mediated strong enhancements in gene expression in leaves (FIG. 3a). Comparable enhancement of gene expression mediated by NEENAs (SEQ ID NO1 to NO5) was detected in soybean flowers and siliques (FIG. 3, b and c).

Example 5: Analysis of NEENA Activity in Monocotyledonous Plants

This example describes the analysis of NEENA sequences with SEQ ID NO 1, 2, 3, 4 and 5 in monocotyledonous plants.

5.1 Vector Construction

For analyzing NEENA sequences with SEQ ID NO 1, 2, 3, 4 and 5 in monocotyledonous plants, a pUC-based expression vector harboring an expression cassette composed of the NEENA-less, constitutive monocotyledonous promoter p-Ubi from *Z. mais* is combined with a coding sequence of the beta-Glucuronidase (GUS) gene followed by the nopaline synthase (NOS) transcriptional terminator. Genomic DNA is extracted from *A. thaliana* green tissue using the Qiagen DNeasy Plant Mini Kit (Qiagen, Hilden, Germany). Genomic DNA fragments containing NEENA molecules are isolated by conventional polymerase chain reaction (PCR). Primers are designed on the basis of the *A. thaliana* genome sequence with a multitude of NEENA candidates. The reaction comprises 5 sets of primers (Table 8) and follows the protocol outlined by Phusion High Fidelity DNA Polymerase (Cat No F-540L, New England Biolabs, Ipswich, MA, USA) using the following primers:

TABLE 8

Primer sequences

| Primer name | Sequence | SEQ ID NO | PCR yielding SEQ ID NO |
|---|---|---|---|
| NEENAc5_forII | tttttggcgcgcctttctct cgttctcatctttctctct | 65 | 3 |
| NEENAc5_revII | taataggcgcgcctttgtca aacttttgattgtcacct | 66 | |
| NEENAc7_forII | tatatggcgcgccaaatcgt tctttcaaatctctca | 67 | 5 |
| NEENAc7_revII | ttataggcgcgcctctgtaa ttcacaaaaaactgaga | 68 | |
| NEENAc17_forII | tttttggcgcgccttagatc tcgtgccgtcgtgcga | 69 | 2 |

TABLE 8-continued

Primer sequences

| Primer name | Sequence | SEQ ID NO | PCR yielding SEQ ID NO |
|---|---|---|---|
| NEENAc17_revII | tttttggcgcgcctttgatc aagcctgttcaca | 70 | |
| NEENAc18_forII | aaaaaggcgcgcctcatcag atcttcaaaacccaa | 71 | 4 |
| NEENAc18_revII | aaaaaggcgcgcctgatttg agggtagtactaaccgggaa | 72 | |
| NEENAc24_forII | tttttggcgcgccttaaga aatcctctcttctcct | 73 | 1 |
| NEENAc24_revII | tttttggcgcgccctgcac atacataacatatca | 74 | |

Amplification during the PCR and purification of the amplification products is carried out as detailed above (example 1.2). Following a DNA restriction digest with AscI (10 U/microl) restriction endonuclease, the digested products are purified with the Qiagen Gel Extraction Kit (Qiagen, Hilden, Germany).

NEENA PCR fragments (see above) are cloned separately upstream of the beta-Glucuronidase coding sequence using AscI restriction sites. The reaction yields one binary vector with the p-Ubi promoter, the beta-Glucuronidase coding sequence c-GUS and the t-nos terminator and five vectors harboring SEQ ID NO1, NO2, NO3, NO4 and NO5, immediately upstream of the beta-Glucuronidase coding sequence (Table 9), for which the combination with SEQ ID NO1 is given exemplary (SEQ ID NO75). Except for varying SEQ ID NO2 to NO5, the nucleotide sequence is identical in all vectors (Table 9). The resulting vectors are summarized in table 9, with promoter molecules having the prefix p-, coding sequences having the prefix c-, and terminator molecules having the prefix t-.

TABLE 9

Plant expression vectors

| plant expression vector | Composition of the expression cassette Promoter::SEQ ID NO::reporter gene::terminator | SEQ ID NO |
|---|---|---|
| RTP2940 | p-Ubi::-::c-GUS::t-nos | |
| LJK361 | p-Ubi::SEQ ID NO1::c-GUS::t-nos | 75 |
| LJK362 | p-Ubi::SEQ ID NO2::c-GUS::t-nos | |
| LJK363 | p-Ubi::SEQ ID NO3::c-GUS::t-nos | |
| LJK364 | p-Ubi::SEQ ID NO4::c-GUS::t-nos | |
| LJK365 | p-Ubi::SEQ ID NO5::c-GUS::t-nos | |

The resulting vectors are used to analyze NEENA molecules in experiments outlined below (Example 5.2).

5.2 Analysis of NEENA Molecules Enhancing Gene Expression in Monocotyledonous Plant Tissues These experiments are performed by bombardment of monocotyledonous plant tissues or culture cells (Example 6.2.1), by PEG-mediated (or similar methodology) introduction of DNA to plant protoplasts (Example 6.2.2), or by *Agrobacterium*-mediated transformation (Example 6.3.3). The target tissue for these experiments can be plant tissues (e.g. leaf tissue), cultured plant cells (e.g. maize Black Mexican Sweetcorn (BMS), or plant embryos for *Agrobacterium* protocols.

5.2.1 Transient Assay Using Microprojectile Bombardment

The plasmid constructs are isolated using Qiagen plasmid kit (cat #12143). DNA is precipitated onto 0.6 microM gold particles (Bio-Rad cat #165-2262) according to the protocol described by Sanford et al. (1993) (Optimizing the biolistic process for different biological applications. Methods in Enzymology, 217: 483-509) and accelerated onto target tissues (e.g. two week old maize leaves, BMS cultured cells, etc.) using a PDS-1000/He system device (Bio-Rad). All DNA precipitation and bombardment steps are performed under sterile conditions at room temperature. Black Mexican Sweet corn (BMS) suspension cultured cells are propagated in BMS cell culture liquid medium [Murashige and Skoog (MS) salts (4.3 g/L), 3% (w/v) sucrose, myo-inositol (100 mg/L), 3 mg/L 2,4-dichlorophenoxyacetic acid (2,4-D), casein hydrolysate (1 g/L), thiamine (10 mg/L) and L-proline (1.15 g/L), pH 5.8]. Every week 10 mL of a culture of stationary cells are transferred to 40 mL of fresh medium and cultured on a rotary shaker operated at 110 rpm at 27° C. in a 250 mL flask.

60 mg of gold particles in a siliconized Eppendorf tube are resuspended in 100% ethanol followed by centrifugation for 30 seconds. The pellet is rinsed once in 100% ethanol and twice in sterile water with centrifugation after each wash. The pellet is finally resuspended in 1 mL sterile 50% glycerol. The gold suspension is then divided into 50 microL aliquots and stored at 4° C. The following reagents are added to one aliquot: 5 microL of 1 microg/microL total DNA, 50 microL 2.5 M $CaCl_2$, 20 microL 0.1 M spermidine, free base. The DNA solution is vortexed for 1 minute and placed at −80° C. for 3 min followed by centrifugation for 10 seconds. The supernatant is removed. The pellet is carefully resuspended in 1 mL 100% ethanol by flicking the tube followed by centrifugation for 10 seconds. The supernatant is removed and the pellet is carefully resuspended in 50 microL of 100% ethanol and placed at −80° C. until used (30 min to 4 hr prior to bombardment). If gold aggregates are visible in the solution the tubes are sonicated for one second in a water bath sonicator just prior to use.

For bombardment, two-week-old maize leaves are cut into pieces approximately 1 cm in length and placed ad-axial side up on osmotic induction medium M-N6-702 [N6 salts (3.96 g/L), 3% (w/v) sucrose, 1.5 mg/L 2,4-dichlorophenoxyacetic acid (2,4-D), casein hydrolysate (100 mg/L), and L-proline (2.9 g/L), MS vitamin stock solution (1 mL/L), 0.2 M mannitol, 0.2 M sorbitol, pH 5.8]. The pieces are incubated for 1-2 hours.

In the case of BMS cultured cells, one-week-old suspension cells are pelleted at 1000 g in a Beckman/Coulter Avanti J25 centrifuge and the supernatant is discarded. Cells are placed onto round ash-free No 42 Whatman filters as a 1/16 inch thick layer using a spatula. The filter papers holding the plant materials are placed on osmotic induction media at 27° C. in darkness for 1-2 hours prior to bombardment. Just before bombardment the filters are removed from the medium and placed onto on a stack of sterile filter paper to allow the calli surface to partially dry.

Each plate is shot with 6 microL of gold-DNA solution twice, at 1,800 psi for the leaf materials and at 1,100 psi for the BMS cultured cells. To keep the position of plant materials, a sterilized wire mesh screen is laid on top of the sample. Following bombardment, the filters holding the samples are transferred onto M-N6-702 medium lacking mannitol and sorbitol and incubated for 2 days in darkness at 27° C. prior to transient assays.

The transient transformation via microprojectile bombardment of other monocotyledonous plants are carried out using, for example, a technique described in Wang et al., 1988 (Transient expression of foreign genes in rice, wheat and soybean cells following particle bombardment. Plant Molecular Biology, 11 (4), 433-439), Christou, 1997 (Rice transformation: bombardment. Plant Mol Biol. 35 (1-2)).

Expression levels of the expressed genes in the constructs described above (example 5.1) are determined by GUS staining, quantification of luminescence/fluorescence, RT-PCR and protein abundance (detection by specific antibodies) using the protocols in the art. GUS staining is done by incubating the plant materials in GUS solution [100 mM NaHPO4, 10 mM EDTA, 0.05% Triton X100, 0.025% X-Gluc solution (5-bromo-4-chloro-3-indolyl-beta-D-glucuronic acid dissolved in DMSO), 10% methanol, pH 7.0] at 37° C. for 16-24 hours. Plant tissues are vacuum-infiltrated 2 times for 15 minutes to aid even staining. Analyses of luciferase activities are performed as described above (example 2 and 3.3).

In comparison to the constitutive p-Ubi promoter-only NEENA-less reporter gene construct, the NEENA molecules all mediate strong enhancement in gene expression in these assays.

5.2.2 Transient Assay Using Protoplasts

Isolation of protoplasts is conducted by following the protocol developed by Sheen (1990) (Metabolic Repression of Transcription in Higher Plants. The Plant Cell 2 (10), 1027-1038). Maize seedlings are kept in the dark at 25° C. for 10 days and illuminated for 20 hours before protoplast preparation. The middle part of the leaves are cut to 0.5 mm strips (about 6 cm in length) and incubated in an enzyme solution containing 1% (w/v) cellulose RS, 0.1% (w/v) macerozyme R10 (both from Yakult Honsha, Nishinomiya, Japan), 0.6 M mannitol, 10 mM Mes (pH 5.7), 1 mM $CaCl_2$, 1 mM $MgCl_2$, 10 mM beta-mercaptoethanol, and 0.1% BSA (w/v) for 3 hr at 23° C. followed by gentle shaking at 80 rpm for 10 min to release protoplasts. Protoplasts are collected by centrifugation at 100×g for 2 min, washed once in cold 0.6 M mannitol solution, centrifuged, and resuspended in cold 0.6 M mannitol ($2×10^6$/mL).

A total of 50 microg plasmid DNA in a total volume of 100 microL sterile water is added into 0.5 mL of a suspension of maize protoplasts ($1×10^6$ cells/mL) and mixed gently. 0.5 mL PEG solution (40% PEG 4,000, 100 mM $CaNO_3$, 0.5 mannitol) is added and pre-warmed at 70° C. with gentle shaking followed by addition of 4.5 mL MM solution (0.6 M mannitol, 15 mM $MgCl_2$, and 0.1% MES). This mixture is incubated for 15 minutes at room temperature. The protoplasts are washed twice by pelleting at 600 rpm for 5 min and resuspending in 1.0 mL of MMB solution [0.6 M mannitol, 4 mM Mes (pH 5.7), and brome mosaic virus (BMV) salts (optional)] and incubated in the dark at 25° C. for 48 hr. After the final wash step, the protoplasts are collected in 3 mL MMB medium, and incubated in the dark at 25° C. for 48 hr.

The transient transformation of protoplasts of other monocotyledonous plants are carried out using, for example, a technique described in Hodges et al., 1991 (Transformation and regeneration of rice protoplasts. Biotechnology in agriculture No. 6, Rice Biotechnology. Inter-national Rice Research Institute, ISBN: 0-85198-712-5) or Lee et al., 1990 (Transient gene expression in wheat (*Triticum aestivum*) protoplasts. Biotechnology in agriculture and forest-ry 13—Wheat. Springer Verlag, ISBN-10: 3540518096).

Expression levels of the expressed genes in the constructs described above (Example 5.1) are determined by GUS staining, quantification of luminescence/fluorescence, RT-PCR or protein abundance (detection by specific antibodies) using the protocols in the art. GUS staining is done by incubating the plant materials in GUS solution [100 mM NaHPO4, 10 mM EDTA, 0.05% Triton X100, 0.025% X-Gluc solution (5-bromo-4-chloro-3-indolyl-beta-D-glucuronic acid dissolved in DMSO), 10% methanol, pH 7.0] at 37° C. for 16-24 hours. Analyses of luciferase activities are performed as described above (Example 2 and 3.3). In comparison to the constitutive p-Ubi promoter-only NEENA-less reporter gene construct, the NEENA molecules mediate strong enhancement in gene expression in these assays.

5.2.3 Transformation and Regeneration of Monocotyledonous Crop Plants

The *Agrobacterium*-mediated plant transformation using standard transformation and regeneration techniques may also be carried out for the purposes of transforming crop plants (Gelvin and Schilperoort, 1995, Plant Molecular Biology Manual, 2nd Edition, Dordrecht: Kluwer Academic Publ. ISBN 0-7923-2731-4; Glick and Thompson (1993) Methods in Plant Molecular Biology and Biotechnology, Boca Raton: CRC Press, ISBN 0-8493-5164-2). The transformation of maize or other monocotyledonous plants can be carried out using, for example, a technique described in U.S. Pat. No. 5,591,616. The transformation of plants using particle bombardment, polyethylene glycol-mediated DNA uptake or via the silicon carbonate fiber technique is described, for example, by Freeling & Walbot (1993) "The maize handbook" ISBN 3-540-97826-7, Springer Verlag New York).

Expression levels of the expressed genes in the constructs described above (Example 5.1) are determined by GUS staining, quantification of luminescence or fluorescence, RT-PCR, protein abundance (detection by specific antibodies) using the protocols in the art. GUS staining is done by incubating the plant materials in GUS solution [100 mM NaHPO4, 10 mM EDTA, 0.05% Triton X100, 0.025% X-Gluc solution (5-bromo-4-chloro-3-indolyl-beta-D-glucuronic acid dissolved in DMSO), 10% methanol, pH 7.0] at 37° C. for 16-24 hours. Plant tissues are vacuum-infiltrated 2 times for 15 minutes to aid even staining. Analyses of luciferase activities are performed as described above (Examples 2 and 3.3).

In comparison to the constitutive p-Ubi promoter-only NEENA-less reporter gene constructs, the NEENA molecules mediate strong enhancement in gene expression in plants.

Example 6: Quantitative Analysis of NEENA Activity in Corn Plants

This example describes the analysis of NEENA sequences with SEQ ID NO 1 and 2 in corn plants.

6.1 Vector Construction

For analyzing NEENA sequences with SEQ ID NO 1 and 2 in monocotyledonous plants quantitatively, a pUC-based expression vector harboring an expression cassette composed of the NEENA-less, constitutive monocotyledonous promoter p-Ubi from *Z. mais* was combined with a coding sequence of the firefly luciferase (LUC) gene (Promega, Madison, WI, USA) followed by the nopaline synthase (NOS) transcriptional terminator. Genomic DNA was extracted from *A. thaliana* green tissue using the Qiagen DNeasy Plant Mini Kit (Qiagen, Hilden, Germany). Genomic DNA fragments containing NEENA molecules were isolated by conventional polymerase chain reaction (PCR). Primers were designed on the basis of the *A. thaliana* genome sequence with a multitude of NEENA candidates. The reaction comprised 2 sets of primers (Table 10) and followed the protocol outlined by Phusion High Fidelity DNA Polymerase (Cat No F-540L, New England Biolabs, Ipswich, MA, USA) using the following primers:

TABLE 10

Primer sequences

| Primer name | Sequence | SEQ ID NO | PCR yielding SEQ ID NO |
|---|---|---|---|
| NEENAc17_forIII | atatacgcgtttagatctc gtgccgtcg | 76 | 2 |
| NEENAc17_revIII | atatggcgcgccttttgatc aagcctgttcaca | 77 | |
| NEENAc24_forIII | atatacgcgtttaagaaat cctctcttctcctc | 78 | 1 |
| NEENAc24_revIII | atatggcgcgccctgcaca tacataacatatcaagatc | 79 | |

Amplification during the PCR and purification of the amplification products was carried out as detailed above (example 1.2). Following a DNA restriction digest with M/ul (10 U/microl) and AscI (10 U/microl) restriction endonucleases, the digested products were purified with the Qiagen Gel Extraction Kit (Qiagen, Hilden, Germany).

NEENA PCR fragments (see above) were cloned separately upstream of the firefly luciferase coding sequence using AscI restriction sites. The reaction yielded one binary vector with the p-Ubi promoter, the firefly luciferase coding sequence c-LUC and the t-nos terminator and two vectors harboring SEQ ID NO1 and NO2, immediately upstream of the firefly luciferase coding sequence (Table 11), for which the combination with SEQ ID NO1 is given exemplary (SEQ ID NO80). Except for varying SEQ ID NO2, the nucleotide sequence is identical in the vectors (Table 11). The resulting vectors are summarized in table 11, with promoter molecules having the prefix p-, coding sequences having the prefix c-, and terminator molecules having the prefix t-.

TABLE 11

Plant expression vectors

| plant expression vector | Composition of the expression cassette Promoter::SEQ ID NO::reporter gene::terminator | SEQ ID NO |
|---|---|---|
| LJK309 | p-Ubi::-::c-LUC::t-nos | |
| LJK327 | p-Ubi::SEQ ID NO1::c-LUC::t-nos | 80 |
| LJK326 | p-Ubi::SEQ ID NO2::c-LUC::t-nos | |

The resulting vectors were used to analyze NEENA molecules in experiments outlined below (Example 6.2).

6.2 Generation of Transgenic Maize Plants

Maize germination, propagation, *A. tumefaciens* preparation and inoculations were done as previously described (WO2006136596, US20090249514) with the exception that the constructs LJK309, LJK326 and LJK327 (cp. example 6.1) each contained a mutated AHAS gene driven by the corn ubiquitin promoter p-Ubi, mediating tolerance to imidazolinone herbicides for selection.

6.3 NEENA Sequences Mediate Strong Enhancement of Gene Expression in Corn Plants Tissue samples were collected from the generated transgenic plants from leaves and kernels. The tissue samples were processed and analyzed as described above (cp. example 3.3)

Figure 4:
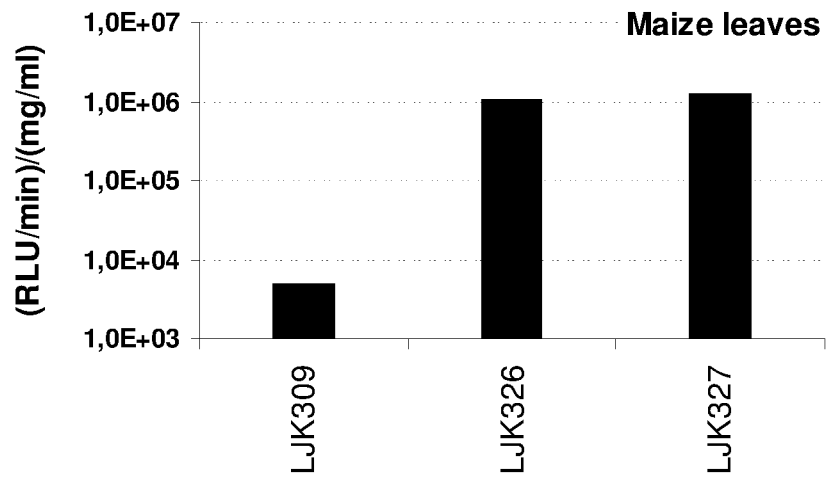
FIG. 4: Bar graph of the luciferase reporter gene activity shown as relative light units (RLU) (log scale) of independent transgenic maize plant lines harboring NEENA-less (LJK309) or NEENA-containing reporter gene constructs representing NEENA molecules from constitutively expressed genes (LJK326-LJK327) under the control of the p-ZmUbi promoter and after normalization against the protein content of each sample (averaged values, tissues of 15 independent transgenic plants analyzed). A) leaf tissue, B) kernels
Figure 4:
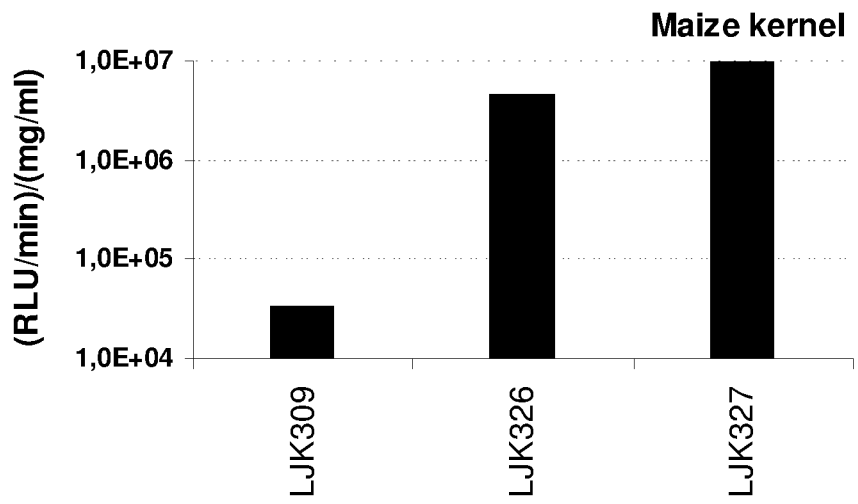

In comparison to the constitutive p-Ubi promoter-only NEENA-less reporter gene construct, the two tested NEENA molecules mediated strong enhancements in gene expression in leaves (FIG. 4a). Comparable enhancement of gene expression mediated by NEENAs (SEQ ID NO1 to NO2) was detected in maize kernels (FIG. 4b).

Example 7: Quantitative Analysis of NEENA Activity in Rice Plants

This example describes the analysis of NEENA sequences with SEQ ID NO 1 in rice plants.

7.1 Vector Construction

For analyzing NEENA sequences with SEQ ID NO 1 in rice plants quantitatively, pENTR/B vectors LJK1 and LJK4 (compare example 1.3) were combined with a destination vector harboring the constitutive PRO0239 upstream of the recombination site using site specific recombination (LR-reaction) according to the manufacturers (Invitrogen, Carlsbad, CA, USA) Gateway manual. The reactions yielded one binary vector with PRO0239 promoter, the firefly luciferase coding sequence c-LUC and the t-nos terminator as well as 1 vector harboring SEQ ID NO1 immediately upstream of the firefly luciferase coding sequence (Table 12). The resulting vectors are summarized in table 12, with promoter molecules having the prefix p-, coding sequences having the prefix c-, and terminator molecules having the prefix t-.

TABLE 12

Plant expression vectors

| plant expression vector | Composition of the expression cassette Promoter::SEQ ID NO::reporter gene::terminator | SEQ ID NO |
|---|---|---|
| CD30963 | p-PRO0239::-::c-LUC::t-nos | |
| CD30964 | p-PRO0239::SEQ ID NO1::c-LUC::t-nos | — |

The resulting vectors were used to analyze NEENA molecules in experiments outlined below (Example 7.2).

7.2 Generation of Transgenic Rice Plants

The *Agrobacterium* containing the respective expression vector was used to transform *Oryza sativa* plants. Mature dry seeds of the rice *japonica* cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the respective expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges1996, Chan et al. 1993, Hiei et al. 1994).

7.3 NEENA Sequences Mediate Strong Enhancement of Gene Expression in Rice Plants Tissue samples were collected from the generated transgenic plants from leaves and kernels. The tissue samples were processed and analyzed as described above (cp. example 3.3)

Figure 5:
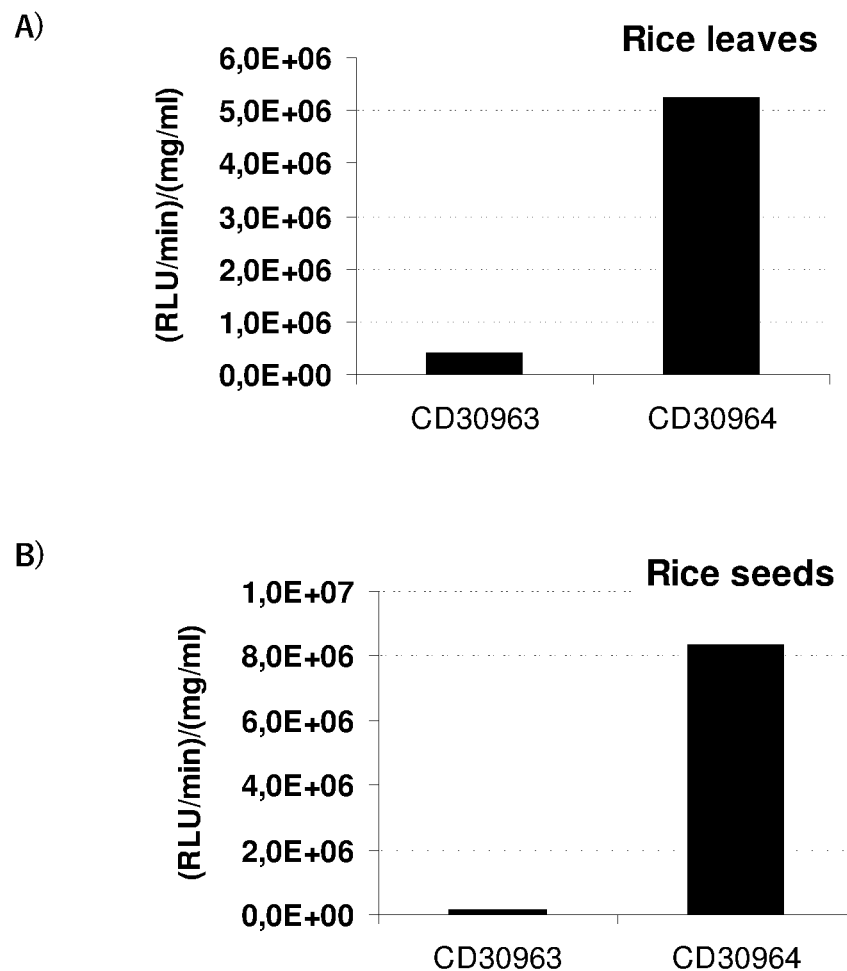
FIG. 5: Bar graph of the luciferase reporter gene activity shown as relative light units (RLU) of independent transgenic rice plant lines harboring NEENA-less (CD30963) or the NEENA-containing reporter gene construct representing a NEENA molecule from constitutively expressed genes (CD30964) under the control of the constitutive p-PRO239 promoter and after normalization against the protein content of each sample (averaged values, tissues of 15 independent transgenic plants analyzed). A) leaf tissue, B) seeds

In comparison to the constitutive p-PR0239 promoter-only NEENA-less reporter gene construct, the tested NEENA molecule (SEQ ID NO 1) mediated strong enhancements in gene expression in leaves (FIG. 5a). Strong enhancement of gene expression mediated by the NEENA (SEQ ID NO1) was detected in rice seeds (FIG. 5b).

What is claimed is:

1. A method for production of a high expression constitutive plant promoter, comprising functionally linking to a promoter one or more nucleic acid expression enhancing nucleic acid (NEENA) molecule heterologous to said promoter, wherein said NEENA consists of the nucleic acid sequence of SEQ ID NO: 3.

2. A method for producing a plant or part thereof with enhanced constitutive expression of one or more nucleic acid molecule compared to a respective control plant or part thereof, comprising:

a) introducing into a plant or part thereof one or more nucleic acid expression enhancing nucleic acid (NEENA) consisting of the nucleic acid sequence of SEQ ID NO: 3; and b) functionally linking said one or more NEENA to a constitutive promoter and to a nucleic acid molecule under the control of said constitutive promoter, wherein the NEENA is heterologous to said nucleic acid molecule and said constitutive promoter.

3. The method of claim 1, comprising:

a) introducing the one or more NEENA into a plant cell, plant, or part thereof;

b) integrating said one or more NEENA into the genome of said plant cell, plant, or part thereof, whereby said one or more NEENA is functionally linked to an endogenous constitutively expressed nucleic acid heterologous to said one or more NEENA; and optionally c) regenerating a plant or part thereof comprising said one or more NEENA from said transformed plant cell.

4. The method of claim 1 comprising:

a) providing an expression construct comprising the one or more NEENA functionally linked to a constitutive promoter and to one or more heterologous nucleic acid molecule, wherein said heterologous nucleic acid molecule is heterologous to said one or more NEENA and is under the control of said constitutive promoter;

b) integrating said expression construct comprising said one or more NEENA into the genome of said plant or part thereof; and optionally c) regenerating a plant or part thereof comprising said one or more expression construct from said transformed plant or part thereof.

5. The method of claim 1, wherein the plant is a dicot plant.

6. The method of claim 1, wherein the plant is a monocot plant.

7. The method of claim 4, wherein said one or more NEENA is functionally linked to a constitutive promoter close to the transcription start site of said heterologous nucleic acid molecule.

8. The method of claim 7, wherein said one or more NEENA is functionally linked to a constitutive promoter that is 2500 bp or fewer away from the transcription start site of said heterologous nucleic acid molecule.

9. The method of claim 4, wherein said one or more NEENA is functionally linked to a constitutive promoter that is upstream of the translational start site of the heterologous nucleic acid molecule, and the expression of said heterologous nucleic acid molecule is under the control of said constitutive promoter.

10. The method of claim 4, wherein said one or more NEENA is functionally linked to a constitutive promoter within the 5'UTR of the heterologous nucleic acid molecule, and the expression of said heterologous nucleic acid molecule is under the control of said constitutive promoter.

11. A recombinant expression construct comprising one or more constitutive promoters functionally linked to one or more NEENA consisting of a nucleic acid molecule consisting of:

the nucleic acid sequence of SEQ ID NO: 3,
wherein the one or more NEENA is heterologous to the constitutive promoter.

12. The recombinant expression construct of claim 11, wherein the one- or more NEENA is functionally linked to one or more constitutive promoter and one or more expressed nucleic acid molecule, wherein the expressed nucleic acid molecule is heterologous to said one or more NEENA.

13. A recombinant expression vector comprising one or more recombinant expression construct of claim 11.

14. A transgenic plant cell, plant, or part thereof comprising one or more constitutive promoters functionally linked to one or more heterologous NEENA consisting of a nucleic acid molecule consisting of:

SEQ ID NO: 3.

15. A transgenic cell, plant, or part thereof comprising:

a) the recombinant expression construct of claim 11; or
b) a recombinant expression vector comprising one or more of said recombinant expression construct.

16. The transgenic cell, of claim 15, selected or derived from the group consisting of bacteria, fungi, yeasts, or plants.

17. The transgenic plant or part thereof of claim 15, wherein said plant or part thereof is dicotyledonous.

18. The transgenic plant or part thereof of claim 15, wherein said plant or part thereof is monocotyledonous.

19. A transgenic cell, cell culture, seed, plant, plant part, or propagation material derived from the transgenic cell, plant, or part thereof of claim 15, wherein the transgenic cell, cell culture, seed, plant, plant part, or propagation material comprises said NEENA.

20. A method for the production of foodstuffs, animal feed, seeds, a pharmaceutical, or a fine chemical comprising:

a) providing a transgenic cell culture, seed, plant, plant part, or propagation material derived from the transgenic cell or plant of claim 19; and
b) preparing foodstuffs, animal feed, seeds, a pharmaceutical, or a fine chemical from the transgenic cell culture, seed, plant, plant part, or propagation material of a).

* * * * *

SEQUENCE LISTING

```
Sequence total quantity: 80
SEQ ID NO: 1            moltype = DNA  length = 623
FEATURE                 Location/Qualifiers
source                  1..623
                        mol_type = genomic DNA
                        organism = Petroselinum crispum
SEQUENCE: 1
ttaagaaatc ctctcttctc ctcttcattt tcaaggtaaa tctctctctc tctctctctc   60
tctgttattc cttgttttaa ttaggtatgt attattgcta gtttgttaat ctgcttatct  120
tatgtatgcc ttatgtgaat atctttatct tgttcatctc atccgtttag aagctataaa  180
tttgttgatt tgactgtgta tctacacgtg gttatgttta tatctaatca gatatgaatt  240
```

```
tcttcatatt gttgcgtttg tgtgtaccaa tccgaaatcg ttgattttt  tcatttaatc  300
gtgtagctaa ttgtacgtat acatatggat ctacgtatca attgttcatc tgtttgtgtt  360
tgtatgtata cagatctgaa acatcactt  ctctcatctg attgtgttgt tacatacata  420
gatatagatc tgttatatca tttttttat  taattgtgta tatatatg   tgcatagatc  480
tggattacat gattgtgatt atttacatga ttttgttatt tacgtatgta tatatgtaga  540
tctggacttt ttggagttgt tgacttgatt gtatttgtgt gtgtatatgt gtgttctgat  600
cttgatatgt tatgtatgtg cag                                          623

SEQ ID NO: 2            moltype = DNA   length = 519
FEATURE                 Location/Qualifiers
source                  1..519
                        mol_type = genomic DNA
                        organism = Arabidopsis thaliana
SEQUENCE: 2
ttagatctcg tgccgtcgtg cgacgttgtt ttccggtacg tttattcctg ttgattcctt   60
ctctgtctct ctcgattcac tgctacttct gtttggattc ctttcgcgcg atctctggat  120
ccgtgcgtta ttcattggct cgtcgttttc agatctgttg cgtttcttct gttttctgtt  180
atgagtggat gcgttttctt gtgattcgct tgtttgtaat gctggatctg tatctgcgtc  240
gtgggaattc aaagtgatag tagttgatat tttttccaga tcaggcatgt tctcgtataa  300
tcaggtctaa tggttgatga ttctgcggaa ttatagatct aagatcttga ttgatttaga  360
tttgaggata tgaatgagat tcgtaggtcc acaaaggtct tgttatctct gctgctagat  420
agatgattat ccaattgcgt ttcgtagtta tttttatgga ttcaaggaat tgcgtgtaat  480
tgagagtttt actctgtttt gtgaacaggc ttgatcaaa                         519

SEQ ID NO: 3            moltype = DNA   length = 618
FEATURE                 Location/Qualifiers
source                  1..618
                        mol_type = genomic DNA
                        organism = Arabidopsis thaliana
SEQUENCE: 3
ctttctctcg ttctcatctt tctctctaag gttagtccct tgtgtagatc ctctcttcat   60
cgattcaatt tcatcttcct tggtttgatt taggaattt  gtcacgattt ggtgtttaga  120
tgatggagtc ttgctgttga tctatgttta tagcacttg  tttccatggt tctgttgttt  180
cttaccgttt gttgtgcatc gatctggttt tggtagatcc ctcgtagata ataatctgaa  240
tatgtcaaag ttttcttaca agtctgttgt gttttcagtt ttgattgata ttgttatcca  300
tgtagtagtc gatcatccaa aaactggttc agtgtgattc tccgatcatc gccgctgatt  360
ttatatttat catcatgtat agatttgcag gttttatttt gttcgttgtg tgtttttgtt  420
ctttgttaaa tttaacctct atgcatttga tgtacatgtt tgttgttgg  tctcagtttc  480
tcttattctg tataagctaa gctaaagtct ccatggttag tgtctgttta gtattaaaat  540
atttcaattt gctaattctt tatgttttg  tgatgatatt gcagagattt tgtaggtgac  600
aatcaaaagt ttgacaaa                                                618

SEQ ID NO: 4            moltype = DNA   length = 772
FEATURE                 Location/Qualifiers
source                  1..772
                        mol_type = genomic DNA
                        organism = Arabidopsis thaliana
SEQUENCE: 4
tcatcagatc ttcaaaaccc caaaatttgc aaatcaggta ataacttct  ccgtatgtat   60
ctcttcgatc accgattgtc tgtttctttg tttgcttttc tcgatccgtt attgaatttt  120
tgagttcgtc gttaaatttt gattacatca atttttcttt tcgattcgat tcagagagat  180
tgaattgcaa attatgtgcc agatcttcgt gttctgtatc tgattccgga tcttggttat  240
tagttttttt tttgttgttg gaatgaattc aacaacgatt attttgattt ggtcaattga  300
tttttttaatg ctatagtttt aaccttatag gaatgtaatt gaactggatc agctttactt  360
gaattgtttg gatctagatt attcagacaa catctttta  actaaattga aacatatttg  420
tgtttgtgtt cttgatgatc atgtgaattt ggtagcataa ttttcttgtt gagatgattt  480
ctgagatggg ttttttgtagt ttaatttct  tactcgatga accatctcgt gcaccttgca  540
aaatctttg  ttctatatct cattgttcga tatcaaacta atgaggttaa cgttttttgg  600
tgagacgacc agttatgtaa catgttgtta actatcttca tgtttgaatc gattttgatt  660
ggatgttttc atgttctatc atattctgcg gtttttgaatc ttctgaattc taacgtgagg  720
ttatccttct tgtgcagatc tcagcttccc ggttagtact accctcaaat ca          772

SEQ ID NO: 5            moltype = DNA   length = 332
FEATURE                 Location/Qualifiers
source                  1..332
                        mol_type = genomic DNA
                        organism = Arabidopsis thaliana
SEQUENCE: 5
aaatcgttct ttcaaatctc tcaatcggga tcaaggtaaa tttctgggtt cttattcagt   60
ttcttcgatt attttccatt cgatcgcaat ttcgtccctg ttctttgagt ttgattcggt  120
taatctttga tcggagataa atatctgagt ttcatcgcta gatctcatct atattctgaa  180
ctagggttcg tagatttcac agatttgtat atttaggcgt cgattctttg aatttgatcc  240
gatatgtgat ttatattcag atcggtggt  agctttttta atcggatttg agattatcca  300
agcgattaat ctcagttttt tgtgaattac ag                                332
```

```
SEQ ID NO: 6                moltype = DNA   length = 501
FEATURE                     Location/Qualifiers
source                      1..501
                            mol_type = genomic DNA
                            organism = Arabidopsis thaliana
SEQUENCE: 6
cccatctctc atctccactc ttctcattcc gtaaggtacg cttccgagtt tccatggctt    60
ccgcatgact attcttgctc tctcccttcc cactctctta tttaccttcc gtctcttcgt   120
tttcttctca attcaatttt cgtttgattc cgtttcttct tcgttcgtta atacttagat   180
cttaatccgg tgagtgaaat tctatgaaac acagatctgg atttttttata cgatcagatt   240
cgtaaaatct ctgttttgcg atctttctct gcgttagatc tctgttttcc ctagttgtga   300
ttcgttttga tctttaaact ctctcatact ctgtttcaa taaatacgac aaaaaaaact   360
gcaaaagttt tttactttt taacgattgg tggcttttac catatgacaa gaagtacatt   420
ttaggattgt gtttggttta ctgactgatt ttggttttgt ttgtggttca aatgtagtaa   480
aaaaacaaaa aacaaacaaa a                                             501

SEQ ID NO: 7                moltype = DNA   length = 535
FEATURE                     Location/Qualifiers
source                      1..535
                            mol_type = genomic DNA
                            organism = Arabidopsis thaliana
SEQUENCE: 7
agccgcaaga ctcctttcag attcttactt gcaggttaga tatttctct ctttagtgtc    60
tccgatcttc atcttcttat gattattgta gctgttaggg tttagattc ttagttttag   120
ctctatattg actgtgatta tcgcttattc tttgctgttg ttatactgct tttgattctc   180
tagctttaga tccgtttact cgtcgatcaa tattgttcct attgagtctg atgtataatc   240
ctctgattaa ttgatagcgt ttagtttga tatcgtcttc gcatgttttt tatcatgtcg   300
atctgtatct gctctggtta tagttgattc tgatgtattt ggttggtgat gttccttaga   360
tttgatatac ctgttgtctc gtggtttgat atgatagctc aactgtgat atgtggtttt   420
gtttcagtgg atctgtgttt gattatattg ttgacgtttt ggttgttgta tagttgatgg   480
ttgatgtatt tttgttgatt ctgatgtttc gattttgtt tttgttttga cagct        535

SEQ ID NO: 8                moltype = DNA   length = 346
FEATURE                     Location/Qualifiers
source                      1..346
                            mol_type = genomic DNA
                            organism = Arabidopsis thaliana
SEQUENCE: 8
atctttacct caacaacgag atctgtttcc acggtaccat tttcatccga tctctgttct    60
tctatgtttg tttactggat ccgttgattt tactttcatc ttatcatttg tgtgtggcta   120
ttttggtgaa ttgatgcgat cttaagctgt ttctaggttc aagccttata tgtttcttct   180
aagctaatca taggtcgtag acttgttagg aagattcgaa tctagtacaa agttagcaac   240
tttagcatac gtaaatcgtt agtagtaatt tctagattga tagaggttcg agaccttaaa   300
aggtgatgaa tatttggtgg gttttgttta ttagaaagaa aggagg                  346

SEQ ID NO: 9                moltype = DNA   length = 316
FEATURE                     Location/Qualifiers
source                      1..316
                            mol_type = genomic DNA
                            organism = Arabidopsis thaliana
SEQUENCE: 9
cgattcgggt caaggttatt gactttctca ttcaggtatc atcttcttcc tcgtcccata    60
ctttttgatt cacttgctta ttcctctgcc ggtttcgatt atatttgttt ggatcggata   120
attgtatggg cttaagctta tttcgctgtt aaatgtgttg attggtgtt aagagtgttg   180
tataactgga ttggtgctca tacatctgga gatttatgtt tgatgattt gtatgatgtg   240
tttttggttt gaggatgatt tattcctttg gtcttacttt tctcttttg tgaatttaag   300
cagtgaagct tgaatc                                                   316

SEQ ID NO: 10               moltype = DNA   length = 165
FEATURE                     Location/Qualifiers
source                      1..165
                            mol_type = genomic DNA
                            organism = Arabidopsis thaliana
SEQUENCE: 10
ttcgaagaac caaaaccaaa aacgtgaatt cggagttatg attttggatc ttcttcccgt    60
cttatatat aattttctgg gttatgtttt tcttcttctt aattcatctg accattggat   120
tggttttcga ttgcagagtc ttcaattgga atttggatcg tggga                   165

SEQ ID NO: 11               moltype = DNA   length = 155
FEATURE                     Location/Qualifiers
source                      1..155
                            mol_type = genomic DNA
                            organism = Arabidopsis thaliana
SEQUENCE: 11
atcgtcaaaa ccgagtttgg aggatctgtc ttgaggtaaa aaagctcaat cctttatcgg    60
aaattttcaa cctttgcttt tcctttgttt gttgcgttgc tgaatctatc tagggtttgg   120
ttttttggat ctaggagttt ttttttggtt gagaa                              155
```

| SEQ ID NO: 12 | moltype = DNA   length = 116 |
| --- | --- |
| FEATURE | Location/Qualifiers |
| source | 1..116 |
| | mol_type = genomic DNA |
| | organism = Arabidopsis thaliana |

SEQUENCE: 12

```
gatccctact tctctcgaca cttatagagt ttcaggtcca ttctctgatt cctgtttttt    60
cattttctaa tttcctattt acgggttttt actaatcttc tattgatcct ccagtc       116
```

| SEQ ID NO: 13 | moltype = DNA   length = 369 |
| --- | --- |
| FEATURE | Location/Qualifiers |
| source | 1..369 |
| | mol_type = genomic DNA |
| | organism = Arabidopsis thaliana |

SEQUENCE: 13

```
aaatcaatct ctcaaatctc tcaaccgtga tcaaggtaga tttctgagtt cttattgtat    60
ttcttcgatt tgtttcgttc gatcgcaatt taggctctgt tctttgattt tgatctcgtt   120
aatctctgat cggaggcaaa ttacatagtt tcatcgttag atctcttctt atttctcgat   180
tagggttcgt atttttcgca gatctgttta ttttcttgtt gtttccttgt atttgatccg   240
atttgttgaa agaatttgtg tgttctcgat tatttacgct ttgatctgtg atttttatct   300
agatttggtg ttagtttctt gtttgtgcga tcgaatttgt cgattaatct cggttttttct  360
gattaacag                                                          369
```

| SEQ ID NO: 14 | moltype = DNA   length = 235 |
| --- | --- |
| FEATURE | Location/Qualifiers |
| source | 1..235 |
| | mol_type = genomic DNA |
| | organism = Arabidopsis thaliana |

SEQUENCE: 14

```
ctcatcgttg gagcttagaa gccgtcggca caaggttcgt ctttctctca tcccttccct    60
cttcctttgc gtgaattcac cagaaaatgt atatctacct tagcgagtct gtctagttta   120
gcgaatctag gataatctcc ggaagacact tttgaatcat cactgttttt gatctctgtt   180
tctttctcta attgtgttgt tgtattactg ttgatgtaga agaagaagaa gaaga         235
```

| SEQ ID NO: 15 | moltype = DNA   length = 204 |
| --- | --- |
| FEATURE | Location/Qualifiers |
| source | 1..204 |
| | mol_type = genomic DNA |
| | organism = Arabidopsis thaliana |

SEQUENCE: 15

```
ccttgcgaaa agcattttcg atcttactct taggtagtct atgattctcc atttgatccg    60
tttatacttg ttattggcat ttcatcatcg tctgggttgt tcgacttact ctaatttttgg  120
tttaaaacgg atttaaagtt tgttttttttg tgaataagca attaatctat tgttactgtt   180
tttgaatcgt ttcaggataa aaaa                                          204
```

| SEQ ID NO: 16 | moltype = DNA   length = 674 |
| --- | --- |
| FEATURE | Location/Qualifiers |
| source | 1..674 |
| | mol_type = genomic DNA |
| | organism = Arabidopsis thaliana |

SEQUENCE: 16

```
ttttgacgcc gccgcttctt cttcttcctc gcaggtacgt tctgggtaac ttagggattg    60
cgtcgttgtc ggaaactgca aaagcttgtg ctgtaggttt cgatttgttg ttttttttt    120
tgtctctgta gcttttgaat cttaggtttg gttagattcg ttaataagat aatgaaaag   180
ttatgaaatg ggttgatttt tattaccgga tactgccgct gcatcttcat tcttttagtt   240
ttattgtatc aatggcttcg ttgttttat aatcacatta ggcctctgtc aagttcagtg   300
ttatgtgat gtatattttct tgattcattt gcaattctct agacattatt tgacattgca   360
tttacatgtg attcctgtgt ttgtttagtg ttacacctga atgttgatgt ttaagacaca   420
aatcaactat acacttggtt gtttcttcat ttgtcatatg cttatggatc tctattgttt   480
ctatttgaca ttgctgttca tatgtttcct tgaactatga ttataacaat cgatgcttta   540
ggtgcatttc ttgatacata aatggtttta aatttcatgat gtaattgaat cacggatttt   600
gaaccctaac taaagacatg gaattttcttt tggttttccc ctttcagcag gtaagtcaca   660
caggtaactg aaag                                                     674
```

| SEQ ID NO: 17 | moltype = DNA   length = 603 |
| --- | --- |
| FEATURE | Location/Qualifiers |
| source | 1..603 |
| | mol_type = genomic DNA |
| | organism = Arabidopsis thaliana |

SEQUENCE: 17

```
gatacgttaa cttcaccaat ccccaagacg gttagtctcc ttaatttttat ttggacttct    60
tcttacaatt tccaattttt agggtttgct cgatagtacc agtactggat ttgaatgagg   120
tgtgttttaa atgttgatac tttatggtgt ttgtatgtat gcaatgtggt tggtgctgtt   180
ggaaagctta tccctgctt aatcaatctt tttaatgcta cttctgtctt ctaatggtac   240
tttatctcgt gtctttgttg cagctgcaag agcgatccaa gaactgaatt acatacctct   300
ttatggaaaa cctattaggg ttatgtattc tcatcgtgat cctagtgttc gccgaagtgg   360
cgctggcaac atttttatta agtacgcttg tctctatcct tctgacattt gagttgctgt   420
aagacgagat gattgttgcg aaaaaatttg tatcttgtat tattcattga aaagtctggc   480
```

```
aaaagtagtt gatttcttta gttatgtaag tttttttatt gggtgttctt tctctctttc    540
tgatgctaaa cctggctata atatgcagaa tttggacgag tccatcgacc acaaagcact    600
gca                                                                  603

SEQ ID NO: 18           moltype = DNA  length = 919
FEATURE                 Location/Qualifiers
source                  1..919
                        mol_type = genomic DNA
                        organism = Arabidopsis thaliana
SEQUENCE: 18
ctctcttccg tctcgagtcg ctgagatcca tcaggttcgt ttctattcga atctattctc    60
ttgaatccgt atttgtttcc tttcctctct agatagattt cattttctg gaaacattga    120
gatttccatt gatttgatgt ttagtggttt agatcggata attttgtta ttgactaata    180
aaaaacgaat cataactatc ttaaaacttt gtttacgcat tgttattgaa ggctaaataa    240
aaaatgctca attgttgcta gaaggaagg tgtctcgaaa acatgtgaat ttattttttg    300
agcctcattg tttctcactg caacaatagt gaatgattca attgaaaaga acttttggtt    360
aagccatttt tctctttaat agattatgtg tctcaactca attaggaact gtgtgttttt    420
ttgtttcctt gatgttaact tgtgagttga tttatttggg tagtttactt gtatatatat    480
ttggtggtgg gtcctggagg gaaatgagtg agagggagct ctgttcatac attctatgtt    540
tttaaatgat tagtatttt ctttcatcta atacttgctt tttgtgctag gaattctgat    600
ttttgggact aaatttatcga gtatatataa ttggataagt gagtttggta ttaatattaa    660
gagcaattag gttggttatc ttgccaaaca gtagacccct gtcgttttct tagtcattta    720
agaagtaatg cttaagattc aggcctctaa tctggttatg atagtgaaga ggatctgtaa    780
atttacctat acgacctgtt gaaaaggacc tctggtgttt gttactatgc gtttctgatc    840
aatatagaca tagttggatc atattcttct cttgatcgtc tgtttcattt ttttttcaaaa    900
tcagtaaaag gtctgcaaa                                                 919

SEQ ID NO: 19           moltype = DNA  length = 601
FEATURE                 Location/Qualifiers
source                  1..601
                        mol_type = genomic DNA
                        organism = Arabidopsis thaliana
SEQUENCE: 19
tttccttcct cctctccgat tcttcctccg tcaggttcgt ctccgacttt ctatgtcttc    60
cttacgtctc tcttatttag ctcccttttcc ttccttctcc acgttattat tactacttcg    120
cttttagtgt gattcgtttc attctcgttt tttatattc ctcgatcgt ttgctcattt    180
gttgagatct attcgctatg tgagttcatt tgactcagat ctggatattt cgtgttgttc    240
gatttataga tctggtttct ggatctgttt acgatctatc gtcatctttc ctttgaaaat    300
gattggtgtt tctgtgttcg tattcgttta gatctaaagt ttttgatcga tgaatgtcgc    360
atgtgttttt atctgaaagt tttcgattac agtatcaagt ggtggtagta gtagtagtag    420
actcaaaaag ctgcacaaac tttttataca cgtgaattgt gattgcttta cggttttctt    480
ggagtttgtt aattaaatca tttaatatta agaagtttat gaattaagag aacgttattt    540
tatactatga ttttgatttt gatttggttt gtgtgtttta atgcagtaaa agaaaatcaa    600
a                                                                    601

SEQ ID NO: 20           moltype = DNA  length = 36
FEATURE                 Location/Qualifiers
misc_feature            1..36
                        note = synthetic sequence
source                  1..36
                        mol_type = other DNA
                        organism = synthetic construct
SEQUENCE: 20
tttatggtac cagccgcaag actcctttca gattct                              36

SEQ ID NO: 21           moltype = DNA  length = 39
FEATURE                 Location/Qualifiers
misc_feature            1..39
                        note = synthetic sequence
source                  1..39
                        mol_type = other DNA
                        organism = synthetic construct
SEQUENCE: 21
aaattccatg gtagctgtca aacaaaaac aaaaatcga                            39

SEQ ID NO: 22           moltype = DNA  length = 37
FEATURE                 Location/Qualifiers
misc_feature            1..37
                        note = synthetic sequence
source                  1..37
                        mol_type = other DNA
                        organism = synthetic construct
SEQUENCE: 22
aaaaaggtac ctcgaagaac caaaaccaaa aacgtga                             37

SEQ ID NO: 23           moltype = DNA  length = 44
FEATURE                 Location/Qualifiers
misc_feature            1..44
                        note = synthetic sequence
```

```
source                  1..44
                        mol_type = other DNA
                        organism = synthetic construct
SEQUENCE: 23
tttttccatg gttatttatc caaaatccca cgatccaaat tcca              44

SEQ ID NO: 24           moltype = DNA   length = 33
FEATURE                 Location/Qualifiers
misc_feature            1..33
                        note = synthetic sequence
source                  1..33
                        mol_type = other DNA
                        organism = synthetic construct
SEQUENCE: 24
tttttggtac cgatccctac ttctctcgac act                          33

SEQ ID NO: 25           moltype = DNA   length = 34
FEATURE                 Location/Qualifiers
misc_feature            1..34
                        note = synthetic sequence
source                  1..34
                        mol_type = other DNA
                        organism = synthetic construct
SEQUENCE: 25
ttttaccatg gtgactggag gatcaataga agat                         34

SEQ ID NO: 26           moltype = DNA   length = 37
FEATURE                 Location/Qualifiers
misc_feature            1..37
                        note = synthetic sequence
source                  1..37
                        mol_type = other DNA
                        organism = synthetic construct
SEQUENCE: 26
tttttggtac ctttctctcg ttctcatctt tctctct                      37

SEQ ID NO: 27           moltype = DNA   length = 36
FEATURE                 Location/Qualifiers
misc_feature            1..36
                        note = synthetic sequence
source                  1..36
                        mol_type = other DNA
                        organism = synthetic construct
SEQUENCE: 27
taatagatat ctttgtcaaa cttttgattg tcacct                       36

SEQ ID NO: 28           moltype = DNA   length = 34
FEATURE                 Location/Qualifiers
misc_feature            1..34
                        note = synthetic sequence
source                  1..34
                        mol_type = other DNA
                        organism = synthetic construct
SEQUENCE: 28
tataaggtac caaatcaatc tctcaaatct ctca                         34

SEQ ID NO: 29           moltype = DNA   length = 35
FEATURE                 Location/Qualifiers
misc_feature            1..35
                        note = synthetic sequence
source                  1..35
                        mol_type = other DNA
                        organism = synthetic construct
SEQUENCE: 29
tttatccatg gtctgttaat cagaaaaacc gagat                        35

SEQ ID NO: 30           moltype = DNA   length = 34
FEATURE                 Location/Qualifiers
misc_feature            1..34
                        note = synthetic sequence
source                  1..34
                        mol_type = other DNA
                        organism = synthetic construct
SEQUENCE: 30
tatatggtac caaatcgttc tttcaaatct ctca                         34

SEQ ID NO: 31           moltype = DNA   length = 35
FEATURE                 Location/Qualifiers
```

```
misc_feature            1..35
                        note = synthetic sequence
source                  1..35
                        mol_type = other DNA
                        organism = synthetic construct
SEQUENCE: 31
ttataccatg gtctgtaatt cacaaaaaac tgaga                               35

SEQ ID NO: 32           moltype = DNA  length = 32
FEATURE                 Location/Qualifiers
misc_feature            1..32
                        note = synthetic sequence
source                  1..32
                        mol_type = other DNA
                        organism = synthetic construct
SEQUENCE: 32
tttttggtac ctcatcgttg gagcttagaa gc                                  32

SEQ ID NO: 33           moltype = DNA  length = 35
FEATURE                 Location/Qualifiers
misc_feature            1..35
                        note = synthetic sequence
source                  1..35
                        mol_type = other DNA
                        organism = synthetic construct
SEQUENCE: 33
tttttccatg gtcttcttct tcttcttcta catca                               35

SEQ ID NO: 34           moltype = DNA  length = 38
FEATURE                 Location/Qualifiers
misc_feature            1..38
                        note = synthetic sequence
source                  1..38
                        mol_type = other DNA
                        organism = synthetic construct
SEQUENCE: 34
tatatggtac caaagcattt tcgatcttac tcttaggt                            38

SEQ ID NO: 35           moltype = DNA  length = 33
FEATURE                 Location/Qualifiers
misc_feature            1..33
                        note = synthetic sequence
source                  1..33
                        mol_type = other DNA
                        organism = synthetic construct
SEQUENCE: 35
tttttccatg gttttttatc ctgaaacgat tca                                 33

SEQ ID NO: 36           moltype = DNA  length = 36
FEATURE                 Location/Qualifiers
misc_feature            1..36
                        note = synthetic sequence
source                  1..36
                        mol_type = other DNA
                        organism = synthetic construct
SEQUENCE: 36
tttttggtac cttttgacgc cgccgcttct tcttct                              36

SEQ ID NO: 37           moltype = DNA  length = 38
FEATURE                 Location/Qualifiers
misc_feature            1..38
                        note = synthetic sequence
source                  1..38
                        mol_type = other DNA
                        organism = synthetic construct
SEQUENCE: 37
tttttccatg gtctttcagt tacctgtgtg acttacct                            38

SEQ ID NO: 38           moltype = DNA  length = 33
FEATURE                 Location/Qualifiers
misc_feature            1..33
                        note = synthetic sequence
source                  1..33
                        mol_type = other DNA
                        organism = synthetic construct
SEQUENCE: 38
tttaaggtac ccatctctca tctccactct tct                                 33

SEQ ID NO: 39           moltype = DNA  length = 37
```

```
FEATURE                 Location/Qualifiers
misc_feature            1..37
                        note = synthetic sequence
source                  1..37
                        mol_type = other DNA
                        organism = synthetic construct
SEQUENCE: 39
tttttgatat cttttgtttg tttttgttt tttact                                    37

SEQ ID NO: 40           moltype = DNA  length = 34
FEATURE                 Location/Qualifiers
misc_feature            1..34
                        note = synthetic sequence
source                  1..34
                        mol_type = other DNA
                        organism = synthetic construct
SEQUENCE: 40
ttataggtac caagtgaatc gtcaaaaccg agtt                                     34

SEQ ID NO: 41           moltype = DNA  length = 34
FEATURE                 Location/Qualifiers
misc_feature            1..34
                        note = synthetic sequence
source                  1..34
                        mol_type = other DNA
                        organism = synthetic construct
SEQUENCE: 41
tttttccatg gttctcaacc aaaaaaaaac tcct                                     34

SEQ ID NO: 42           moltype = DNA  length = 34
FEATURE                 Location/Qualifiers
misc_feature            1..34
                        note = synthetic sequence
source                  1..34
                        mol_type = other DNA
                        organism = synthetic construct
SEQUENCE: 42
tttttggtac cacgattcgg gtcaaggtta ttga                                     34

SEQ ID NO: 43           moltype = DNA  length = 40
FEATURE                 Location/Qualifiers
misc_feature            1..40
                        note = synthetic sequence
source                  1..40
                        mol_type = other DNA
                        organism = synthetic construct
SEQUENCE: 43
tttttccatg gtgattcaag cttcactgct taaattcaca                               40

SEQ ID NO: 44           moltype = DNA  length = 34
FEATURE                 Location/Qualifiers
misc_feature            1..34
                        note = synthetic sequence
source                  1..34
                        mol_type = other DNA
                        organism = synthetic construct
SEQUENCE: 44
tttttggtac cttagatctc gtgccgtcgt gcga                                     34

SEQ ID NO: 45           moltype = DNA  length = 31
FEATURE                 Location/Qualifiers
misc_feature            1..31
                        note = synthetic sequence
source                  1..31
                        mol_type = other DNA
                        organism = synthetic construct
SEQUENCE: 45
tttttccatg gtttgatcaa gcctgttcac a                                        31

SEQ ID NO: 46           moltype = DNA  length = 34
FEATURE                 Location/Qualifiers
misc_feature            1..34
                        note = synthetic sequence
source                  1..34
                        mol_type = other DNA
                        organism = synthetic construct
SEQUENCE: 46
aaaaaggtac ctcatcagat cttcaaaacc ccaa                                     34
```

```
SEQ ID NO: 47          moltype = DNA   length = 38
FEATURE                Location/Qualifiers
misc_feature           1..38
                       note = synthetic sequence
source                 1..38
                       mol_type = other DNA
                       organism = synthetic construct
SEQUENCE: 47
aaaaaccatg gtgatttgag ggtagtacta accgggaa                                 38

SEQ ID NO: 48          moltype = DNA   length = 36
FEATURE                Location/Qualifiers
misc_feature           1..36
                       note = synthetic sequence
source                 1..36
                       mol_type = other DNA
                       organism = synthetic construct
SEQUENCE: 48
ttttaggtac catacgttaa cttcaccaat ccccaa                                   36

SEQ ID NO: 49          moltype = DNA   length = 42
FEATURE                Location/Qualifiers
misc_feature           1..42
                       note = synthetic sequence
source                 1..42
                       mol_type = other DNA
                       organism = synthetic construct
SEQUENCE: 49
tttttccatg gttaattaat gcagtgcttt gtggtcgatg ga                            42

SEQ ID NO: 50          moltype = DNA   length = 33
FEATURE                Location/Qualifiers
misc_feature           1..33
                       note = synthetic sequence
source                 1..33
                       mol_type = other DNA
                       organism = synthetic construct
SEQUENCE: 50
tttttcccgg gatctttacc tcaacaacga gat                                      33

SEQ ID NO: 51          moltype = DNA   length = 44
FEATURE                Location/Qualifiers
misc_feature           1..44
                       note = synthetic sequence
source                 1..44
                       mol_type = other DNA
                       organism = synthetic construct
SEQUENCE: 51
tttttccatg gttatcctcc tttctttcta ataaacaaaa ccca                          44

SEQ ID NO: 52          moltype = DNA   length = 36
FEATURE                Location/Qualifiers
misc_feature           1..36
                       note = synthetic sequence
source                 1..36
                       mol_type = other DNA
                       organism = synthetic construct
SEQUENCE: 52
tttttggtac ctctcttccg tctcgagtcg ctgaga                                   36

SEQ ID NO: 53          moltype = DNA   length = 31
FEATURE                Location/Qualifiers
misc_feature           1..31
                       note = synthetic sequence
source                 1..31
                       mol_type = other DNA
                       organism = synthetic construct
SEQUENCE: 53
tttttccatg gtttgcagac cttttactga t                                        31

SEQ ID NO: 54          moltype = DNA   length = 37
FEATURE                Location/Qualifiers
misc_feature           1..37
                       note = synthetic sequence
source                 1..37
                       mol_type = other DNA
                       organism = synthetic construct
SEQUENCE: 54
tttttggtac cttccttcct cctctccgat tcttcct                                  37
```

```
SEQ ID NO: 55           moltype = DNA   length = 34
FEATURE                 Location/Qualifiers
misc_feature            1..34
                        note = synthetic sequence
source                  1..34
                        mol_type = other DNA
                        organism = synthetic construct
SEQUENCE: 55
tttttccatg gttattgatt ttcttttact gcat                                     34

SEQ ID NO: 56           moltype = DNA   length = 34
FEATURE                 Location/Qualifiers
misc_feature            1..34
                        note = synthetic sequence
source                  1..34
                        mol_type = other DNA
                        organism = synthetic construct
SEQUENCE: 56
tttttttggta ccttaagaaa tcctctcttc tcct                                    34

SEQ ID NO: 57           moltype = DNA   length = 34
FEATURE                 Location/Qualifiers
misc_feature            1..34
                        note = synthetic sequence
source                  1..34
                        mol_type = other DNA
                        organism = synthetic construct
SEQUENCE: 57
tttttttccat ggtctgcaca tacataacat atca                                    34

SEQ ID NO: 58           moltype = DNA   length = 51
FEATURE                 Location/Qualifiers
misc_feature            1..51
                        note = synthetic sequence
source                  1..51
                        mol_type = other DNA
                        organism = synthetic construct
SEQUENCE: 58
ggggacaact ttgtatagaa aagttgtcga gaccagatgt tttacacttg a                  51

SEQ ID NO: 59           moltype = DNA   length = 51
FEATURE                 Location/Qualifiers
misc_feature            1..51
                        note = synthetic sequence
source                  1..51
                        mol_type = other DNA
                        organism = synthetic construct
SEQUENCE: 59
ggggactgct tttttgtaca aacttggaca ctcagagact tgagagaagc a                  51

SEQ ID NO: 60           moltype = DNA   length = 73
FEATURE                 Location/Qualifiers
misc_feature            1..73
                        note = synthetic sequence
source                  1..73
                        mol_type = other DNA
                        organism = synthetic construct
SEQUENCE: 60
ggtacccggg gatcctctag catatgctcg aggcggccgc agatatcaga tctggtcgac         60
ggcatgcaag ctt                                                            73

SEQ ID NO: 61           moltype = DNA   length = 12176
FEATURE                 Location/Qualifiers
misc_feature            1..12176
                        note = vector sequence
source                  1..12176
                        mol_type = other DNA
                        organism = synthetic construct
SEQUENCE: 61
gacatacaaa tggacgaacg gataaacctt tcacgccct  tttaaatatc cgattattct         60
aataaacgct cttttctctt aggtttaccc gccaatatat cctgtcaaac actgatagtt        120
taaactgaag gcgggaaacg acaatcagat ctagtaggaa acagctatga ccatgattac        180
gccaagctat cgattacgcc aagctatcaa ctttgtatag aaaagttgca tcaagatctt        240
ggtgatgtag caagagctaa gttgtacttc gattcggttg gacattactc gagaccagat        300
gttttacact tgaccgtaaa tgagcaccct aagaaaccgg tcacattcat ttcgaaggtg        360
gagaaagcgg aagatgactc aaacaagtaa tcggttgtga ttcgtcagtt catgtcactc        420
ctatgaagga gtcaagttca aaatgttatg ttgagtttca aacttttatg ctaaactttt        480
tttctttatt ttcgttaata atggaagaga accaattctc ttgtatctaa agattatcca        540
```

```
tctatcatcc aatttgagtg ttcaattctg gatgttgtgt taccctacat tctacaacca    600
tgtagccaat tattatgaat ctggctttga tttcagttgt gttctttcct ttttttttctt   660
tgcatatttg catttagaat gtttaataat taagttactg tatttccaca tacattagtt    720
ccaagaatat acatatatta atttattttt cttaaaaatg ttttggaatg actaatattg    780
acaacgaaaa tagaagctat gctaaaccat tacgtatatg tgacttcaca tgttgttgtt    840
ttacattccc tatatatatg gatggctgtc acaatcagaa acgtgatcga aaaaagacaa    900
acagtgtttg cataaaaaga ctatttcgtt tcattgacaa tttgtgttta tttgtaaaga    960
aaagtggcaa agtggaattt gagttcctgc aagtaagaaa gatgaaataa aagacttgag   1020
tgtgtgtttt tttcttttat ctgaaagctg caatgaaata ttcctaccaa gcccgtttga   1080
ttattaattg gggtttggtt ttcttgatgc gaactaattg gttatataag aaactataca   1140
atccatgtta attcaaaaat tttgatttct cttgtaggaa tatgatttac tatatgagac   1200
tttcttttcg ccaataatag taaatccaaa gatatttgac cggaccaaaa cacattgatc   1260
tattttttag tttatttaat ccagtttctc tgagataatt cattaaggaa aacttagtat   1320
taacccatcc taagattaaa taggagccaa actcacattt caaatattaa ataacataaa   1380
atggatttaa aaaatctata cgtcaaattt tatttatgac atttcttatt taaatttata   1440
tttaatgaaa tacagctaag acaaaccaaa aaaaaaatac tttctaagtg gtccaaaaca   1500
tcaattccgt tcaatattat taggtagaat cgtacgacca aaaaaaggta ggttaatacg   1560
aattagaaac atatctataa catagtatat attattaccct attatgagga atcaaaatgc   1620
atcaaatatg gatttaagga atccataaaa gaataaattc tacgggaaaa aaaatggaat   1680
aaattctttt aagtttttta tttgtttttt atttggtagt tctccatttt gttttatttc   1740
gtttggattt attgtgtcca aatactttgt aaaccaccgt tgtaattctt aaacggggtt   1800
ttcacttctt ttttatattc agacataaag catcggctgg tttaatcaat caatagattt   1860
tattttttctt ctcaattatt agtaggtttg atgtgaactt tacaaaaaaa acaaaaacaa   1920
atcaatgcag agaaaagaaa ccacgtgggc tagtcccacc ttgtttcatt tccaccacag   1980
gttcgatctt cgttaccgtc tccaatagga aaataaacgt gaccacaaaa aaaaaacaaa   2040
aaaaagtcta tatattgctt ctctcaagtc tctgagtgtc atgaaccaaa gtaaaaaaca   2100
aagactcgag tcaagtttgt acaaaaaagc aggctggtac cttaagaaat cctctcttct   2160
cctcttcatt ttcaaggtaa atctctctct ctctctctct ctctgttatt ccttgttttta  2220
attaggtatg tattattgct agtttgttaa tctgcttatc ttatgtatgc cttatgtgaa   2280
tatctttatc ttgttcatct catccgttca gaagctataa atttgttgat ttgactgtgt   2340
atctacacgt ggttatgttt atatctaatc agatatgaat ttcttcatat tgttgcgttt   2400
gtgtgtacca atccgaaatc gttgattttt ttcatttaat cgtgtagcta attgtacgta   2460
tacatatgga tctacgtatc aattgttcat ctgtttgtgt ttgtatgtat acagatctga   2520
aaacatcact tctctcatct gattgtgttg ttacatacat agatatagat ctgttatatc   2580
attttttttta ttaattgtgt atatatatat gtgcatagat ctggattaca tgattgtgat   2640
tatttacatg attttgttat ttacgtatgt atatatgtag atctggactt tttgagttg    2700
ttgacttgat tgtatttgtg tgtgtatatg tgtgttctga tcttgatatg ttatgtatgt   2760
gcagaccatg gaagacgcca aaaacataaa gaaaggcccg cgccattct atccgctgga    2820
agatgaaacc gctggagagc aactgcataa ggctatgaag agatacgccc tggttcctgg   2880
aacaattgct tttacagatg cacatatcga ggtggacatc acttacgctg agtacttcga   2940
aatgtccgtt cggttggcag aagctatgaa acgatatggg ctgaatacaa atcacagaat   3000
cgtcgtatgc agtgaaaact ctcttcaatt ctttatgccg gtgttgggcg cgttatttat   3060
cggagttgca gttgcgcccg cgaacgacat ttataatgaa cgtgaattgc tcaacagtat   3120
gggcatttcg cagcctaccg tggtgttcgt ttccaaaaag gggttgcaaa aattttgaa    3180
cgtgcaaaaa aagctcccaa tcatccaaaa aattattatc atggattcta aaacggatta   3240
ccagggattt cagtcgatgt acacgttcgt cacatctcat ctacctcccg gttttaatga   3300
atacgatttt gtgccagagt ccttcgatag ggacaagaca attgcactga tcatgaactc   3360
ctctggatct actggtctgc ctaaaggtgt cgctctgcct catagaactg cctgcgtgag   3420
attctcgcat gccagagatc ctatttttgg caatcaaatc attccggata ctgcgatttt   3480
aagtgttgtt ccattccatc acggtttttgg aatgtttact acactcggat atttgatatg   3540
tggatttcga gtcgtcttaa tgtatagatt tgaagaagag ctgtttctga ggagccttca   3600
ggattacaag attcaaagtg cgctgctggt gccaacccta ttctccttct tcgccaaaag   3660
cactctgatt gacaaatacg atttatctaa tttacacgaa attgcttctg gtggcgctcc   3720
cctctctaag gaagtcgggg aagcggttgc caagaggttc catctgccag gtatcaggca   3780
aggatatggg ctcactgaga tacatcagc tattctgatt acacccgagg gggatgataa    3840
accgggcgcg gtcggtaaag ttgttccatt ttttgaagcg aaggttgtgg atctggatac   3900
cgggaaaacg ctgggcgtta atcaagagg cgaactgtgt gtgagaggtc ctatgattat    3960
gtccggttat gtaaacaatc cggaagcgac caacgccttg attgacaagg atggatggct   4020
acattctgga gacatagctt actgggacga agacgaacac ttcttcatcg ttgaccgcct   4080
gaagtctctg attaagtaca aaggctatca ggtggctccc gctgaattgg aatccatctt   4140
gctccaacac cccaacatct tcgacgcagg tgtcgcaggt cttcccgacg atgacgccgg   4200
tgaacttccc gccgccgttg ttgttttgga gcacggaaag acgatgacgg aaaaagagat   4260
cgtggattac gtcgccagtc aagtaacaac cgcgaaaaag ttgcgcggag gagttgtgtt   4320
tgtggacgaa gtaccgaaag gtcttaccgg aaaactcgac gcaagaaaaa tcagaggat   4380
cctcataaag gccaagaagg gcggaaagat cgccgtgtaa ctcgagcata tgggctcgaa   4440
tttccccgat cgttcaaaca tttggcaata agtttcttta gattgaatc ctgttgccgg    4500
tcttgcgatg attatcatat aatttctgtt gaattacgtt aagcatgtaa taattaacat   4560
gtaatgcatg acgttattta tgagatgggt tttatgatt agagtcccgc aattatacat    4620
ttaatacgcg atagaaaaca aaatatagcg cgcaaactag gataaattat cgcgcgcggt   4680
gtcatctatg ttactagatc gggaattcaa gcttggcgta atcatggacc cagctttctt   4740
gtacaaagtg gggtacccgg ggatcctcta gcatatgctc gaggcggcc cagatatcag    4800
atctggtcga cggcatgcaa gcttggcgta atcatggcaa cttttattata catagttgat   4860
aattcactgg ccggataatt cactggccgt cgttttacaa cgactcagga tcctgtcaaa   4920
cactagtagt ttaaactgaa ggcgggaaac gacaatctga tcatgagcgg agaattaagg   4980
gagtcacgtt atgaccccgc cgatgacgcg ggacaagcc gttttacgtt tggaactgac   5040
agaaccgcaa cgttgaagga gccactcagc cgcgggtttc tggagtttaa tgagctaagc   5100
acatacgtca gaaaccatta ttgcgcgttc aaaagtcgcc taaggtcact atcagctagc   5160
aaatatttct tgtcaaaaat gctccactga cgttccataa attcccctcg gtatccaatt   5220
agagtctcat attcactctc aatccaaata atctgcaccg gatctggatc gtttcgcatg   5280
```

```
attgaacaag atggattgca cgcaggttct ccggccgctt gggtggagag gctattcggc   5340
tatgactggg cacaacagac aatcggctgc tctgatgccg ccgtgttccg gctgtcagcg   5400
caggggcgcc cggttctttt tgtcaagacc gacctgtccg gtgccctgaa tgaactgcag   5460
gacgaggcag cgcggctatc gtggctggcc acgacgggcg ttccttgcgc agctgtgctc   5520
gacgttgtca ctgaagcggg aagggactgg ctgctattgg gcgaagtgcc ggggcaggat   5580
ctcctgtcat ctcaccttgc tcctgccgag aaagtatcca tcatggctga tgcaatgcgg   5640
cggctgcata cgcttgatcc ggctacctgc ccattcgacc accaagcgaa acatcgcatc   5700
gagcgagcac gtactcggat ggaagccggt cttgtcgatc aggatgatct ggacgaagag   5760
catcagggc tcgcgccagc cgaactgttc gccaggctca aggcgcgcat gcccgacggc   5820
gaggatctcg tcgtgaccca tggcgatgcc tgcttgccga atatcatggt ggaaaatggc   5880
cgcttttctg gattcatcga ctgtggccgg ctgggtgtgg cggaccgcta tcaggacata   5940
gcgttggcta cccgtgatat tgctgaagag cttggcggcg aatgggctga ccgcttcctc   6000
gtgctttacg gtatcgccgc tcccgattcg cagcgcatcg ccttctatcg ccttcttgac   6060
gagttcttct gagcgggacc caagctctag atcttgctgc gttcggatat tttcgtggag   6120
ttcccgccac agaccggat gatccccgat cgttcaaaca tttggcaata aagtttctta   6180
agattgaatc ctgttgccgg tcttgcgatg attatcatat aatttctgtt gaattacgtt   6240
aagcatgtaa taattaacat gtaatgcatg acgttattta tgagatgggt ttttatgatt   6300
agagtcccgc aattatacat ttaatacgcg ataaaaaca aaatatagcg cgcaaactag   6360
gataaattat cgcgcgcggt gtcatctatg ttactagatc gggcctcctg tcaagctctg   6420
cttggtaata attgtcatta gattgttttt atgcatagat gcactcgaaa tcagccaatt   6480
ttagacaagt atcaaacgga tgttaattca gtacattaaa gacgtccgca atgtgttatt   6540
aagttgtcta agcgtcaatt tgtttacacc acaatatatc ctgccaccag cagccaaca   6600
gctcccccgac cggcagctcg gcacaaaatc accacgcgtt accaccaccg cggccggcc   6660
catggtgttg accgtgttcg ccggcattgc cgagttcgag cgttcccctaa tcatcgaccg   6720
cacccggagc gggcgcgagg ccgccaaggc ccgaggcgtg aagtttggcc cccgccctac   6780
cctcaccccg gcacagatcg cgcacgcccg cgagctgatc gacacggcgc gagcgcaccgt   6840
gaaagaggcg gctgcactgc ttggcgtgca tcgctcgacc ctgtaccgcg cacttgagcg   6900
cagcgaggaa gtgacgccca ccgaggccag gcggcgcggt gccttccgtg aggacgcatt   6960
gaccgaggcc gacgccctgg cggccgccga gaatgaacgc caagaggaac aagcatgaaa   7020
ccgcaccagg acggccagga cgaaccgttt ttcattaccg aagagatcga ggcggagatg   7080
atcgcggccg gtacgtgtt cgagccgccc gcgcacgtct caaccgtgcg gctgcatgaa   7140
atcctgccg gtttgtctga tgccaagctg cgggcctggc cggccagctt ggccgctgaa   7200
gaaaccgagc gccgccgtct aaaaaggtga tgtgtatttg agtaaaacag cttgcgtcat   7260
gcggtcgctg cgtatatgat gcgatgagta aataaacaaa tacgcaaggg gaacgcatga   7320
aggttatcgc tgtacttaac cagaaaggcg ggtcaggcaa gacgaccatc gcaacccatc   7380
tagcccgcgc cctgcaactc gccggggccg atgttctgtt agtcgattcc gatccccagg   7440
gcagtgcccg cgattgggcg gccgtgcggg aagatcaacc gctaaccgtt gtcggcatcg   7500
accgcccgac gattgaccgc gacgtgaagg ccatcggccg gcgcgacttc gtagtgatcg   7560
acggagcgcc caggcggcg gacttggctg tgtccgcgat caaggcagcc gacttcgtgc   7620
tgattccggt gcagccaagc ccttacgaca tatgggccac cgccgacctg gtggagctgg   7680
ttaagcagcg cattgaggtc acggatgaa ggctacaagc ggcctttgtc gtgtcgcggg   7740
cgatcaaagg cacgcgcatc ggcggtgagg ttgccgagcg gctggccggg tacgagctgc   7800
ccattcttga gtcccgtatc acgcagcgcg tgagctaccc tgagctgttc tgcgccggca   7860
caaccgttct tgaatcagaa cccgagggcg acgctgcccg cgaggtccag gcgctggcc   7920
ctgaaattaa atcaaaactc atttgagtta atgaggtaaa gagaaaatga gcaaaagcac   7980
aaacacgcta agtgccggcc gtccgagcgc acgcagcagc aaggctgcaa cgttggccag   8040
cctgcagac acgccagcca tgaagcgggt caactttcag ttgccggcgg aggatcacac   8100
caagctgaag atgtacgcgg tacgccaagc caagaccatt accgagctgc tatctgaata   8160
catcgcgcag ctaccagagt aaatgagcaa atgaataaat gagtagatga attttagcgg   8220
ctaaaggagg cggcatggaa aatcaagaac aaccaggcac cgacgccgtg gaatgcccca   8280
tgtgtggagga aacgggcgct tggccaggcg ggttgtctgc cggccctgca   8340
atggcactgg aaccccaag cccgaggaat cggcgtgagc ggtcgcaaac catccggccc   8400
ggtacaaatc ggcgcggcgc tgggtgatga cctggtggag aagttgaagg ccgcgcaggc   8460
cgcccagcgg caacgcatcg aggcagaagc acgcccccgt gaatcgtggc aagcggccgc   8520
tgatcgaatc cgcaaagaat cccggcaacc gccggcagcc ggtgcgccgt cgattaggaa   8580
gccgcccaag ggcgacgagc aaccagattt tttcgttccg atgctctatg acgtgggcac   8640
ccgcgatagt cgcagcatca tggacgtggc cgttttccgt ctgtcgaagc gtgaccgacg   8700
agctggcgag gtgatccgct acgagcttcc agacgggcac gtagaggttt ccgcagggcc   8760
ggccggcatg gccagtgtgt gggattacga cctggtactg atggcggttt cccatctaac   8820
cgaatccatg aaccgatacc gggaaggaa gggagacaaa cccgccgcg tgttccgtca   8880
acacgttgcg gacgtactca agttctgccg gcgagccgat ggcggaaagc agaaagacga   8940
cctggtagaa acctgcattc ggttaaacac cacgcacgtt gccatgcagc gtacgaagaa   9000
ggccaagaac ggccgcctgg tgacggtatc cgagggtgaa gccttgatta ccgctacaa   9060
gatcgtaaag agcgaaaccg ggcggccgga gtacatcgag atcgagctag ctgattggat   9120
gtaccgcgag atcacagaag gcaagaaccc ggacgtgctg acggttcacc ccgattactt   9180
tttgatcgat cccggcatcg gccgtttct ctaccgcctg gcacgccgcg ccgcaggcaa   9240
ggcagaagcc agatggttgt tcaagacgat ctacgaacgc agtggcagcg ccggagagtt   9300
caagaagttc tgtttccaccg tgcgcaagct gatcgggtca aatgacctgc cggagtacga   9360
tttgaaggag gaggcgggca ggctggccc gatcctagtc atgcgctacc gcaacctgat   9420
cgagggcgaa gcatccgccg gttcctaatg tacggagcag atgctaggc aaattgccct   9480
agcagggaaa aaggtcgaa aaggtctctt tcctgtggat agcacgtaca ttgggaaccc   9540
aaagccgtac attgggaacc ggaacccgta cattgggaac ccaaagccgt acattgggaa   9600
ccggtcacac atgtaagtga ctgatataaa agagaaaaaa ggcgattttt ccgcctaaaa   9660
ctctttaaaa cttattaaaa ctcttaaaac ccgcctgcaa tgtgcataag tgtctggcca   9720
gcgcacagcc gaaagctgc aaaaagcgcc taccttcgg tcgctgcgct ccctacgcc   9780
cgccgcttcg cgtcggccta tcgcggccgc tggccgctca aaaatggctg cctacggcc   9840
aggcaatcta ccagggcgcg acaagccgc ccgtcgcca ctcgaccgcc ggcgcccaca   9900
tcaaggcacc ctgcctcgcg cgtttcggtg atgacggtga aaacctctga cacatgcagc   9960
tcccggagac ggtcacagct tgtctgtaag cggatgccgg gagcagacaa gcccgtcagg  10020
```

-continued

```
gcgcgtcagc gggtgttggc ggtgtcggg gcgcagccat gacccagtca cgtagcgata   10080
gcggagtgta tactggctta actatgcggc atcagagcag attgtactga gagtgccacca  10140
tatgcggtgt gaaataccgc acagatgcgt aaggagaaaa taccgcatca ggcgctcttc   10200
cgcttcctcg ctcactgact cgctgcgctc ggtcgttcgg ctgcggcgag cggtatcagc   10260
tcactcaaag gcggtaatac ggttatccac agaatcaggg gataacgcag gaaagaacat   10320
gtgagcaaaa ggccagcaaa aggccaggaa ccgtaaaaag gccgcgttgc tggcgttttt   10380
ccataggctc cgcccccctg acgagcatca aaaaatcga cgctcaagtc agaggtggcg   10440
aaacccgaca ggactataaa gataccaggc gtttccccct ggaagctccc tcgtgcgctc   10500
tcctgttccg accctgccgc ttaccggata cctgtccgcc tttctccctt cgggaagcgt   10560
ggcgctttct catagctcac gctgtaggta tctcagttcg gtgtaggtcg ttcgctccaa   10620
gctgggctgt gtgcacgaac cccccgttca gcccgaccgc tgcgccttat ccggtaacta   10680
tcgtcttgag tccaacccgg taagacacga cttatcgcca ctggcagcag ccactggtaa   10740
caggattagc agagcgaggt atgtaggcgg tgctacagag ttcttgaagt ggtggcctaa   10800
ctacggctac actagaagga cagtatttgg tatctgcgct ctgctgaagc cagttacctt   10860
cggaaaaaga gttggtagct cttgatccgg caaacaaacc accgctggta gcggtggttt   10920
ttttgtttgc aagcagcaga ttacgcgcag aaaaaaagga tctcaagaag atcctttgat   10980
cttttctacg ggtctgacg ctcagtggaa cgaaaactca cgttaaggga ttttggtcat   11040
gcatgatata tctcccaatt tgtgtagggc ttattatgca cgcttaaaaa taataaaagc   11100
agacttgacc tgatagtttg gctgtgagca attatgtgct tagtgcatct aacgcttgag   11160
ttaagccgcg ccgcgaagcg gcgtcggctt aacgaatttc tagctagac attatttgcc   11220
gactaccttg gtgatctcgc cttttcacgta gtggacaaat tcttccaact gatctgcgcg   11280
cgaggccaag cgatcttctt cttgtccaag ataagcctgt ctagcttcaa gtatgacgag   11340
ctgatactgg gccggcaggc gctccattgc ccagtcggca gcgacatcct tcggcgcgat   11400
tttgccggtt actgcgctgt accaaatgcg ggacaacgta agcactacat ttcgctcatc   11460
gccagcccag tcgggcggcg agttccatag cgttaaggtt tcatttagcg cctcaaatag   11520
atcctgttca ggaaccggat caaagagttc ctccgccgct ggacctacca aggcaacgct   11580
atgttctctt gcttttgtca gcaagatagc cagatcaatg tcgatcgtgg ctggctcgaa   11640
gatacctgca agaatgtcat tgcgctgcca ttctccaaat tgcagttcgc gcttagctgg   11700
ataacgccac ggaatgatgt cgtcgtgcac aacaatggtg acttctacag cgcggagaat   11760
ctcgctctct ccaggggaag ccgaagtttc caaaaggtcg ttgatcaaag ctcgccgcgt   11820
tgtttcatca agccttacgg tcaccgtaac cagcaaatca atatcactgt gtggcttcag   11880
gccgccatcc actgcggagc cgtacaaatg tacggcagc aacgtcggtt cgagatggcg   11940
ctcgatgacg ccaactacct ctgatagttg agtcgatact tcggcgatca ccgcttcccc   12000
catgatgttt aactttgttt tagggcgact gccctgctgc gtaacatcgt tgctgctcca   12060
taacatcaaa catcgaccca cggcgtaacg cgcttgctgc ttggatgccc gaggcataga   12120
ctgtaccccca aaaaacagt cataacaagc catgaaaacc gccactgcgt tccatg       12176
```

SEQ ID NO: 62    moltype = DNA  length = 33
FEATURE          Location/Qualifiers
misc_feature     1..33
                 note = synthetic sequence
source           1..33
                 mol_type = other DNA
                 organism = synthetic construct
SEQUENCE: 62
aaaaaggtac catgacttcg aaagtttatg atc                                   33

SEQ ID NO: 63    moltype = DNA  length = 34
FEATURE          Location/Qualifiers
misc_feature     1..34
                 note = synthetic sequence
source           1..34
                 mol_type = other DNA
                 organism = synthetic construct
SEQUENCE: 63
aaattgagct cttattgttc atttttgaga actc                                  34

SEQ ID NO: 64    moltype = DNA  length = 14880
FEATURE          Location/Qualifiers
misc_feature     1..14880
                 note = vector sequence
source           1..14880
                 mol_type = other DNA
                 organism = synthetic construct
SEQUENCE: 64

```
gacatacaaa tggacgaacg gataaacctt ttcacgccct tttaaatatc cgattattct     60
aataaacgct ctttctcttt aggtttaccc gccaatatat cctgtcaaac actgatagtt    120
taaactgaag gcgggaaacg acaatcagat ctagtaggaa acagctatga ccatgattac    180
gccaagctat cgattacgcc aagctatcaa cttttgtatag aaaagttgca tcaagatctac   240
ggtgatgtag caagagctaa gttgtacttc gattcggttg acattactc gagaccagat    300
gttttacact tgaccgtaaa tgagcacccg aagaaaccgg tcacattcat ttcgaaggtg    360
gagaaagcgg aagatgactc aaacaagtaa tcggttgtga ttcgtcagtt catgtcactc    420
ctatgaagga gtcaagttca aatgttatgt tgagtttcaa acttttatg ctaaactttt    480
tttctttatt ttcgttaata atggaagaga accaattctc ttgtatctaa agattatcca   540
tctatcatcc aatttgagtg ttcaattctg gatgttgtgt taccctacat tctacaacca   600
tgtagccaat tattatgaat ctggctttga tttcagttgt gttctttcc tttttttctt   660
tgcatatttg catttagaat gtttaataat taagttactg tatttccaca tacattagtt   720
ccaagaatat acatatatta atttatttt cttaaaaatg ttttggaatg actaatattg   780
acaacgaaaa tagaagctat gctaaaccat tacgtatatg tgacttcaca tgttgttgtt   840
```

```
ttacattccc tatatatatg gatggctgtc acaatcagaa acgtgatcga aaaaagacaa    900
acagtgtttg cataaaaaga ctatttcgtt tcattgacaa tttgtgttta tttgtaaaga    960
aaagtggcaa agtggaattt gagttcctgc aagtaagaaa gatgaaataa aagacttgag   1020
tgtgtgtttt tttcttttat ctgaaagctg caatgaaata ttcctaccaa gcccgtttga   1080
ttattaattg gggtttggtt ttcttgatgc gaactaattg gttatataag aaactataca   1140
atccatgtta attcaaaaat tttgatttct cttgtaggaa tatgatttac tatatgagac   1200
tttcttttcg ccaataatag taaatccaaa gatatttgac cggaccaaaa cacattgatc   1260
tattttttag tttatttaat ccagtttctc tgagataatt cattaaggaa aacttagtat   1320
taacccatcc taagattaaa taggagccaa actcacattt caaatattaa ataacataaa   1380
atggatttaa aaaatctata cgtcaaattt tatttatgac atttcttatt taaatttata   1440
tttaatgaaa tacagctaag acaaaccaaa aaaaaatac tttctaagtg gtccaaaaca    1500
tcaattccgt tcaatattat taggtagaat cgtacgacca aaaaaggta ggttaatacg     1560
aattagaaac atatctataa catagtatat attattacct attatgagga atcaaaatgc   1620
atcaaaatatg gatttaagga atccataaaa gaataaattc tacgggaaaa aaaatggaat   1680
aaattcttt aagttttta tttgtttttt atttggtagt tctccatttt gttttatttc     1740
gtttggattt attgtgtcca aatactttgt aaaccaccgt tgtaattctt aaacggggtt   1800
ttcacttctt ttttatattc agacataaag catcggctgg tttaatcaat caatagattt   1860
tattttcctt ctcaattatt agtaggtttg atgtgaactt tacaaaaaaa acaaaaacaa   1920
atcaatgcag agaaaagaaa ccacgtgggc tagtcccacc ttgtttcatt tccaccacag   1980
gttcgatctt cgttaccgtc tccaatagga aaataaacgt gaccacaaaa aaaaaacaaa   2040
aaaaagtcta tatattgctt ctctcaagtc tctgagtgtc atgaaccaaa gtaaaaaaca   2100
aagactcgag tcaagtttgt acaaaaaagc aggctggtac cttaagaaat cctctcttct   2160
cctcttcatt ttcaaggtaa atctctctct ctctctctct ctctgttatt ccttgtttta   2220
attaggtatg tattattgct agtttgttaa tctgcttatc ttatgtatgc cttatgtgaa   2280
tatctttatc ttgttcatct catccgttta gaagctaaaa atttgttgat ttgactgtgt   2340
atctacacgt ggttatgttt atatctaatc agatatgaat ttcttcatat tgttgcgttt   2400
gtgtgtacca atccgaaatc gttgattttt ttcatttaat cgtgtagcta attgtacgta   2460
tacatatgga tctacgtatc aattgttcat ctgtttgtgt ttgtatgtat acagatctga   2520
aaacatcact tctctcatct gattgtgttg ttacatacat agatatagat ctgttatatc   2580
atttttttta ttaattgtgt atatatatat gtgcatagat ctggattaca tgattgtgat   2640
tatttacatg attttgttat ttacgtatgt atatatgtag atctggactt tttggagttg   2700
ttgacttgat tgtatttgtg tgtgtatatg tgtgttctga tcttgatatg ttatgtatgt   2760
gcagaccatg gaagacgcca aaaacataaa gaaaggcccg gcgccattct atccgctgga   2820
agatggaacc gctggagagc aactgcataa ggctatgaag agatacgccc tggttcctgg   2880
aacaattgct tttacagatg cacatatcga ggtggacatc acttacgctg agtacttcga   2940
aatgtccgtt cggttggcag aagctatgaa acgatatggg ctgaatacaa atcacagaat   3000
cgtcgtatgc agtgaaaact ctcttcaatt ctttatgccg gtgttgggcg cgttatttat   3060
cggagttgca gttgcgcccg cgaacgacat ttataatgaa cgtgaattgc tcaacagtat   3120
gggcatttcg cagcctaccg tggtgttcgt tccaaaaag gggttgcaaa aaatttgaa    3180
cgtgcaaaaa aagctcccaa tcatccaaaa aattattatc atggattcta aaacggatta   3240
ccagggattt cagtcgatgt acacgttcgt cacatctcat ctacctcccg gttttaatga   3300
atacgatttt gtgccagagt ccttcgatag ggacaagaca attgcactga tcatgaactc   3360
ctctggatct actggtctgc ctaaaggtgt cgctctgcct catagaactg cctgcgtcag   3420
attctcgcat gccagagatc ctatttttgg caatcaaatc attccggata ctgcgatttt   3480
aagtgttgtt ccattccatc acggttttgg aatgtttact acactcggat atttgatatg   3540
tggatttcga gtcgtcttaa tgtatagatt tgaagaagag ctgtttctga ggagccttca   3600
ggattacaag attcaaagtg cgctgctggt gccaacccta ttctccttct tcgccaaaag   3660
cactctgatt gacaaatacg atttatctaa tttacacgaa attgcttctg gtggcgctcc   3720
cctctctaag gaagtcgggg aagcggttgc caagaggttc catctgccag gtatcaggca   3780
aggatatggg ctcactgaga ctacatcagc tattctgatt acacccgagg ggatgaaaca   3840
accgggcgcg gtcggtaaag ttgttccatt tttgaagcg aaggttgtgg atctggatac    3900
cgggaaaacg ctgggcgtta atcaaagagg cgaactgtgt gtgagaggtc ctatgattat   3960
gtccggttat gtaaacaatc cggaagcgac caacgccttg attgacaagg atggatggct   4020
acattctgga gacatagctt actgggacga agacgaacac ttcttcatcg ttgaccgcct   4080
gaagtctctg attaagtaca aaggctatca ggtggctccc gctgaattgg aatccatctt   4140
gctccaacac cccaacatct tcgacgcagg tgtcgcaggt cttcccgacg atgacgccgg   4200
tgaacttccc gccgccgttg ttgttttgga gcacggaaaa acgatgacgg aaaaagagat   4260
cgtggattac gtcgccagtc aagtaacaac cgcgaaaaag ttgcgcggag gagttgtgtt   4320
tgtggacgaa gtaccgaaag gtcttaccgg aaaactcgac gcaagaaaaa tcagagagat   4380
cctcataaag gccaagaagg gcggaaagat cgccgtgtaa ctcgagcata tgggctcgaa   4440
tttccccgat cgttcaaaca tttggcaata aagtttctta agattgaatc ctgttgccgg   4500
tcttgcgatg attatcatat aatttctgtt gaattacgtt aagcatgtaa taattaacat   4560
gtaatgcatg acgttattta tgagatgggt ttttatgatt agagtcccgc aattatacat   4620
ttaatacgcg atagaaaaca aaatatagcg cgcaaactag gataaattat cgcgcgcggt   4680
gtcatctatg ttactagatc gggaattcaa gcttggcgta atcatggacc agctttctt    4740
gtacaaagtg gggtaccaat tcgaatccaa aaattacgga tatgaatata ggcatatccg   4800
tatccgaatt atccgtttga cagctagcaa cgattgtaca attgcttctt taaaaaagga   4860
agaagaaag aaagaaaaga atcaacatca gcgttaacaa acggcccgt tacggcccaa     4920
acggtcatat agagtaacgg cgttaagcgt tgaaagctc ctatcgaaat acgtaaccgc    4980
aaacgtgtca tagtcagatc ccctcttcct tcaccgcctc aaacacaaaa ataatcttct   5040
acagcctata tatacaaccc ccccttctat ctctcctttc tcacaattca tcatctttct   5100
ttctctaccc ccaattttaa gaaatcctct cttctcctct tcattttcaa ggtaaatctc   5160
tctctctctc tctctctctg ttattccttg ttttaattag gtatgtatta ttgctagttt   5220
gttaatctgc ttatctattg tgccttat catcttgtt catctcatcc                5280
gtttagaagc tataaatttg ttgatttgac tgtgtatcta cacgtggtta tgtttatatc   5340
taatcagata tgaatttctt catattgttg cgtttgtgtg taccaatccg aaatcgttga   5400
tttttttcat ttaatcgtgt agctaattgt acgtatacat atggatctac gtatcaattg   5460
ttcatctgtt tgtgtttgta tgtatacaga tctgaaaaca tcacttctct catctgattg   5520
tgttgttaca tacatagata tagatctgtt atatcatttt ttttattaat tgtgtatata   5580
```

```
tatatgtgca tagatctgga ttacatgatt gtgattattt acatgattt gttatttacg    5640
tatgtatata tgtagatctg gacttttgg agttgttgac ttgattgtat ttgtgtgtgt    5700
atatgtgtgt tctgatcttg atatgttatg tatgtgcagc tgaaccatgg cggcggcaac   5760
aacaacaaca acaacatctt cttcgatctc cttctccacc aaaccatctc cttcctcctc   5820
caaatcacca ttaccaatct ccagattctc cctcccattc tccctaaacc ccaacaaatc   5880
atcctcctcc tcccgccgcc gcggtatcaa atccagctct ccctcctcca tctccgccgt   5940
gctcaacaca accaccaatg tcacaaccac tccctctcca accaaaccta ccaaacccga   6000
aacattcatc tcccgattcg ctccagatca accccgcaaa ggcgctgata tcctcgtcga   6060
agctttagaa cgtcaaggcg tagaaaccgt attcgcttac cctggaggta catcaatgga   6120
gattcaccaa gccttaaccc gctcttcctc aatccgtaac gtccttcctc gtcacgaaca   6180
aggaggtgta ttcgcagcag aaggatacgc tcgatcctca ggtaaaccag gtatctgtat   6240
agccacttca ggtcccggag ctacaaatct cgttagcgga ttagccgatg cgttgttaga   6300
tagtgttcct cttgtagcaa tcacaggaca agtccctcgt cgtatgattg gtacagatgc   6360
gtttcaagag actccgattg ttgaggtaac gcgttcagct acgaagcata actatcttgt   6420
gatggatgtt gaagatatcc ctaggattat tgaggaagct ttctttttag ctacttctgg   6480
tagacctgga cctgttttgg ttgatgttcc taaagatatt caacaacagc ttgcgattcc   6540
taattgggaa caggctatga gattacctgg ttatatgtct aggatgccta aacctccgga   6600
agattctcat ttggagcaga ttgttaggtt gatttctgag tctaagaagc ctgtgttgta   6660
tgttggtggt ggttgtttga attctagcga tgaattgggt aggtttgttg agcttacggg   6720
gatccctgtt gcgagtacgt tgatggggct gggatcttat ccttgtgatg atgagttgtc   6780
gttacatatg cttggaatgc atgggactgt gtatgcaaat tacgctgtgg agcatagtga   6840
tttgttgttg gcgtttgggg taaggtttga tgatcgtgtc acgggtaagc ttgaggcttt   6900
tgctagtagg gctaagattg ttcatattga tattgactcg gctgagattg ggaagaataa   6960
gactcctcat gtgtctgtgt gtggtgatgt taagctggct ttgcaaggga tgaataaggt   7020
tcttgagaac cgagcggagg agcttaagct tgattttgga gtttggagga atgagttgaa   7080
cgtacagaaa cagaagtttc cgttgagctt taagacgttt ggggaagcta ttcctccaca   7140
gtatgcgatt aaggtccttg atgagttgac tgatggaaaa gccataataa gtactggtgt   7200
cgggcaacat caaatgtggg cggcgcagtt ctacaattac aagaaaccaa ggcagtggct   7260
atcatcagga ggccttggag ctatgggatt tggacttcct gctgcgattg gagcgtctgt   7320
tgctaacct gatgcgatag ttgtggatat tgacgggagt ggaagcttta taatgaatgt   7380
gcaagagcta gccactattc gtgtagagaa tcttccagtg aaggtacttt tattaaacaa   7440
ccagcatctt ggcatggtta tgcaatggga agatcggttc tacaaagcta accgagctca   7500
cacatttctc ggggatccgg ctcaggagga cgagatattc ccgaacatgt tgctgtttgc   7560
agcagcttgc gggattccag cggcgagggt gacaaagaaa gcagatctcc gagaagctat   7620
tcagacaatg ctggatacac caggacctta cctgttggat gtgatttgtc cgcaccaaga   7680
acatgtgttg ccgatgatcc cgaatggtgg cactttcaac gatgtcataa cggaaggaga   7740
tggccggatt aaatactgag agatgaaacc ggtgattatc agaacttttt atggtctttg   7800
tatgcatatg gtaaaaaaac ttagtttgca atttcctgtt tgttttggta atttgagttt   7860
cttttagttg ttgatctgcc tgctttttgg tttacgtcag actactactg ctgttgttgt   7920
ttggtttcct ttctttcatt ttataaataa ataatccggt tcggtttact ccttgtgact   7980
ggctcagttt ggttattgcg aaatgcgaat ggtaaattga gtaattgaaa ttcgttatta   8040
gggttctaag ctgttttaac agtcactggg ttaatatctc tcgaatcttg catggaaaat   8100
gctcttacca ttggttttta attgaaatgt gctcatatgg gccgtggttt ccaaattaaa   8160
taaaactacg atgtcatcga gaagtaaaat caactgtgtc cacattatca gttttgtgta   8220
tacgatgaaa tagggtaatt caaaatctag cttgatatgc cttttggttc attttaacct   8280
tctgtaaaca tttttttcaga ttttgaacaa gtaaatccaa aaaaaaaaaa aaaaatctc   8340
aactcaacac taaattttt taatgtataa aagatgctta aacatttgg cttaaaagaa    8400
agaagctaaa aacatagaga actcttgtaa attgaagtat gaaaatatac tgaattgggt   8460
attatatgaa ttttttctgat ttaggattca catgatccaa aaaggaaatc cagaagcact   8520
aatcagacat tggaagtagg aatatttcaa aaagttttt ttttttaagt aagtgacaaa     8580
agcttttaaa aaatagaaaa gaaactagta ttaaagtttgt aaattaata aacaaaagaa    8640
atttttata tttttcatt tctttttcca gcatgaggtt atgatggcag gatgtggatt      8700
tcattttttt cctttgata gccttttaat tgatctatta taattgacga aaaaatatta    8760
gttaattata gatatatttt aggtagtatt agcaattac acttccaaaa gactatgtaa    8820
gttgtaaata tgatgcgttg atctcttcat cattcaatgg ttagtcaaaa aaataaaagc   8880
ttaactagta aactaaagta gtcaaaaatt gtactttagt ttaaatatt acatgaataa    8940
tccaaaacga catttatgtg aaacaaaaac aatatctaga gtcgacttaa ttaaactagt   9000
ggcgcgccaa ttgactagta ggcctatcga ttaattaagg ccgcctcgag catatgggca   9060
tgcaagcttg gcgtaatcat ggcaacttta ttatacatag ttgataattc actggccgta   9120
tctgcttggt aataattgtc attagattgt ttttatgcat agatgcactc gaaatcagcc   9180
aattttagac aagtatcaaa cggattgaa ttcagtacat taaagacgtc cgcaatgtgt    9240
tattaagttg tctaagcgtc aatttgttta caccacaata tatcctgcca ccagccagcc   9300
aacagctccc cgaccggcag ctcggcacaa aatcaccacg cgttaccacc acgccggccg   9360
gccgcatggt gttgaccgtg ttcgccggca ttgccgttcc ctaatcattg   9420
accgcacccg gagcgggcgc gaggccgcca aggcccgagg cgtgaagttt ggcccccgcc   9480
ctaccctcac cccggcacag atcgcgcacg cccgcgagct gatcgaccag gaaggccgca   9540
ccgtgaaaga ggcggctgca ctgcttggcg tgcatcgctc gaccctgtac cgcgcacttg   9600
agcgcagcga ggaagtgacg cccaccgagg ccaggcggcc cggtgccttc cgtgaggacg   9660
cattgaccga ggccgacgcc ctggccgccg ccgagaatga acgccaagag gaacaagcat   9720
gaaaccgcac caggacgcc aggacgaacc gttttcatt accgaagaga tcgaggcgga     9780
gatgatcgcg gccgggtacg tgttcgagcc gcccgcgcac gtctcaaccg tgcggctgca   9840
tgaaatcctg gccggtttgt ctgatgccaa gctggcggcc tggccggcca gcttggccgc   9900
tgaagaaacc gagcgccgcc gtctaaaaag gtgatgtgta tttgagtaaa acagcttgcg   9960
tcatgcggtc gctgcgtata tgatgcgatg agtaaataaa caaatacgca agggaaacgc  10020
atgaaggtta tcgctgtact taaccagaaa ggcgggtcag gcaagacgac catcgcaacc  10080
catctagccc gcgccctgca actcgccggg gccgatgttc tgttagtcga ttccgatccc  10140
cagggcagtg cccgcgattg gcggccgtg cgggaagatc aaccgctaac cgttgtcggc    10200
atcgaccgcc cgacgattga ccgcgacgtg aaggccatcg gccggcgcga cttcgtagtg  10260
atcgacggag cgccccaggc ggcggacttg gctgtgtccg cgatcaaggc agccgacttc  10320
```

```
gtgctgattc cggtgcagcc aagcccttac gacatatggg ccaccgccga cctggtggag   10380
ctggttaagc agcgcattga ggtcacggat ggaaggctac aagcggcctt tgtcgtgtcg   10440
cgggcgatca aaggcacgcg catcggcggt gaggttgccg aggcgctggc cgggtacgag   10500
ctgcccattc ttgagtccg tatcacgcag cgcgtgagct acccaggcac tgccgccgcc   10560
ggcacaaccg ttcttgaatc agaacccgag ggcgacgcts cccgcgaggt ccaggcgctg   10620
gccgctgaaa ttaaatcaaa actcatttga gttaatgagg taaagagaaa atgagcaaaa   10680
gcacaaacac gctaagtgcc ggccgtccga gcgcacgcag cagcaaggct gcaacgttgg   10740
ccagcctggc agacacgcca gccatgaagc gggtcaactt tcagttgccg gcggaggatc   10800
acaccaagct gaagatgtac gcggtacgcc aaggcaagac cattaccgga ctgctatctg   10860
aatacatcgc gcagctacca gagtaaatga gcaaatgaat aaatgagtag atgaatttta   10920
gcggctaaag gaggcggcat ggaaaatcaa gaacaaccag gcaccgacgc cgtgaatgc    10980
cccatgtgtg gaggaacggg cggttggcca ggcgtaagcg gctgggttgt ctgccggccc   11040
tgcaatggca ctggaacccc caagcccgag gaatcggcgt gagcggtcgc aaaccatccg   11100
gcccgtaca  aatcggcgcg gcgctgggtg atgacctggt ggagaagttg aaggccggcc   11160
aggccgccca gcggcaacgc atcgaggcag aagcacgccc cggtgaatcg tggcaagcgg   11220
ccgctgatcg aatccgcaaa gaatcccggc aaccgccggc agccggtgcg ccgtcgatta   11280
ggaagccgcc caagggcgac gagcaaccag attttttcgt tccgatgctc tatgacgtgg   11340
gcaccgcga  tagtcgcagc atcatggacg tggccgtttt ccgtctgtcg aagcgtgacc   11400
gacgagctgg cgaggtgatc cgctacgagc ttccagacgg gcacgtagag gtttccgcag   11460
ggccggccgg catggccagt gtgtgggatt acgacctggt actgatgcg  gtttcccatc   11520
taaccgaatc catgaaccga taccggggaag ggaagggaga caagcccggc cgcgtgttcc   11580
gtccacacgt tgcggacgta ctcaagttct gccggcgagc cgatggggga aagcagaaag   11640
acgacctggt agaaacctgc attcggttaa acaccacgca cgttgccatg cagcgtacga   11700
agaaggccaa gaacgccgc  ctggtgacgg tatccgaggg tgaagccttg attagccgct   11760
acaagatcgt aaagagcgaa accgggcggc cggagtacat cgagatcgag ctagctgatt   11820
ggatgtaccg cgagatcaca gaaggcaaga acccggacgt gctgacggtt caccccgatt   11880
acttttttgat cgatcccggc atcggccgtt ttctctaccg cctggcacgc cgcgccgcag   11940
gcaaggcaga agccagatgg ttgttcaaga cgatctacga acgcagtggc agcgccggag   12000
agttcaagaa gttctgtttc accgtgcgca agctgatcgg gtcaaatgac ctgccggagt   12060
acgattttgaa ggaggaggcg gggcaggctg gcccgaatcc agtcatgcgc taccgcaacc   12120
tgatcgaggg cgaagcatcc gccggttcct aatgtacgga gcagatgcta gggcaaattg   12180
ccctagcagg ggaaaaaggt cgaaaaggtc tctttcctgt ggatagcacg tacattggga   12240
acccaaagcc gtacattggg aaccggaacc cgtacattgg gaacccaaag ccgtacattg   12300
ggaaccggtc acacatgtaa gtgactgata taaaagagaa aaaaggcgat ttttccgcct   12360
aaaactcttt aaaacttatt aaaactctta aaacccgcct ggcctgtgca taactgtctg   12420
gccagcgcac agccgaagag ctgcaaaaag cgcctaccct tcggtcgctg cgctccctac   12480
gccccgccgc ttcgcgtcgg cctatcgcgg ccgctggccg ctcaaaaatg gctggcctac   12540
ggccaggcaa tctaccaggg gcggacaag  ccgcgccgtc gccactcgac cgccggcgcc   12600
cacatcaagg caccctgcct cgcgcgtttc ggtgatgacg gtgaaaacct ctgacacatg   12660
cagctcccgg agacggtcac agcttgtctg taagcggatg ccgggagcag acaagcccgt   12720
cagggcgcgt cagcgggtgt tggcgggtgt cggggcgcag ccatgaccca gtcacgtagc   12780
gatagcggag tgtatactgg cttaactatg cggcatcaga gcagattgta ctgagagtgc   12840
accatatgcg gtgtgaaata ccgcacagat gcgtaaggag aaaataccgc atcaggcgct   12900
cttccgcttc ctcgctcact gactcgctgc gctcggtcgt tcggctgcgg cgagcggtat   12960
cagctcactc aaaggcggta atacggttat ccacagaatc aggggataac gcaggaaaga   13020
acatgtgagc aaaaggccag caaaaggcca ggaaccgtaa aaaggccgcg ttgctggcgt   13080
ttttccatag gctccgcccc cctgacgagc atcacaaaaa tcgacgctca agtcagaggt   13140
ggcgaaaccc gacaggacta taaagatacc aggcgtttcc ccctggaagc tccctcgtgc   13200
gctctcctgt tccgaccctg ccgcttaccg gatacctgtc cgcctttctc ccttcgggaa   13260
gcgtggcgct ttctcatagc tcacgctgta ggtatctcag ttcggtgtag gtcgttcgct   13320
ccaagctggg ctgtgtgcac gaaccccccg ttcagcccga ccgctgcgcc ttatccggta   13380
actatcgtct tgagtccaac ccggtaagac acgacttatc gccactggca gcagccactg   13440
gtaacaggat tagcagagcg aggtatgtag gcggtgctac agagttcttg aagtggtggc   13500
ctaactacgg ctacactaga aggacagtat ttggtatctg cgctctgctg aagccagtta   13560
ccttcggaaa aagagttggt agctcttgat ccggcaaaca aaccaccgct ggtagcggtg   13620
gtttttttgt ttgcaagcag cagattacgc gcagaaaaaa aggatctcaa gaagatcctt   13680
tgatctttc  tacggggtct gacgctcagt ggaacgaaaa ctcacgttaa gggattttgg   13740
tcatgcatga tatatctccc aatttgtgta gggcttatta tgcacgctta aaaataataa   13800
aagcagactt gacctgatag tttggctgtg agcaattatg tgcttagtgc atctaacgct   13860
tgagttaagc cgcgccgcga agcggcgtcg gcttgaacga atttctagct agacattatt   13920
tgccgactac cttggtgatc tcgcctttca cgtagtggac aaattcttcc aactgatctg   13980
cgcgcgaggc caagcgatct tcttcttgtc caagataagc ctgtctagct tcaagtatga   14040
cgggctgata ctgggccggc aggcgctcca ttgcccagtc ggcagcgaca tccttcggcg   14100
cgattttgcc ggttactgcg ctgtaccaaa tgcgggacaa cgtaagcact acatttcgat   14160
catcgccagc ccagtcgggc ggcgagttcc atagcgttaa ggtttcattt agcgcctcaa   14220
atagatcctg ttcaggaacc ggatcaaaga gttcctccgc cgctggacct accaaggcaa   14280
cgctatgttc tcttgctttt gtcagcaaga tagccagatc aatgtcgatc gtggctggct   14340
cgaagatacc tgcaagaatg tcattgcgct gccattctcc aaattgcagt tcgcgcttag   14400
ctggataacg ccacggaatg atgtcgtcgt gcacaacaat ggtgacttct acagcgcgga   14460
gaatctcgct ctctccaggg gaagccgaag tttccaaaag gtcgttgatc aaagctcgcc   14520
gcgttgtttc atcaagcctt acggtcaccg taaccagcaa atcaatatca ctgtgtggct   14580
tcaggccgcc atccactgcg gagccgtaca aatgtacggc cagcaacgtc ggttcgagat   14640
ggcgctcgat gacgccaact acctctgata gttgagtcga tacttcggcg atcaccgctt   14700
ccccccatgat gtttaacttt gttttagggc gactgccctg ctgcgtaaca tcgttgctgc   14760
tccataacat caaacatcga cccacgcgcgt aacgcgcttg ctgcttggat gcccgaggca   14820
tagactgtac cccaaaaaaa cagtcataac aagccatgaa aaccgccact gcgttccatg   14880

SEQ ID NO: 65    moltype = DNA  length = 39
FEATURE          Location/Qualifiers
```

```
misc_feature            1..39
                        note = synthetic sequence
source                  1..39
                        mol_type = other DNA
                        organism = synthetic construct
SEQUENCE: 65
tttttggcgc gcctttctct cgttctcatc tttctctct                           39

SEQ ID NO: 66           moltype = DNA  length = 38
FEATURE                 Location/Qualifiers
misc_feature            1..38
                        note = synthetic sequence
source                  1..38
                        mol_type = other DNA
                        organism = synthetic construct
SEQUENCE: 66
taataggcgc gcctttgtca aacttttgat tgtcacct                            38

SEQ ID NO: 67           moltype = DNA  length = 36
FEATURE                 Location/Qualifiers
misc_feature            1..36
                        note = synthetic sequence
source                  1..36
                        mol_type = other DNA
                        organism = synthetic construct
SEQUENCE: 67
tatatggcgc gccaaatcgt tctttcaaat ctctca                              36

SEQ ID NO: 68           moltype = DNA  length = 37
FEATURE                 Location/Qualifiers
misc_feature            1..37
                        note = synthetic sequence
source                  1..37
                        mol_type = other DNA
                        organism = synthetic construct
SEQUENCE: 68
ttataggcgc gcctctgtaa ttcacaaaaa actgaga                             37

SEQ ID NO: 69           moltype = DNA  length = 36
FEATURE                 Location/Qualifiers
misc_feature            1..36
                        note = synthetic sequence
source                  1..36
                        mol_type = other DNA
                        organism = synthetic construct
SEQUENCE: 69
tttttggcgc gccttagatc tcgtgccgtc gtgcga                              36

SEQ ID NO: 70           moltype = DNA  length = 33
FEATURE                 Location/Qualifiers
misc_feature            1..33
                        note = synthetic sequence
source                  1..33
                        mol_type = other DNA
                        organism = synthetic construct
SEQUENCE: 70
tttttggcgc gcctttgatc aagcctgttc aca                                 33

SEQ ID NO: 71           moltype = DNA  length = 36
FEATURE                 Location/Qualifiers
misc_feature            1..36
                        note = synthetic sequence
source                  1..36
                        mol_type = other DNA
                        organism = synthetic construct
SEQUENCE: 71
aaaaaggcgc gcctcatcag atcttcaaaa ccccaa                              36

SEQ ID NO: 72           moltype = DNA  length = 40
FEATURE                 Location/Qualifiers
misc_feature            1..40
                        note = synthetic sequence
source                  1..40
                        mol_type = other DNA
                        organism = synthetic construct
SEQUENCE: 72
aaaaaggcgc gcctgatttg agggtagtac taaccgggaa                          40

SEQ ID NO: 73           moltype = DNA  length = 36
```

| FEATURE | Location/Qualifiers |
|---|---|
| misc_feature | 1..36 |
| | note = synthetic sequence |
| source | 1..36 |
| | mol_type = other DNA |
| | organism = synthetic construct |

SEQUENCE: 73

```
tttttttggcg cgccttaaga aatcctctct tctcct         36
```

| SEQ ID NO: 74 | moltype = DNA  length = 36 |
|---|---|
| FEATURE | Location/Qualifiers |
| misc_feature | 1..36 |
| | note = synthetic sequence |
| source | 1..36 |
| | mol_type = other DNA |
| | organism = synthetic construct |

SEQUENCE: 74

```
tttttttggcg cgcctctgca catacataac atatca          36
```

| SEQ ID NO: 75 | moltype = DNA  length = 14019 |
|---|---|
| FEATURE | Location/Qualifiers |
| misc_feature | 1..14019 |
| | note = vector sequence |
| source | 1..14019 |
| | mol_type = other DNA |
| | organism = synthetic construct |

SEQUENCE: 75

```
gtgattttgt gccgagctgc cggtcgggga gctgttggct ggctggtggc aggatatatt    60
gtggtgtaaa caaattgacg cttagacaac ttaataacac attgcggacg tctttaatgt   120
actgaattta gttactgatc actgattaag tactgatatc ggtaccaagc ttccgcggct   180
gcagtgcagc gtgacccggt cgtgcccctc tctagagata atgagcattg catgtctaag   240
ttataaaaaa ttaccacata ttttttttgt cacacttgtt tgaagtgcag tttatctatc   300
tttatacata tatttaaact ttactctacg aataatataa tctatagtac tacaataata   360
tcagtgtttt agagaatcat ataaatgaac agttagacat ggtctaaagg acaattgagt   420
attttgacaa caggactcta cagttttatc tttttagtgt gcatgtgttc tccttttttt   480
ttgcaaatag cttcacctat ataatacttc atccattta ttagtacatc catttagggt   540
ttaggggttaa tggttttat agactaattt ttttagtaca tctattttat tctattttag   600
cctctaaatt aagaaaacta aaactctatt ttagtttttt tatttaatag tttagatata   660
aaatagaata aaataaagtg actaaaaatt aaacaaatac cctttaagaa attaaaaaaa   720
ctaaggaaac atttttcttg tttcgagtag ataatgccag cctgttaaac gccgtcgacg   780
agtctaacgg acaccaacca gcgaaccagc agcgtcgcgt cgggccaagc gaagcagacg   840
gcacggcatc tctgtcgctg cctctggacc cctctcgaga gttccgctcc accgttggac   900
ttgctccgct gtcggcatcc agaaattgcg tggcggaggcg agagacgtga gccggcacgg   960
caggcggcct cctcctcctc tcacggcacc ggcagctacg ggggattcct ttcccaccgc  1020
tccttcgctt tccccttcctc gcccgccgta ataaatagac ccccctcca caccctcttt  1080
ccccaacctc gtgttgttcg gagcgcacac acacaacc agatctcccc caaatccacc  1140
cgtcggcacc tccgcttcaa ggtacgccgc tcgtcctccc ccccccccc cctctctacc  1200
ttctctagat cggcgttccg gtccatggtt agggcccggt agttctactt ctgttcatgt  1260
ttgtgttaga tccgtgtttg tgttagatcc gtgctgctag cgtcgtaca cggatgcgac  1320
ctgtacgtca gacacgttct gattgctaac ttgccagtgt ttctctttgg ggaatcctgg  1380
gatggctcta gccgttccgc agacgggatc gatttcatga tttttttgt ttcgttgcat  1440
agggttttggt ttgccctttt ccttttatttc aatatatgcc gtgcacttgt ttgtcggtc  1500
atcttttcat gcttttttt gtcttggttg tgatgatgtg gtctggttgg gcggtcgttc  1560
tagatcggag tagaattctg tttcaaacta cctggtggat ttattaattt tggatctgta  1620
tgtgtgccc atacatattc atagttacga attgaagatg atggatggaa atatcgatct  1680
aggataggta tacatgttga tgcgggtttt actgatgcat atacagagat gcttttttgtt  1740
cgcttggttg tgatgatgtg gtgtggttgg gcggtcgttc attcgttcta gatcggagta  1800
gaatactgtt tcaaactacc tggtgtattt attaattttg gaactgtatg tgtgtgtcat  1860
acatcttcat agttacgagt ttaagatgga tggaaatatc gatctaggat aggtatacat  1920
gttgatgtgg gttttactga tgcatataca tgatggcata tgcagcatct attcatatgc  1980
tctaaccttg agtaccatc tattataata aacaagtatg ttttataatt atttcgatct  2040
tgatatactt ggatgatggc atatgcagca gctatatgtg gatttttta gccctgcctt  2100
catacgctat ttattttgctt ggtactgttt cttttgtcga tgctcaccct gttgtttggt  2160
gttacttctg cagcccgggg gatccactag ttctagaaac cggccaccgc gccgcggcg  2220
cgtctaccgc gctcactggc gccactaccg ctgcgcccaa ggcgaggcgc cgggcgcacc  2280
tcctggccac ccgcgcgcc ctcgccgcgc ccatcaggtg ctcagcggcg tcacccgcca  2340
tgccgatggc tccccggcc acccgctcc ggccgtgggg ccaccgat cccgcaagg   2400
gcgccgacat cctcgtcgag tccctcgagc gctgcggcgt ccgcgacgtc ttcgcctacc  2460
ccggcggcac gtccatggag atccaccagg cactcaaccc gctccccgtc atcgccaacg  2520
acctcttccg ccacgagcaa ggggaggcct ttgcggcctc cggctacgcg cgctcctcgg  2580
gccgcgtcgg cgtctgcatc gccacctccg gcccggcgc caccaacctt gtctccgcgc  2640
tcgccgacgc gctgctcgat tcgtcccca tggtcgccat cacgggacag gtgccgcgac  2700
gcatgattgg caccgcgcc ttccaggaga cgcccatcgt cgaggtcacc cgctccatca  2760
ccaagcacaa ctacctggtc ctcgacgtcg acgacatcc cgcgtcgtg caggaggctt  2820
tcttcctcgc ctcctctggt cgaccgggc cggtgcttgt cgacatcccc aaggacatcc  2880
agcagcagat ggcggtgcct gtctgggaca agcccatgag tctgcctggg tacattgcgc  2940
gccttcccaa gccccctgcg actgagttgc ttgagcaggt gctgcgtctt gttggtgaat  3000
cccggcgccc tgttctttat gttggcgtg gctgcgcagc atctggtgag gagttgcgac  3060
gctttgtgga gctgactgga atcccggtca caactactct tatgggcctc ggcaacttcc  3120
```

```
ccagcgacga cccactgtct ctgcgcatgc taggtatgca tggcacggtg tatgcaaatt   3180
atgcagtgga taaggccgat ctgttgcttg cacttggtgt gcggtttgat gatcgtgtga   3240
cagggaagat tgaggctttt gcaagcaggg ctaagattgt gcacgttgat attgatccgg   3300
ctgagattgg caagaacaag cagccacatg tgtccatctg tgcagatgtt aagcttgctt   3360
tgcagggcat gaatgctctt cttgaaggaa gcacatcaaa gaagagcttt gactttggct   3420
catggaacga tgagttggat cagcagaaga gggaattccc ccttgggtat aaaacatcta   3480
atgaggagat ccagccacaa tatgctattc aggttcttga tgagctgacg aaaggcgagg   3540
ccatcatcgg cacaggtgtt gggcagcacc agatgtgggc ggcacagtac tacacttaca   3600
agcggccaag gcagtggttg tcttcagctg gtcttgggc tatgggattt ggtttgccgg   3660
ctgctgctgg tgcttctgtg gccaacccag gtgttactgt tgttgacatc gatggagatg   3720
gtagctttct catgaacgtt caggagctag ctatgatccg aattgagaac ctcccggtga   3780
aggtctttgt gctaaacaac cagcacctgg ggatggtggt gcagtgggag gacaggttct   3840
ataaggccaa cagagcgcac acatacttgg gaaacccaga gaatgaaagt gagatatatc   3900
cagatttcgt gacgatcgcc aaagggttca acattccagc ggtccgtgtg acaaagaaga   3960
acgaagtccg cgcagcgata agaagatgc tcgagactcc agggccgtac ctcttggata   4020
taatcgtccc acaccaggag catgtgttgc ctatgatccc taatggtggg gctttcaagg   4080
atatgatcct ggatggtgat ggcaggactg tgtactgatc taaaatccag caagcaactg   4140
atctaaaatc cagcaagcac cgcctccctg ctagtacaag ggtgatatgt ttttatctgt   4200
gtgatgttct cctgtattct atcttttttt gtaggccgtc agctatcgt tatggtaatc   4260
ctatgtagct tccgaccttg taattgtgta gtctgttgtt ttccttctgg catgtgtcat   4320
aagagatcat ttaagtgcct tttgctacat ataaataaga taataagcac tgctatgcag   4380
tggttctgaa ttggcttctg ttgccaaatt taagtgtcca actggtcctt gcttttgttt   4440
tcgctatttt tttcctttt tagttattat tatattggta atttcaactc aacatatgat   4500
gtatggaata atgctagggc tgcaatttca aactattta caaccagaa tggcattttc   4560
gtggtttgag gggagtgaaa aaaaatgagg catttgactg aattagttac ctgatccatt   4620
ttcgtggttt ggatcattgg aattaaattc cattctaata atagtaattt tggcatatat   4680
caattaagtt aattcggttt tatgcaaaat atatttgtat actattatta tcaagatgtc   4740
ggagatattt atatgctaca ttttttactat acaggagtga gatgaagagt gtcatgtaag   4800
ttacacagta gaaacaaatt ctattaatgc ataaaatcat ttccatcatc caccctatga   4860
atttgagata gacctatatc taaactttga aaagtggttta aatatcaaat tccaaattaa   4920
ataagttatt ttattgagtg aattctaatt tctctaaaac gaagggatct aaacgccctc   4980
taaagctaat ttggaaactc aaactttctt agcattggag gggattgaga aaaaatatta   5040
attcattttc atctcaatca ttcaatctcc aaagagattt gagttcctta ttagtctgtt   5100
ccatgcatca aatcggctca atgtgtcatt atttgccatg acgattgacg agttgttctg   5160
gggcctagcg ctttccacgc cgatgtgctg gggcctggtc ctggagaaga cagcttgata   5220
tttaaagcta tcaattgttt caattgattc ccacttcatt tttctaaatg tagaaaacgg   5280
tgacgtataa gaaaaagaat gaattaggac ttttattccg tacactaatc tagagcggcc   5340
caagcttgta cactagtacg cgtcaattga tttaaattta attaatgcag tgcagcgtga   5400
cccggtcgtg cccctctcta gagataatga gcattgcatg tctaagttat aaaaaattac   5460
cacatatttt ttttgtcaca cttgtttgaa gtgcagttta tctatcttta tacatatatt   5520
taaactttac tctacgaata atataatcta tagtactaca ataatatcag tgttttagag   5580
aatcatataa atgaacagtt agacatggtc taaaggacaa ttgagtattt tgacaacagg   5640
actctacagt tttatctttt tagtgtgcat gtgttctcct tttttttgc aaatagcttc   5700
acctatataa tacttcatcc attttattag tacatccatt tagggtttag ggttaatggt   5760
ttttatagac taattttttt agtacatcta ttttattcta tttagcctc taaattaaga   5820
aaactaaaac tctattttag ttttttttatt taatagttta gatataaaat agaataaaat   5880
aaagtgacta aaaattaaac aaatacccctt taagaaatta aaaaaactaa ggaaacattt   5940
ttcttgtttc gagtagataa tgccagcctg ttaaacgccg tcgacgagtc taacggacac   6000
caaccagcga accagcagcg tcgcgtcggg ccaagcgaag cagacggcac ggcatctctg   6060
tcgctgcctc tggaccctc tcgagagttc cgctccaccg ttggacttgc tccgctgtcg   6120
gcatccagaa attgcgtggc ggagcggcag acgtgagcg gcacggcagg cggcctcctc   6180
ctcctctcac ggcaccggca gctacggggg attccttttc caccgctcct tcgctttccc   6240
ttcctcgccc gccgtaataa atagacaccc ctccacacc ctctttcccc aacctcgtgt   6300
tgttcggagc gcacacacac acaaccagat cggcgcgcct taagaaatcc tctcttctcc   6360
tcttcattt caaggtaaat ctctctctct ctctctctct ctgttattcc ttgttttaat   6420
taggtatgta ttattgctag tttgttaatc tgcttatcct atgtatgcct tatgtgaata   6480
tctttatctt gttcatctca tccgtttaga agctataaat ttgttgattt gactgtgtat   6540
ctacacgtgg ttatgtttat atctaatcag atatgaattt cttcatattg ttgcgtttgt   6600
gtgtaccaat ccgaaatcgt tgatttttt catttaatcg tgtagctaat tgtacgtata   6660
catatggatc tacgtatcaa ttgttcatct gtttgtgttt gtatgtatac agatctgaaa   6720
acatcacttc tctcatctga ttgtgttgtt acatacatag atatagatct gttatatcat   6780
tttttttatt aattgtgtat atatatatgt gcatagatct ggattacatg attgtgatta   6840
tttacatgat tttgttattt acgtatgtat atatgtagat ctggactttt tggagttgtt   6900
gacttgattg tatttgtgtg tgtatatgtg tgttctgatt atgtatgtgc   6960
agggcgcgcc ggatcccgg tggtcagtc cctatgtta cgtcctgtag aaaccccaac   7020
ccgtgaaatc aaaaaactcg acggcctgtg ggcattcagt ctggatcgcg aaaactgtgg   7080
aattgatcag cgttggtggg aaagcgcgtt acaagaaagc cgggcaattg ctgtgccagg   7140
cagttttaac gatcagttcg ccgatgcaga tattcgtaat tatgcgggca acgtctgta   7200
tcagcgcgaa gtctttatac cgaaaggttg gcaggccaa cgtatcgtgc tgctttacga   7260
tgcggtcact cattacggca aagtgtgggc caataatcag gaagtgatgg agcatcaggg   7320
cggctatacg ccatttgaag ccgatgtcac gccgtatgtt attgccggga aaagtgtacg   7380
taagtttctg cttctacctt tgatatatat ataataatta tcattaatta gtagtaatat   7440
aatatttcaa atatttttt caaaatatta ataaaaacaa gaatgtagta tatagcaatt   7500
ttattataag tgtgtatatt ttaatttata aattttctaa tatatgacca aaatttgttg   7560
atgtgcaggt atcaccgttt gtgtgaacaa cgaactgaac tggcagacta tcccgccggg   7620
aatggtgatt accgacgaaa acggcaagaa aaagcagtct tacttccatg atttctttaa   7680
ctatgccgga atccatcgca gcgtaatgct ctacaccacg ccgaacacct gggtggacga   7740
tatcaccgtg gtgacgcatg tcgcgcaaga ctgtaaccac gcgtctgttg actggcaggt   7800
ggtggccaat ggtgatgtca gcgttgaact gcgtgatgcg gatcaacagg tggttgcaac   7860
```

```
tggacaaggc actagcggga cttttgcaagt ggtgaatccg cacctctggc aaccgggtga   7920
aggttatctc tatgaactgt gcgtcacagc caaaagccag acagagtgtg atatctaccc   7980
gcttcgcgtc ggcatccggt cagtggcagt gaagggcgaa cagttcctga ttaaccacaa   8040
accgttctac tttactggct tggtcgtca tgaagatgcg gacttgcgtg gcaaaggatt    8100
cgataacgtg ctgatggtgc acgaccacgc attaatggac tggattgggg ccaactccta   8160
ccgtacctcg cattacccctt acgctgaaga gatgctcgac tgggcagatg aacatgcat   8220
cgtggtgatt gatgaaactg ctgctgtcgg ctttaacctc tctttaggca ttggtttcga   8280
agcgggcaac aagccgaaag aactgtacag cgaagaggcg gtcaacgggg aaaactcagca   8340
agcgcacttaa caggcgatta aagagctgat agcgcgtgac aaaaaccacc caagcgttggt  8400
gatgtggagt attgccaacg aaccggatac ccgtccgcaa ggtgcacggg aatatttcgc   8460
gccactggcg gaagcaacgc gtaaactcga cccgacgcgt ccgatcacct gcgtcaatgt   8520
aatgttctgc gacgctcaca ccgataccat cagcgatctc tttgatgtgc tgtgcctgaa   8580
ccgttattac ggatggtatg tccaaagcgg cgatttggaa acggcagaga aggtactgga   8640
aaaagaactt ctggcctggc aggagaaact gcatcagtcg attatcatca ccgaatacgg   8700
cgtggatacg ttagccgggc tgcactcaat gtacaccgac atgtggagtg aagagtatca   8760
gtgtgcatgg ctggatatgt atcaccgcgc ctttgatcgc gtcagcgccg tcgtcggtga   8820
acaggtatgg aatttcgccg attttgcgac ctcgcaaggc atattgcgcg ttggcggtaa   8880
caagaaaggg atcttcactc gcgaccgcaa accgaagtcg gggcttttc tgctgcaaaa    8940
acgctggact ggcatgaact tcggtgaaaa accgcagcag ggaggcaaac aatgaatcaa   9000
caactctcct ggcgcaccat cgtcggctac agcctcggga attgctaccg agctcctgca   9060
ggcctaggat cgttcaaaca tttggcaata aagtttctta agattgaatc ctgttgccgg   9120
tcttgcatgg attatcatat aatttctgtt gaattacgtt aagcatgtaa taattaacat   9180
gtaatgcatg acgttattta tgagatgggt ttttatgatt agagtcccgc aattatacat   9240
ttaatacgcg atagaaaaca aaatatagcg cgcaaactag gataaattat cgcgcgcggt   9300
gtcatctatg ttactagatc ggccggccgt ttaaacttag ttactaatca gtgatcagat   9360
tgtcgtttcc cgccttcact ttaaactatc agtgtttgac aggatatatt gggctgtaaa   9420
cctaagagaa aagagcgttt attagaataa tcggatattt aaaagggcgt gaaaaggttt   9480
atccgttcgt ccatttgtat gtcaatattg ggggggggg aaagccacgt tgtgtctcaa    9540
aatctctgat gttacattgc acaagataaa aatatatcat catgaacaat aaaactgtct   9600
gcttacataa acagtaatac aaggggtgtt cgccaccatg agccatatcc agcgtgaaac   9660
ctcgtgctcc cgcccgcgcc tcaattccaa tatgatgcgc gacctttatg gctacaagtg   9720
ggcgcgcgac aacgtcggcc agtcgggcgc gaccatttat cggctttatg gcaaacccga   9780
tgccccggaa ctgttcctga agcacggcaa aggcagcgtc gcaaacgatg tcaccgatga   9840
gatggtccgc ctgaactggc ttaccgagtt catgccgctc ccgacgatta agcatttcat   9900
ccgtacccccg gacgatgcct ggctcttgac cacggccatt ccgggcaaaa cggccttca    9960
ggtccttgaa gagtacccgg actccggtga gaatatcgtg gacgcccctcg cggtcttcct  10020
ccgccgtttg catagcatcc ccgtgtgcaa ctgccccttc aactcggacc gggttttccg   10080
cctggcacag gcccagtcgc gcatgaataa cggcctcgtt gacgcgagcg atttcgacga   10140
tgaacggaat ggctggccgg tggaacaggt ttggaaggaa atgcacaaac tgcttccgtt   10200
ctcgccggat tcgtggtcca cgcatggtga ttttttccctg gataatctga tctttttgacga  10260
gggcaagctg atcggctgca tcgacgtggg tcgcgtcggt atcgccgacc gctatcagga   10320
cctgcgatc ttgtggaatt gcctcggcga gttctcgccc tcgctccaga gcgcctgtt    10380
ccagaagtac ggcatcgaca acccggatat gaacaagctc cagttccacc tcatgctgga   10440
cgaatttttt tgaacagaat tggttaattg gttgtaacac tggcagagca ttacgctgac   10500
ttgacgggac ggcggctttg ttgaataaat cgaactttg ctgagttgaa ggatcgatga    10560
gttgaaggac cccgtagaaa agatcaaagg atcttcttga gatccttttt ttctgcgcgt   10620
aatctgctgc ttgcaaacaa aaaaaccacc gctaccagcg gtggtttgtt tgccggatca   10680
agagctacca actcttttc cgaaggtaac tggcttcagc agagcgcaga taccaaatac    10740
tgtccttcta gtgtagccgt agttaggcca ccacttcaag aactctgtag caccgcctac   10800
atacctcgct ctgctaatcc tgttaccagt ggctgctgcc agtggcgata gtcgtgtct    10860
taccgggttg gactcaagac gatagttacc ggataaggcg cagcggtcgg gctgaacgg    10920
gggttcgtgc acacagccca gcttggagcg aacgacctac accgaactga gatacctaca   10980
gcgtgagcta tgagaaagcg ccacgcttcc cgaagggaga aaggcggaca ggtatccggt   11040
aagcggcagg gtcggaacag gagagcgcac gagggagctt ccaggggaa acgcctggta    11100
tctttatagt cctgtcgggt ttcgccacct ctgacttgag cgtcgatttt tgtgatgctc   11160
gtcaggggg cggagcctat ggaaaaacgc cagcaacgcg gcctttttac ggttcctggc    11220
cttttgctgg ccttttgctc acatgttctt tcctgcgtta tccctgatt ctgtggataa     11280
ccgtattacc gcctttgagt gagctgatac cgctcgccgc agccgaacga ccgagcgcag   11340
cgagtcagtg agcgaggaag cggaagagcg cctgatgcgg tattttctcc ttacgcatct   11400
gtgcggtatt tcacaccgca taggcgcta taggccgacc cgaagcggcg gggcgtaggg    11460
agcgcagcga ccgaagggta ggcgcttttt gcagctcttc ggctgtgcgc tggcagaca    11520
gttatgcaca ggcaggcgg gttttaagag ttttaataag ttttaaagag ttttaggcgg    11580
aaaaatcgcc ttttttctct tttatatcag tcacttacat gtgtgaccgg ttcccaatgt   11640
acggctttgg gttcccaatg tacgggttcc ggttcccaat gtacggcttt tgccggatca   11700
tgtacgtgct atccacagga aagagacctt ttcgaccttt tcccctgct agggcaattt    11760
gccctagcat ctgctccgta cattaggaac cggcggatgc ttcgcccctcg atcaggttgc   11820
ggtagcgcat gactaggatc gggccagcct gccccgcctc ctccttcaaa tcgtactccg   11880
gcaggtcatt tgacccgatc agcttgcgca cggtgaaaca gaattcttg aactctccgg    11940
cgctgccact gcgttcgtag atcgtcttga caaaccatct ggcttctcc ttgcctcgg     12000
cgcggcgtgc caggcggtag agaaaacggc cgatgccggg gtcgatcaaa agtaatggg    12060
ggtgaaccgt cagcacgtcc gggttcttgc ctttctgtgat ctcgcggtac atccaatcag   12120
caagctcgat ctcgatgtac tccggccgcc cggtttcgct ctttacgatc ttgtagcggc   12180
taatcaaggc ttcacccctcg ataccgtca ccaggcggcc gttcttggcc ttcttggtac   12240
gctgcatgga acgtcggtg tgtttaacc gaatgcaggt ttctaccagg tcgtctttct    12300
gctttccgcc atcggctcgc cggcagaact tgagtacgc cgcaacgtgt ggacggaaca   12360
cgcggccggg cttgtctccc ttcccttccc ggtatcggtt catggattcg ttagatggg   12420
aaaccgccat cagtaccagg tcgtaatccc acacactggc catgccggcg gggcctgcgg   12480
aaacctctac gtgcccgtct ggaagctcgt agcggatcac ctcgccagct cgtcggtcac   12540
gcttcgacag acggaaaacg gccacgtcca tgatgctgcg actatcgcgg gtgcccacgt   12600
```

```
catagagcat cggaacgaaa aaatctggtt gctcgtcgcc cttgggcggc ttcctaatcg    12660
acggcgcacc ggctgccggc ggttgccggg attctttgcg gattcgatca gcggcccctt    12720
gccacgattc accggggcgt gcttctgcct cgatgcgttg ccgctgggcg gcctgcgcgg    12780
ccttcaactt ctccaccagg tcatcaccca gcgccgcgcc gatttgtacc gggccggatg    12840
gtttcgacc gctcacgccg attcctcggg ctttgggggtt ccagtgccat tgcagggccg    12900
gcagacaacc cagccgctta cgcctggcca accgcccgtt cctccacaca tgggcattc    12960
cacggcgtcg gtgcctggtt gttcttgatt ttccatgccg cctcctttag ccgctaaaat    13020
tcatctactc atttattcat ttgctcattt actctggtag ctgcgcgatg tattcagata    13080
gcagctcggt aatggtcttg ccttggcgta ccgcgtacat cttcagcttg gtgtgatcct    13140
ccgccggcaa ctgaaagttg acccgcttca tggctggcgt gtctgccagg ctggccaacg    13200
ttgcagcctt gctgctgcgt gcgctcggac ggccggcact tagcgtgttt gtgcttttgc    13260
tcatttctc tttacctcat taactcaaat gagttttgat ttaatttcag cggccagcgc    13320
ctggacctcg cgggcagcgt cgccctcggg ttctgattca agaacggttg tgccggcggc    13380
ggcagtgcct gggtagctca cgcgctgcgt gatacgggac tcaagaatgg gcagctgtca    13440
cccggccagc gcctcggcaa cctcaccgcc gatgcgcgtg cctttgatcg cccgcgcacc    13500
gacaaaggcc gcttgtagcc ttccatccgt gacctcaatg cgctgcttaa ccagctccac    13560
caggtcggcg gtggcccaaa tgtcgtaagg cttggctgc accggaatca gcacgaagtc    13620
ggctgccttg atcgcggaca cagccaagtc cgccgcctcg gctccgt cgatcactac    13680
gaagtcgcgc cggccgatgg ccttcacgtc gcggtcaatc gtcgggcggt cgatgccgac    13740
aacggttagc ggttgatctt cccgcacggc cgcccaatcg cgggcactgc cctggggatc    13800
ggaatcgact aacagaacat cggccccggc gagttgcagg gcgcgggcta gatgggttgc    13860
gatggtcgtc ttgcctgacc cgcctttctg gttaagtcag gcgataacct tcatgcgttc    13920
cccttgcgta tttgtttatt tactcatcgc atcatatacg cagcgaccgc atgacgcaag    13980
ctgttttact caaatacaca tcacctttt agatgatca                          14019

SEQ ID NO: 76           moltype = DNA length = 28
FEATURE                 Location/Qualifiers
misc_feature            1..28
                        note = synthetic sequence
source                  1..28
                        mol_type = other DNA
                        organism = synthetic construct
SEQUENCE: 76
atatacgcgt ttagatctcg tgccgtcg                                          28

SEQ ID NO: 77           moltype = DNA length = 32
FEATURE                 Location/Qualifiers
misc_feature            1..32
                        note = synthetic sequence
source                  1..32
                        mol_type = other DNA
                        organism = synthetic construct
SEQUENCE: 77
atatggcgcg cctttgatca agcctgttca ca                                     32

SEQ ID NO: 78           moltype = DNA length = 33
FEATURE                 Location/Qualifiers
misc_feature            1..33
                        note = synthetic sequence
source                  1..33
                        mol_type = other DNA
                        organism = synthetic construct
SEQUENCE: 78
atatacgcgt ttaagaaatc ctctcttctc ctc                                    33

SEQ ID NO: 79           moltype = DNA length = 38
FEATURE                 Location/Qualifiers
misc_feature            1..38
                        note = synthetic sequence
source                  1..38
                        mol_type = other DNA
                        organism = synthetic construct
SEQUENCE: 79
atatggcgcg ccctgcacat acataacata tcaagatc                               38

SEQ ID NO: 80           moltype = DNA length = 13590
FEATURE                 Location/Qualifiers
misc_feature            1..13590
                        note = vector sequence
source                  1..13590
                        mol_type = other DNA
                        organism = synthetic construct
SEQUENCE: 80
gtgattttgt gccgagctgc cggtcgggga gctgttggct ggctggtggc aggatatatt      60
gtggtgtaaa caaattgacg cttagacaac ttaataacac attgcggacg tctttaatgt     120
actgaattta gttactgatc actgattaag tactgatatc ggtaccaagc ttccgcggct     180
gcagtgcagc gtgacccgt cgtgcccctc tctagagata atgagcattg catgtctaag     240
ttataaaaaa ttaccacata ttttttttgt cacacttgtt tgaagtgcag tttatctatc     300
tttatacata tatttaaact ttactctacg aataataaa tctatagtac tacaataata     360
```

```
tcagtgtttt agagaatcat ataaatgaac agttagacat ggtctaaagg acaattgagt    420
attttgacaa caggactcta cagttttatc ttttagtgt gcatgtgttc tccttttttt    480
ttgcaaatag cttcacctat ataatacttc atccatttta ttagtacatc catttagggt    540
ttaggggttaa tggttttat agactaattt ttttagtaca tctatttat tctattttag    600
cctctaaatt aagaaaacta aaactctatt ttagttttt tatttaatag tttagatata    660
aaatagaata aaataaagtg actaaaaatt aaacaaatac cctttaagaa attaaaaaaa    720
ctaaggaaac atttttcttg tttcgagtag ataatgccag cctgttaaac gccgtcgacg    780
agtctaacgg acaccaacca gcgaaccagc agcgtcgcgt cgggccaagc gaagcagacg    840
gcacggactc tctgtcgctg cctctggacc cctctggaga gttccgctcc accgttggac    900
ttgctccgct gtcggcatcc agaaattgcg tggcggacg gcagacgtga gccggcacgg    960
caggcggcct cctcctcctc tcacggcacc ggcagctacg gggattcct ttccaccgc    1020
tccttcgctt tccttcctc gcccgccgta taaatagac ccccctcca caccctcttt    1080
ccccaacctc gtgttgttcg gagcgcacac acacacaacc agatctcccc caaatccacc    1140
cgtcggcacc tccgcttcaa ggtacgccgc tcgtcctccc ccccccccc cctctctacc    1200
ttctctagat cggcgttccg gtccatggtt agggcccggt agttctactt ctgttcatgt    1260
ttgtgttaga tccgtgtttg tgttagatcc gtgctgctag cgttcgtaca cggatgcgac    1320
ctgtacgtca gacacgttct gattgctaac ttgccagtgt ttctcttgg ggaatcctgg    1380
gatggctcta gccgttccgc agacgggatc gatttcatga ttttttgt ttcgttgcat    1440
agggttggt ttgcccttt cctttatttc aatatatgcc gtgcacttgt ttgtcgggtc    1500
atcttttcat gcttttttt gtcttggttg tgatgatgtg gtctggttgg gcggtcgttc    1560
tagatcggag tagaattctg tttcaaacta cctggtggat ttattaattt tggatctgta    1620
tgtgtgtgcc atacatattc atagttacga attgaagatg atggatggaa atatcgatct    1680
aggataggta tacatgttga tgcgggtttt actgatgcat atacagagat gcttttgtt    1740
cgcttggttg tgatgatgtg gtgtggttgg gcggtcgttc attcgttcta gatcggagta    1800
gaatactgtt tcaaactacc tggtgtattt attaattttg gaactgtatg tgtgtgtcat    1860
acatcttcat agttacgagt ttaagatgga tggaaatatc gatctaggat aggtatacat    1920
gttgatgtgg gttttactga tgcatataca tgatggcata tgcagcatct attcatatgc    1980
tctaaccttg agtaccatc tattataata aacaagtatg ttttataatt atttcgatct    2040
tgatatactt ggatgatggc atatgcagca gctatatgtg gatttttta gccctgcctt    2100
catacgctat ttatttgctt ggtactgttt cttttgtcga tgctcaccct gttgtttggt    2160
gttacttctg cagcccgggg gatccactag ttctagaaac catggccacc gccgccgccg    2220
cgtctaccgc gctcactggc gccactaccg ctgcgcccaa ggcgaggcgc cgggcgcacc    2280
tcctggccac ccgccgcgcc ctcgccgcgc ccatcaggtg ctcagcggcg tcacccgcca    2340
tgccgatggc tcccccggcc accccgctcc ggccgtgggg cccaccgat ccccgcaagg    2400
gcgccgacat gcgtcgtcgag tccctcgagc gctgcggcgt ccgcgacgtc ttcgcctacc    2460
ccggcggcac gtccatggag atccaccagg cactcacccg ctccccgtc atcgccaacc    2520
acctcttccg ccacgagcaa ggggaggcct ttgcggcctc cggctacgcg cgctcctcgg    2580
gccgcgtcgg cgtctgcatc gccacctccg gccccggcgc caccaacctt gtctccgcgc    2640
tcgccgacgc gctgctcgat tccgtcccca tggtcgccat cacgggacag gtgccgcac    2700
gcatgattgg caccgacgcc ttccaggaga cgcccatcgt cgaggtcacc cgctccatca    2760
ccaagcacaa ctacctggtc ctcgacgtcg acgacatccc ccgcgtcgtg caggaggctt    2820
tcttcctcgc ctcctctggt cgaccggggc cggtgcttgt cgacatcccc aaggacatcc    2880
agcagagat ggcggtgcct gtctgggaca agccatga tctgcctggg tacattgcgt    2940
gccttcccaa gcccctgcg actgagttgc ttgagcaggt gctgcgtctt gttggtgaat    3000
cccggcgccc tgttctttat gttggcgtg gctgcgcagc atctcggtgag gagttgcgac    3060
gctttgtgga gctgactgga atcccggtca caactactct tatgggcctc ggcaacttcc    3120
ccagcgacga cccactgtct ctgcgcatgc taggtatgca tggcacggtg tatgcaaatt    3180
atgcagtgga taaggccgat ctgttgcttg cacttggtgt gcggtttgat gatcgtgtga    3240
cagggaagat tgaggctttt gcaagcaggg ctaagattgt gcacgttgat attgatccgg    3300
ctgagattgg caagaacaag cagccacatg tgtccatctg tgcagatgtt aagcttgctt    3360
tgcagggcat gaatgctctt cttgaaggaa gcacatcaaa gaagagcttt gacttttgct    3420
catgaacga tgagttggat cagcagaaga gggaattccc ccttgggtat aaaacatcta    3480
atgaggagat ccagccacaa tatgctattc aggttcttga tgagctgacg aaaggcgagg    3540
ccatcatcgg cacaggtgtt gggcagcacc agatgtgggc ggcacagtac tacacttaca    3600
agcggccaag gcagtggttg tcttcagctg gtcttggatt ggtttgccgg tatggattt    3660
ctgctgctgg tgcttctgtg gccaacccag gtgttactgt tgttgacatc gatggagatg    3720
gtagctttct catgaacgtt caggagctag ctatgatccg aattgagaac ctcccggtga    3780
aggtcttgt gctaaacaac cagcacctgg ggatggtggt gcagtgggag gacaggttct    3840
ataaggccaa cagagcgcac acatactgg gaaacccaga gaatgaaagt gagatatatc    3900
cagatttcgt gacgatcgcc aaagggttca acattccagc ggtccgtgtg acaaagaaga    3960
acgaagtccg cgcagcgata aagaagatgc tcgagactcc agggccgtac ctcttggata    4020
taatcgtccc acaccaggag catgtgttgc ctatgatccc taatggtggg gctttcaaagg    4080
atatgatcct ggatggtgat ggcaggactg tgtactgatc taaaatccag caagcaactg    4140
atctaaaatc cagcaagcac cgcctccctg ctagtacaag ggtgatatgt ttttatctgt    4200
gtgatgttct cctgtattct atctttttt gtaggccgtc agctatcgt tatgtaatc    4260
ctatgtagct tccgaccttg taattgtgta gtctgttgtt ttccttctgg catgtgtcat    4320
aagagatcat ttaagtgcct tttgctacat ataaataaga taataagcac tgctatgcag    4380
tggttctgaa ttggctctg ttgccaaatt taagtgtcca actggtcctt gcttttgttt    4440
tcgctatttt tttccttttt tagttattat tatattattta atttcaactc aacatatgtt    4500
gtatggaata atgctaggg ctgcaatttca aactatttta caaaccagaa tggcatttc    4560
gtggtttgag gggagtgaaa aaaaatgagg catttgactg aattagttac ctgatccatt    4620
ttcgtggttt ggatcattgg aattaaattc cattctaata atagtaattt tggcatatat    4680
caattaagtt aattcggttt tatgcaaaat atatttgtat actattatta tcaagatgtc    4740
ggagatattt atatgctaca ttttactat acaggagtga gatgaagagt gtcatgtaag    4800
ttacacagta gaaacaaatt ctattaatgc ataaaatcat ttccatcatc caccctatga    4860
atttgagata gacctatatc taaactttga aaagtggttg aatatcaaat tccaaattaa    4920
ataagttatt ttattgagtg aattctaatt tctctaaaac gaagggatct aaacgccctc    4980
taaagctaat ttggaaactc aaactttctt agcattggag gggattgaga aaaaatatta    5040
attcattttc atctcaatca ttcaatctcc aaagagattt gagttcctta ttagtctgtt    5100
```

```
ccatgcatca aatcggctca atgtgtcatt atttgccatg acgattgacg agttgttctg   5160
gggcctagcg cttccacgc cgatgtgctg gggcctggtc ctggagaaga cagcttgata   5220
tttaaagcta tcaattgttt caattgattc ccacttcatt tttctaaatg tagaaaacgg   5280
tgacgtataa gaaaaagaat gaattaggac ttttattccg tacactaatc tagagcggcc   5340
caagccttgta cactagtacg cgtcaattga tttaaattta attaatgcag tgcagcgtga   5400
cccggtcgtg cccctctcta gagataatga gcattgcatg tctaagttat aaaaaattac   5460
cacatatttt ttttgtcaca cttgtttgaa gtgcagttta tctatcttta tacatatatt   5520
taaactttac tctacgaata atataatcta tagtactaca ataatatcag tgttttagag   5580
aatcatataa atgaacagtt agacatggtc taaaggacaa ttgagtattt tgacaacagg   5640
actctacagt tttatctttt tagtgtgcat gtgttctcct ttttttttgc aaatagcttc   5700
acctatataa tacttcatcc atttttattag tacatccatt tagggtttag ggttaatggt   5760
ttttatagac taatttttt agtacatcta ttttattcta tttagcctc taaattaaga   5820
aaactaaaac tctattttag tttttttatt taatagttta gatataaaat agaataaaat   5880
aaagtgacta aaaattaaac aaatacccctt taagaaatta aaaaaactaa ggaaacattt   5940
ttcttgtttc gagtagataa tgccagcctg ttaaacgccg tcgacgagtc taacggacac   6000
caaccagcga accagcagcg tcgcgtcggg ccaagcgaag cagacggcac ggcatctctg   6060
tcgctgcctc tggaccccctc tcgagagttc cgctccaccg ttggacttgc tccgctgtcg   6120
gcatccagaa attgcgtggc ggagcggcag acgtgagccg gcacggcagg cggcctcctc   6180
ctcctctcac ggcaccggca gctacggggg attccttttcc caccgctcct tcgctttccc   6240
ttcctcgccc gccgtaataa atagacaccc cctccacacc ctctttcccc aacctcgtgt   6300
tgttcggagc gcacacacac acaaccagat cggcgcgttt aagaaatcct ctcttctcct   6360
cttcatttc aaggtaaatc tctctctctc tctctctctc tgttattcct tgttttaatt   6420
aggtatgtat tattgctagt ttgttaatct gcttatctta tgtatgccctt atgtgaatat   6480
ctttatcttg ttcatctcat ccgtttagaa gctataaatt tgttgatttg actgtgtatc   6540
tacacgtggt tatgtttata tctaatcaga tatgaatttc ttcatattgt tgcgtttgtg   6600
tgtaccaatc cgaaatcgtt gatttttttc atttaatcgt gtagctaatt gtacgtatac   6660
atatggatct acgtatcaat tgttcatctg tttgtgtttg tatgtataca gatctgaaaa   6720
catcacttct ctcatctgat tgtgttgtta catacataga tatagatctg ttatatcatt   6780
ttttttatta attgtgtata tatatatgtg catagatctg gattacatga ttgtgattat   6840
ttacatgatt ttgttattta cgtatgtata tatgtagatc tggactttttt ggagttgttg   6900
acttgattgt atttgtgtgt gtatatgtgt gttctgatct tgatatgtta tgtatgtgca   6960
gggcgcgcca ccatggaaga cgccaaaaac ataagaaag gcccggcgcc attctatccg   7020
ctggaagatg gaaccgctgg agagcaactg cataaggcta tgaagagata cgccctggtt   7080
cctggaacaa ttgcttttac agatgcacat atcgaggtgg acatcactta cgctgagtac   7140
ttcgaaatgt ccgttcggtt ggcagaagct atgaaacgat atgggctgaa tacaaatcac   7200
agaatcgtcg tatgcagtga aaactctctt caattcttta tgccggtgtt gggcgcgtta   7260
tttatcggag ttgcagttgc gcccgcgaac gacatttata tgaacgtga attgctcaac   7320
agtatgggca tttcgcagcc taccgtggtg ttcgtttcca aaaagggtt gcaaaaaatt   7380
ttgaacgtgc aaaaaaagct cccaatcatc caaaaaatta ttatcatgga ttctaaaacg   7440
gattaccagg gatttcagtc gatgtacacg ttcgtcacat ctcatctacc tcccggtttt   7500
aatgaatacg attttgtgcc agagtccttc gatagggaca agacaattgc actgatcatg   7560
aactcctctg gatctactgg tctgcctaaa ggtgtcgctc tgcctcatag aactgcctgc   7620
gtgagattct cgcatgccag agatcctatt tttggcaatc aagcattctt ggatactgcg   7680
attttaagtg ttgttccatt ccatcacggt tttggaatgt ttactacact cggatattg   7740
atatgtggat ttcgagtcgt cttaatgtat agatttgaag aagagctgtt tctgaggagc   7800
cttcaggatt acaagattca aagtgcgctg ctggtgccaa cccatactcte cttcttcgcc   7860
aaaagcactc tgattgacaa atacgattta tctaatttac acgaaattgc ttctggtggc   7920
gctcccctct ctaaggaagt cggggaagcg gttgccaaga ggttccatct gccaggtatc   7980
aggcaaggat atgggctcac tgagactaca tcagctattc tgattacacc cgagggggat   8040
gataaaccgg gcgcggtcgg taaagttgtt ccatttttg aagcgaaggt tgtggatctg   8100
gataccgggaa aacgctggg cgttaatcaa agaggcgaac tgtgtgtgag aggtcctatg   8160
attatgtccg gttatgtaaa caatccgaa gcgaccaacg ccttgattga caaggatgga   8220
tggctacatt ctggagacat agcttactgg gacgaagacg aacacttctt catcgttgac   8280
cgcctgaagt ctctgattaa gtacaaaggc tatcaggtgg ctcccgctga attggaatcc   8340
atcttgctcc aacaccccaa catcttcgac gcaggtgtcg caggtcttcc cgacgatgac   8400
gccggtgaac ttcccgccgc cgttgttgtt ttggagcacg gaaagacgat gacggaaaaa   8460
gagatcgtgg attacgtcgc cagtcaagta acaaccgcga aaagttgcg cggaggagtt   8520
gtgtttgtgg acgaagtacc gaaaggtctt accggaaaac tcgacgcaag aaaaatcaga   8580
gagatcctca taaaggccaa gaagggcgga aagatcgccg tgtaacctgc aggcctagga   8640
tcgttcaaac atttggcaat aaagtttctt aagattgaat cctgttgccg gtcttgcgat   8700
gattatcata taatttctgt tgaattacgt taagcatgta ataattaaca tgtaatgcat   8760
gacgttattt atgagatggg ttttatgat tagagtcccg caattataca tttaatacgc   8820
gatagaaaac aaaatatagc gcgcaaacta ggataaatta tcgcgcgcgg tgtcatctat   8880
gttactagat cggcggccg tttaaactta gttactaatc agtgatcaga ttgtcgtttc   8940
ccgccttcac tttaaactat cagtgtttga caggatatat tggcgggtaa acctaagaga   9000
aaagagcgtt tattagaata tcggatatt taaagggcg tgaaaggtt tatccgttcg   9060
tccatttgta tgtcaatatt ggggggggg gaaagccacg ttgtgtctca aaatctctga   9120
tgttacattg cacaagataa aaatatatca tcatgaacaa taaaactgtc tgcttacata   9180
aacagtaata caaggggtgt tcgccaccat gagccatatc cagcgtgaaa cctcgtgtc   9240
ccgcccgcgc ctcaattcca atatggatgc cgacctttat ggctacaagt gggcgcgcga   9300
caacgtcggc cagtcgggcg cgaccatta tcggctttat ggcaaacccg atgcccggaa   9360
actgttcctg aagcacggca aaggcagcgt cgcaaacgat gtcaccgatg atggtccgg   9420
cctgaactgg cttaccgagt tcatgccgct gccgacgatt aagcatttca tccgtacccc   9480
ggacgatgcc tggcttctga ccacggcaa acgcctttc aggtccttga   9540
agagtacccg gactccggtg agaatatcgt ggacgccctc gcggtcttcc tccgccgttt   9600
gcatagcatc cccgtgtgca actgcccctt caactcggac cgggttttcc gcctggcaca   9660
ggcccagtcg cgcatgaata acggcctcgt tgacgcgagc gatttcgacg atgaacgaa   9720
tggctggccg gtgaacagg tttggaagga atgcacaaa ctgcttccgt tctcgccgga   9780
ttcggtggtc acgcatggtg attttccct ggataatctg atctttgacg agggcaagct   9840
```

-continued

```
gatcggctgc atcgacgtgg gtcgcgtcgg tatcgccgac cgctatcagg acctggcgat    9900
cttgtggaat tgcctcggcg agttctcgcc ctcgctccag aagcgcctgt tccagaagta    9960
cggcatcgac aacccggata tgaacaagct ccagttccac ctcatgctgg acgaattttt   10020
ttgaacagaa ttggttaatt ggttgtaaca ctggcagagc attacgctga cttgacggga   10080
cggcggcttt gttgaataaa tcgaacttttt gctgagttga aggatcgatg agttgaagga   10140
ccccgtagaa aagatcaaag gatcttcttg agatccttt tttctgcgcg taatctgctg   10200
cttgcaaaca aaaaaaccac cgctaccagc ggtggtttgt ttgccggatc aagagctacc   10260
aactcttttt ccgaaggtaa ctggcttcag cagagcgcag ataccaaata ctgtccttct   10320
agtgtagccg tagttaggcc accacttcaa gaactctgta gcaccgccta catacctcgc   10380
tctgctaatc ctgttaccag tggctgctgc cagtggcgat aagtcgtgtc ttaccgggtt   10440
ggactcaaga cgatagttac cggataaggc gcagcggtcg ggctgaacgg ggggttcgtg   10500
cacacagccc agcttggagc gaacgaccta caccgaactg agatacctac agcgtgagct   10560
atgagaaagc gccacgcttc ccgaaggag aaaggcggac aggtatccgg taagcggcag   10620
ggtcggaaca ggagagcgca cgagggagcc tccaggggga aacgcctggt atctttatag   10680
tcctgtcggg tttcgccacc tctgacttga gcgtcgattt ttgtgatgct cgtcagggggg  10740
gcggagccta tggaaaaacg ccagcaacgc ggccttttta cggttcctgg ccttttgctg   10800
gccttttgct cacatgttct ttcctgcgtt atccctgat tctgtggata accgtattac   10860
cgcctttgag tgagctgata ccgctcgccg cagccgaacg accgagcgca gcgagtcagt   10920
gagcgaggaa gcggaagagc gcctgatgcg gtattttctc cttacgcatc tgtgcggtat   10980
ttcacaccgc ataggccgcg ataggccgac gcgaagcggc ggggcgtagg gagcgcagcg   11040
accgaagggt aggcgctttt tgcagctctt cggctgtgcg ctggccagac agttatgcac   11100
aggccggcgta ggttttaaga gttttaataa gttttaaaga gttttaggcg gaaaaatcgc   11160
cttttttctc ttttatatca gtcacttaca tgtgtgaccg gttcccaatg tacggctttg   11220
ggttcccaat gtacgggttc cggttcccaa tgtacggctt tgggttccca atgtacgtgc   11280
tatccacagg aaagagacct tttcgacctt ttttcccctgc tagggcaatt tgccctagca   11340
tctgctccgt acattaggaa ccggcggatg cttcgccctc gatcaggttg cggtagcgca   11400
tgactaggat cgggccagcc tgcccccgcct cctccttcaa atcgtactcc ggcaggtcat   11460
ttgacccgat cagcttgcgc acggtgaaac agaacttctt gaactctccg gcgctgccac   11520
tgcgttcgta gatcgtcttg aacaaccatc tggcttctgc cttgcctgcg gcgcggcgtg   11580
ccaggcggta gagaaaacgg ccgatgccgg ggtcgatcaa aaagtaatcg gggtgaaccg   11640
tcagcacgtc cgggttcttg ccttctgtga tctgcgggta catccaatca gcaagctcga   11700
tctcgatgta ctccggccgc ccggtttcgc tctttacgat cttgtagcgg ctaatcaagg   11760
cttcaccctc ggataccgtc accaggcggc cgttcttggc cttcttggta cgctgcatgg   11820
caacgtgcgt ggtgtttaac cgaatgcagg tttctaccag gtcgtctttc tgcttttccgc  11880
catcgctcg ccggcagaac ttgagtacgt ccgcaacgtg tggacggaac acgcggccgg   11940
gcttgtctcc cttccccttcc cggtatcggt tcatggattc ggttagatgg gaaaccgcca   12000
tcagtaccag gtcgtaatcc cacacactgg ccatgccggc ggggcctgcg gaaacctcta   12060
cgtgcccgtc tggaagctcg tagcggatca cctcgccagc ctgtcggtca cgcttcgaca   12120
gacggaaaac ggccacgtcc atgatgctgc gactatcgcg ggtgcccacg tcatagagca   12180
tcggaacgaa aaaatctggt tgctcgtcgc ccttgggcgg cttcctaatc gacggcgcac   12240
cggctgccgg cggttgccgg gattctttgc ggattcgatc agcggcccct tgccacgatt   12300
caccggggcg tgcttctgcc tcgatgcgtt gccgctgggc ggcctgcgcg gccttcaact   12360
tctccaccag gtcatcaccc agcgccgcc cgatttgtac cgggccggat ggtttgcgac   12420
cgctcacgcc gattcctcgg gcttgggggt tccagtgcca ttgcagggcc ggcagacaac   12480
ccagccgctt acgcctggcc aaccgcccgt tcctccacac atggggcatt ccacggcgtc   12540
ggtgcctggt tgttcttgat tttccatgcc gcctccttta gccgctaaaa ttcatctact   12600
catttattca tttgctcatt tactctggta gctgcgcgat gtattcagat agcagctcgg   12660
taatggtctt gccttggcgt accgcgtaca tcttcagctt ggtgtgatcc tccgccgca   12720
actgaaagtt gacccgcttc atggctggcg tgtctgccag gctggccaac gttgcagcct   12780
tgctgctgcg tgcgctcgga cggccggcac ttagcgtgtt tgtgcttttg ctcattttct   12840
ctttacctca ttaactcaaa tgagttttga tttaatttca gcggccagcg cctggacctc   12900
gcgggcagcg tcgccctcgg gttctgattc aagaacggtt gtgccggcgg cggcagtgcc   12960
tgggtagctc acgcgctgcg tgatacggga ctcaagaatg ggcagctcgt acccggccag   13020
cgcctcggca acctcaccgc cgatgcgcgt gcctttgatc gcccgcgaca cgacaaaggc   13080
cgcttgtagc cttccatccg tgacctcaat gcgctgctta accagctcca ccaggtcggc   13140
ggtggcccaa atgtcgtaag ggcttggctg caccggaatc agcacgaagt cggctgcctt   13200
gatcgcggac acagccaagt ccgccggcct gggcgctccg tcgatcacta cgaagtcgcg   13260
ccggccgatg gccttcacgt cgcggtcaat cgtcgggcgg tcgatgccga caacggttag   13320
cggttgatct tcccgcacgg ccgcccaatc gcggcactg ccctggggat cggaatcgac   13380
taacagaaca tcggcccgg cgagttgcag ggcgcgggct agatgggttg cgatggtcgt   13440
cttgcctgac ccgcctttct ggttaagtac agcgataacc ttcatgcgtt ccccttgcgt   13500
atttgtttat ttactcatcg catcatatac gcagcgaccg catgacgcaa gctgttttac   13560
tcaaatacac atcacctttt tagatgatca                                    13590
```